(12) United States Patent
Lin et al.

(10) Patent No.: US 6,322,972 B1
(45) Date of Patent: Nov. 27, 2001

(54) TNF RECEPTOR DEATH DOMAIN LIGAND PROTEINS AND INHIBITORS OF LIGAND BINDING

(75) Inventors: Lih-Ling Lin, Concord; Jennifer Chen, Chestnut Hill; Andrea R. Schievella, Winchester; James Graham, Somerville, all of MA (US)

(73) Assignee: Genetics Institute, Inc., Cambridge, MA (US)

( * ) Notice: Subject to any disclaimer, the term of this patent is extended or adjusted under 35 U.S.C. 154(b) by 0 days.

(21) Appl. No.: 09/185,258

(22) Filed: Nov. 2, 1998

Related U.S. Application Data

(62) Division of application No. 08/839,032, filed on Apr. 23, 1997, now Pat. No. 5,891,675, which is a division of application No. 08/698,551, filed on Aug. 15, 1996, now Pat. No. 5,712,381, which is a continuation-in-part of application No. 08/602,228, filed on Feb. 15, 1996, now Pat. No. 5,843,675, which is a continuation-in-part of application No. 08/533,901, filed on Sep. 26, 1995, now Pat. No. 5,852,173, which is a continuation-in-part of application No. 08/494,440, filed on Jun. 19, 1995, now Pat. No. 5,849,501, which is a continuation-in-part of application No. 08/327,514, filed on Oct. 19, 1994, now abandoned.

(51) Int. Cl.[7] ............................. C12Q 1/68; G01N 33/53
(52) U.S. Cl. ................................. 435/6; 435/7.1; 435/7.2
(58) Field of Search ............................ 435/7.1, 7.2, 69.1, 435/501, 6; 530/350; 536/23.5

(56) References Cited

U.S. PATENT DOCUMENTS 5,563,039 * 10/1996 Goeddel et al. ...................... 435/7.1

OTHER PUBLICATIONS

Hsu et al. The TNF Receptor 1–Associated Protein TRADD Signals Cell Death and NF–kappa B Activation. Cell 81:495–504, May 1995.*

* cited by examiner

*Primary Examiner*—John Ulm
(74) *Attorney, Agent, or Firm*—Lahive & Cockfield, LLP; Amy E. Mandragouras, Esq.

(57) ABSTRACT

Novel TNF receptor death domain ("TNF-R1-DD") ligand proteins are disclosed. Polynucleotides encoding the TNF-R1-DD ligand protein are also disclosed, along with vectors, host cells, and methods of making the TNF-R1-DD ligand protein. Pharmaceutical compositions containing the TNF-R1-DD ligand protein, methods of treating inflammatory conditions, and methods of inhibiting TNF-R death domain binding are also disclosed. Methods of identifying inhibitors of TNF-R death domain binding and inhibitors identified by such methods are also disclosed.

51 Claims, 8 Drawing Sheets

SEQUENCE LISTING

<160> NUMBER OF SEQ ID NOS: 19

<210> SEQ ID NO 1
<211> LENGTH: 2158
<212> TYPE: DNA
<213> ORGANISM: Homo sapiens
<220> FEATURE:
<221> NAME/KEY: CDS
<222> LOCATION: (2)..(1231)

<400> SEQUENCE: 1

```
c agc aat gca ggt gat gga cca ggt ggc gag ggc agt gtt cac ctg gca        49
  Ser Asn Ala Gly Asp Gly Pro Gly Gly Glu Gly Ser Val His Leu Ala
   1               5                  10                  15 agc tct cgg ggc act ttg tct gat agt gaa att gag acc aac tct gcc        97
Ser Ser Arg Gly Thr Leu Ser Asp Ser Glu Ile Glu Thr Asn Ser Ala
             20                  25                  30 aca agc acc atc ttt ggt aaa gcc cac agc ttg aag cca agc ata aag       145
Thr Ser Thr Ile Phe Gly Lys Ala His Ser Leu Lys Pro Ser Ile Lys
         35                  40                  45 gag aag ctg gca ggc agc ccc att cgt act tct gaa gat gtg agc cag       193
Glu Lys Leu Ala Gly Ser Pro Ile Arg Thr Ser Glu Asp Val Ser Gln
 50                  55                  60 cga gtc tat ctc tat gag gga ctc cta ggc aaa gag cgt tct act tta       241
Arg Val Tyr Leu Tyr Glu Gly Leu Leu Gly Lys Glu Arg Ser Thr Leu
 65                  70                  75                  80 tgg gac caa atg caa ttc tgg gaa gat gcc ttc tta gat gct gtg atg       289
Trp Asp Gln Met Gln Phe Trp Glu Asp Ala Phe Leu Asp Ala Val Met
                 85                  90                  95 ttg gag aga gaa ggg atg ggt atg gac cag ggt ccc cag gaa atg atc       337
Leu Glu Arg Glu Gly Met Gly Met Asp Gln Gly Pro Gln Glu Met Ile
            100                 105                 110 gac agg tac ctg tcc ctt gga gaa cat gac cgg aag cgc ctg gaa gat       385
Asp Arg Tyr Leu Ser Leu Gly Glu His Asp Arg Lys Arg Leu Glu Asp
        115                 120                 125 gat gaa gat cgc ttg ctg gcc aca ctt ctg cac aac ctc atc tcc tac       433
Asp Glu Asp Arg Leu Leu Ala Thr Leu Leu His Asn Leu Ile Ser Tyr
    130                 135                 140 atg ctg ctg atg aag gta aat aag aat gac atc cgc aag aag gtg agg       481
Met Leu Leu Met Lys Val Asn Lys Asn Asp Ile Arg Lys Lys Val Arg
145                 150                 155                 160 cgc cta atg gga aag tcg cac att ggg ctt gtg tac agc cag caa atc       529
Arg Leu Met Gly Lys Ser His Ile Gly Leu Val Tyr Ser Gln Gln Ile
                165                 170                 175 aat gag gtg ctt gat cag ctg gcg aac ctg aat gga cgc gat ctc tct       577
Asn Glu Val Leu Asp Gln Leu Ala Asn Leu Asn Gly Arg Asp Leu Ser
            180                 185                 190 atc tgg tcc agt ggc agc cgg cac atg aag aag cag aca ttt gtg gta       625
Ile Trp Ser Ser Gly Ser Arg His Met Lys Lys Gln Thr Phe Val Val
        195                 200                 205 cat gca ggg aca gat aca aac gga gat atc ttt ttc atg gag gtg tgc       673
His Ala Gly Thr Asp Thr Asn Gly Asp Ile Phe Phe Met Glu Val Cys
    210                 215                 220 gat gac tgt gtg gtg ttg cgt agt aac atc gga aca gtg tat gag cgc       721
Asp Asp Cys Val Val Leu Arg Ser Asn Ile Gly Thr Val Tyr Glu Arg
225                 230                 235                 240
```

```
tgg tgg tac gag aag ctc atc aac atg acc tac tgt ccc aag acg aag          769
Trp Trp Tyr Glu Lys Leu Ile Asn Met Thr Tyr Cys Pro Lys Thr Lys
                245                 250                 255 gtg ttg tgc ttg tgg cgt aga aat ggc tct gag acc cag ctc aac aag          817
Val Leu Cys Leu Trp Arg Arg Asn Gly Ser Glu Thr Gln Leu Asn Lys
            260                 265                 270 ttc tat act aaa aag tgt cgg gag ctg tac tac tgt gtg aag gac agc          865
Phe Tyr Thr Lys Lys Cys Arg Glu Leu Tyr Tyr Cys Val Lys Asp Ser
        275                 280                 285 atg gag cgc gct gcc gcc cga cag caa agc atc aaa ccc gga cct gaa          913
Met Glu Arg Ala Ala Ala Arg Gln Gln Ser Ile Lys Pro Gly Pro Glu
    290                 295                 300 ttg ggt ggc gag ttc cct gtg cag gac ctg aag act ggt gag ggt ggc          961
Leu Gly Gly Glu Phe Pro Val Gln Asp Leu Lys Thr Gly Glu Gly Gly
305                 310                 315                 320 ctg ctg cag gtg acc ctg gaa ggg atc aac ctc aaa ttc atg cac aat         1009
Leu Leu Gln Val Thr Leu Glu Gly Ile Asn Leu Lys Phe Met His Asn
                325                 330                 335 cag gtt ttc ata gag ctg aat cac att aaa aag tgc aat aca gtt cga         1057
Gln Val Phe Ile Glu Leu Asn His Ile Lys Lys Cys Asn Thr Val Arg
            340                 345                 350 ggc gtc ttt gtc ctg gag gaa ttt gtt cct gaa att aaa gaa gtg gtg         1105
Gly Val Phe Val Leu Glu Glu Phe Val Pro Glu Ile Lys Glu Val Val
        355                 360                 365 agc cac aag tac aag aca cca atg gcc cac gaa atc tgc tac tcc gta         1153
Ser His Lys Tyr Lys Thr Pro Met Ala His Glu Ile Cys Tyr Ser Val
    370                 375                 380 tta tgt ctc ttc tcg tac gtg gct gca gtt cat agc agt gag gaa gat         1201
Leu Cys Leu Phe Ser Tyr Val Ala Ala Val His Ser Ser Glu Glu Asp
385                 390                 395                 400 ctc aga acc ccg ccc cgg cct gtc tct agc tgatggagag gggctacgca           1251
Leu Arg Thr Pro Pro Arg Pro Val Ser Ser
                405                 410 gctgccccag cccagggcac gcccctggcc ccttgctgtt cccaagtgca cgatgctgct       1311
gtgactgagg agtggatgat gctcgtgtgt cctctgcaag cccctgctg tggcttgggt        1371 gggtaccggt tatgtgtccc tctgagtgtg tcttgagcgt gtccaccttc tccctctcca      1431
ctcccagaag accaaactgc cttcccctca gggctcaaga atgtgtacag tctgtggggc      1491
cggtgtgaac ccactatttt gtgtccttga dacatttgtg ttgtggttcc ttgtccttgt      1551
ccctggcgtt aactgtccac tgcaagagtc tggctctccc ttctctgtga cccggcatga     1611
ctgggcgcct ggagcagttt cactctgtga ggagtgaggg aaccctgggg ctcaccctct      1671
cagaggaagg gcacagagag gaagggaaga attgggggc agccggagtg agtggcagcc       1731
tccctgcttc cttctgcatt cccaagccgg cagctactgc ccagggcccg cagtgttggc     1791
tgctgcctgc cacagcctct gtgactgcag tggagcggcg aattccctgt ggcctgccac      1851
gccttcggca tcagaggatg gagtggtcga ggctagtgga gtcccaggga ccgctggctg     1911
ctctgcctga gcatcaggga gggggcagga aagaccaagc tgggtttgca catctgtctg     1971
caggctgtct ctccaggcac ggggtgtcag gagggagaga cagcctgggt atgggcaaga    2031
aatgactgta aatatttcag ccccacatta tttatagaaa atgtacagtt gtgtgaatgt    2091
gaaataaatg tcctcacctc ccaaaaaaaa aaaaaaaaa aaaaaaaaa aaaaaaaaa        2151 aaaaaaa                                                                2158
```

```
<210> SEQ ID NO 2
<211> LENGTH: 410
<212> TYPE: PRT
<213> ORGANISM: Homo sapiens

<400> SEQUENCE: 2

Ser Asn Ala Gly Asp Gly Pro Gly Gly Glu Gly Ser Val His Leu Ala
 1               5                  10                  15

Ser Ser Arg Gly Thr Leu Ser Asp Ser Glu Ile Glu Thr Asn Ser Ala
            20                  25                  30

Thr Ser Thr Ile Phe Gly Lys Ala His Ser Leu Lys Pro Ser Ile Lys
        35                  40                  45

Glu Lys Leu Ala Gly Ser Pro Ile Arg Thr Ser Glu Asp Val Ser Gln
50                  55                  60

Arg Val Tyr Leu Tyr Glu Gly Leu Leu Gly Lys Glu Arg Ser Thr Leu
65                  70                  75                  80

Trp Asp Gln Met Gln Phe Trp Glu Asp Ala Phe Leu Asp Ala Val Met
                85                  90                  95

Leu Glu Arg Glu Gly Met Gly Met Asp Gln Gly Pro Gln Glu Met Ile
            100                 105                 110

Asp Arg Tyr Leu Ser Leu Gly Glu His Asp Arg Lys Arg Leu Glu Asp
        115                 120                 125

Asp Glu Asp Arg Leu Leu Ala Thr Leu Leu His Asn Leu Ile Ser Tyr
130                 135                 140

Met Leu Leu Met Lys Val Asn Lys Asn Asp Ile Arg Lys Lys Val Arg
145                 150                 155                 160

Arg Leu Met Gly Lys Ser His Ile Gly Leu Val Tyr Ser Gln Gln Ile
                165                 170                 175

Asn Glu Val Leu Asp Gln Leu Ala Asn Leu Asn Gly Arg Asp Leu Ser
            180                 185                 190

Ile Trp Ser Ser Gly Ser Arg His Met Lys Lys Gln Thr Phe Val Val
        195                 200                 205

His Ala Gly Thr Asp Thr Asn Gly Asp Ile Phe Phe Met Glu Val Cys
210                 215                 220

Asp Asp Cys Val Val Leu Arg Ser Asn Ile Gly Thr Val Tyr Glu Arg
225                 230                 235                 240

Trp Trp Tyr Glu Lys Leu Ile Asn Met Thr Tyr Cys Pro Lys Thr Lys
                245                 250                 255

Val Leu Cys Leu Trp Arg Arg Asn Gly Ser Glu Thr Gln Leu Asn Lys
            260                 265                 270

Phe Tyr Thr Lys Lys Cys Arg Glu Leu Tyr Tyr Cys Val Lys Asp Ser
        275                 280                 285

Met Glu Arg Ala Ala Ala Arg Gln Gln Ser Ile Lys Pro Gly Pro Glu
290                 295                 300

Leu Gly Gly Glu Phe Pro Val Gln Asp Leu Lys Thr Gly Glu Gly Gly
305                 310                 315                 320

Leu Leu Gln Val Thr Leu Glu Gly Ile Asn Leu Lys Phe Met His Asn
                325                 330                 335

Gln Val Phe Ile Glu Leu Asn His Ile Lys Lys Cys Asn Thr Val Arg
            340                 345                 350

Gly Val Phe Val Leu Glu Glu Phe Val Pro Glu Ile Lys Glu Val Val
        355                 360                 365

Ser His Lys Tyr Lys Thr Pro Met Ala His Glu Ile Cys Tyr Ser Val
370                 375                 380
```

```
Leu Cys Leu Phe Ser Tyr Val Ala Ala Val His Ser Glu Glu Asp
385                 390                 395                 400

Leu Arg Thr Pro Pro Arg Pro Val Ser Ser
                405                 410

<210> SEQ ID NO 3
<211> LENGTH: 826
<212> TYPE: DNA
<213> ORGANISM: Homo sapiens
<220> FEATURE:
<221> NAME/KEY: CDS
<222> LOCATION: (2)..(415)

<400> SEQUENCE: 3 g gag gtg cag gac ctc ttc gaa gcc cag ggc aat gac cga ctg aag ctg       49
  Glu Val Gln Asp Leu Phe Glu Ala Gln Gly Asn Asp Arg Leu Lys Leu
  1               5                   10                  15 ctg gtg ctg tac agt gga gag gat gat gag ctg cta cag cgg gca gct        97
Leu Val Leu Tyr Ser Gly Glu Asp Asp Glu Leu Leu Gln Arg Ala Ala
            20                  25                  30 gcc ggg ggc ttg gcc atg ctt acc tcc atg cgg ccc acg ctc tgc agc       145
Ala Gly Gly Leu Ala Met Leu Thr Ser Met Arg Pro Thr Leu Cys Ser
        35                  40                  45 cgc att ccc caa gtg acc aca cac tgg ctg gag atc ctg cag gcc ctg       193
Arg Ile Pro Gln Val Thr Thr His Trp Leu Glu Ile Leu Gln Ala Leu
    50                  55                  60 ctt ctg agc tcc aac cag gag ctg cag cac cgg ggt gct gtg gtg gtg       241
Leu Leu Ser Ser Asn Gln Glu Leu Gln His Arg Gly Ala Val Val Val
65                  70                  75                  80 ctg aac atg gtg gag gcc tcg agg gag att gcc agc acc ctg atg gag       289
Leu Asn Met Val Glu Ala Ser Arg Glu Ile Ala Ser Thr Leu Met Glu
                85                  90                  95 agt gag atg atg gag atc ttg tca gtg cta gct aag ggt gac cac agc       337
Ser Glu Met Met Glu Ile Leu Ser Val Leu Ala Lys Gly Asp His Ser
            100                 105                 110 cct gtc aca agg gct gct gca gcc tgc ctg gac aaa gca gtg gaa tat       385
Pro Val Thr Arg Ala Ala Ala Ala Cys Leu Asp Lys Ala Val Glu Tyr
        115                 120                 125 ggg ctt atc caa ccc aac caa gat gga gag tgagggggtt gtccctgggc         435
Gly Leu Ile Gln Pro Asn Gln Asp Gly Glu
    130                 135 ccaaggctca tgcacacgct acctattgtg gcacggagag taaggacgga agcagctttg     495
gctggtggtg gctggcatgc ccaatactct tgcccatcct cgcttgctgc cctaggatgt     555
cctctgttct gagtcagcgg ccacgttcag tcacacagcc ctgcttggcc agcactgcct     615
gcagcctcac tcagaggggc ccttttctg tactactgta gtcagctggg aatggggaag      675
gtgcatccca acacagcctg tggatcctgg ggcatttgga agggcgcaca catcagcagc     735
ctcaccagct gtgagcctgc tatcaggcct gcccctccaa taaagtgtg tagaactcca      795 aaaaaaaaaa aaaaaaaaa aaaaaaaaa a                                      826

<210> SEQ ID NO 4
<211> LENGTH: 138
<212> TYPE: PRT
<213> ORGANISM: Homo sapiens

<400> SEQUENCE: 4

Glu Val Gln Asp Leu Phe Glu Ala Gln Gly Asn Asp Arg Leu Lys Leu
1               5                   10                  15
```

-continued

```
Leu Val Leu Tyr Ser Gly Glu Asp Asp Glu Leu Leu Gln Arg Ala Ala
             20                  25                  30

Ala Gly Gly Leu Ala Met Leu Thr Ser Met Arg Pro Thr Leu Cys Ser
         35                  40                  45

Arg Ile Pro Gln Val Thr Thr His Trp Leu Glu Ile Leu Gln Ala Leu
     50                  55                  60

Leu Leu Ser Ser Asn Gln Glu Leu Gln His Arg Gly Ala Val Val Val
 65                  70                  75                  80

Leu Asn Met Val Glu Ala Ser Arg Glu Ile Ala Ser Thr Leu Met Glu
                 85                  90                  95

Ser Glu Met Met Glu Ile Leu Ser Val Leu Ala Lys Gly Asp His Ser
            100                 105                 110

Pro Val Thr Arg Ala Ala Ala Cys Leu Asp Lys Ala Val Glu Tyr
        115                 120                 125

Gly Leu Ile Gln Pro Asn Gln Asp Gly Glu
    130                 135
```

<210> SEQ ID NO 5
<211> LENGTH: 722
<212> TYPE: DNA
<213> ORGANISM: Homo sapiens
<220> FEATURE:
<221> NAME/KEY: CDS
<222> LOCATION: (2)..(559)

<400> SEQUENCE: 5

```
g gag aag ccg ctg cac gcc ctg ctg cac ggc cgc ggg gtt tgc ctc aac      49
  Glu Lys Pro Leu His Ala Leu Leu His Gly Arg Gly Val Cys Leu Asn
   1               5                  10                  15 gaa aag agc tac cgc gag caa gtc aag atc gag aga gac tcc cgt gag        97
Glu Lys Ser Tyr Arg Glu Gln Val Lys Ile Glu Arg Asp Ser Arg Glu
                 20                  25                  30 cac gag gag ccc acc acc tct gag atg gcc gag gag acc tac tcc ccc       145
His Glu Glu Pro Thr Thr Ser Glu Met Ala Glu Glu Thr Tyr Ser Pro
         35                  40                  45 aag atc ttc cgg ccc aaa cac acc cgc atc tcc gag ctg aag gct gaa       193
Lys Ile Phe Arg Pro Lys His Thr Arg Ile Ser Glu Leu Lys Ala Glu
     50                  55                  60 gca gtg aag aag gac cgc aga aag aag ctg acc cag tcc aag ttt gtc       241
Ala Val Lys Lys Asp Arg Arg Lys Lys Leu Thr Gln Ser Lys Phe Val
 65                  70                  75                  80 ggg gga gcc gag aac act gcc cac ccc cgg atc atc tct gaa cct gag       289
Gly Gly Ala Glu Asn Thr Ala His Pro Arg Ile Ile Ser Glu Pro Glu
                 85                  90                  95 atg aga cag gag tct gag cag ggc ccc tgc cgc aga cac atg gag gct       337
Met Arg Gln Glu Ser Glu Gln Gly Pro Cys Arg Arg His Met Glu Ala
            100                 105                 110 tcc ctg cag gag ctc aaa gcc agc cca cgc atg gtg ccc cgt gct gtg       385
Ser Leu Gln Glu Leu Lys Ala Ser Pro Arg Met Val Pro Arg Ala Val
        115                 120                 125 tac ctg ccc aat tgt gac cgc aaa gga ttc tac aag aga aag cag tgc       433
Tyr Leu Pro Asn Cys Asp Arg Lys Gly Phe Tyr Lys Arg Lys Gln Cys
    130                 135                 140 aaa cct tcc cgt ggc cgc aag cgt ggc atc tgc tgg tgc gtg gac aag       481
Lys Pro Ser Arg Gly Arg Lys Arg Gly Ile Cys Trp Cys Val Asp Lys
145                 150                 155                 160 tac ggg atg aag ctg cca ggc atg gag tac gtt gac ggg gac ttt cag       529
Tyr Gly Met Lys Leu Pro Gly Met Glu Tyr Val Asp Gly Asp Phe Gln
                165                 170                 175
```

-continued

```
tgc cac acc ttc gac agc agc aac gtt gag tgatgcgtcc ccccccaacc      579
Cys His Thr Phe Asp Ser Ser Asn Val Glu
            180                 185 tttccctcac ccccttccac ccccagcccc gactccagcc agcgcctccc tccacccag    639 gacgccactc atttcatctc atttaaggga aaaatatata tctatctatt tgaggaaaaa   699
aaaaaaaaaa aaaaaaaaaa aaa                                          722
```

<210> SEQ ID NO 6
<211> LENGTH: 186
<212> TYPE: PRT
<213> ORGANISM: Homo sapiens

<400> SEQUENCE: 6

```
Glu Lys Pro Leu His Ala Leu Leu His Gly Arg Gly Val Cys Leu Asn
 1               5                  10                  15

Glu Lys Ser Tyr Arg Glu Gln Val Lys Ile Glu Arg Asp Ser Arg Glu
            20                  25                  30

His Glu Glu Pro Thr Thr Ser Glu Met Ala Glu Glu Thr Tyr Ser Pro
        35                  40                  45

Lys Ile Phe Arg Pro Lys His Thr Arg Ile Ser Glu Leu Lys Ala Glu
    50                  55                  60

Ala Val Lys Lys Asp Arg Arg Lys Leu Thr Gln Ser Lys Phe Val
65                  70                  75                  80

Gly Gly Ala Glu Asn Thr Ala His Pro Arg Ile Ile Ser Glu Pro Glu
                85                  90                  95

Met Arg Gln Glu Ser Glu Gln Gly Pro Cys Arg Arg His Met Glu Ala
            100                 105                 110

Ser Leu Gln Glu Leu Lys Ala Ser Pro Arg Met Val Pro Arg Ala Val
        115                 120                 125

Tyr Leu Pro Asn Cys Asp Arg Lys Gly Phe Tyr Lys Arg Lys Gln Cys
    130                 135                 140

Lys Pro Ser Arg Gly Arg Lys Arg Gly Ile Cys Trp Cys Val Asp Lys
145                 150                 155                 160

Tyr Gly Met Lys Leu Pro Gly Met Glu Tyr Val Asp Gly Asp Phe Gln
                165                 170                 175

Cys His Thr Phe Asp Ser Ser Asn Val Glu
            180                 185
```

<210> SEQ ID NO 7
<211> LENGTH: 1023
<212> TYPE: DNA
<213> ORGANISM: Homo sapiens
<220> FEATURE:
<221> NAME/KEY: CDS
<222> LOCATION: (57)..(872)

<400> SEQUENCE: 7

```
ccctgcactc tcgctctcct gccccacccc gaggtaaagg gggcgactaa gagaag atg    59
                                                               Met
                                                                1 gtg ttg ctc acc gcg gtc ctc ctg ctg ctg gcc gcc tat gcg ggg ccg    107
Val Leu Leu Thr Ala Val Leu Leu Leu Leu Ala Ala Tyr Ala Gly Pro
         5                  10                  15 gcc cag agc ctg ggc tcc ttc gtg cac tgc gag ccc tgc gac gag aaa    155
Ala Gln Ser Leu Gly Ser Phe Val His Cys Glu Pro Cys Asp Glu Lys
        20                  25                  30
```

```
gcc ctc tcc atg tgc ccc ccc agc ccc ctg ggc tgc gag ctg gtc aag        203
Ala Leu Ser Met Cys Pro Pro Ser Pro Leu Gly Cys Glu Leu Val Lys
 35                  40                  45 gag ccg ggc tgc ggc tgc tgc atg acc tgc gcc ctg gcc gag ggg cag        251
Glu Pro Gly Cys Gly Cys Cys Met Thr Cys Ala Leu Ala Glu Gly Gln
 50                  55                  60                  65 tcg tgc ggc gtc tac acc gag cgc tgc gcc cag ggg ctg cgc tgc ctc        299
Ser Cys Gly Val Tyr Thr Glu Arg Cys Ala Gln Gly Leu Arg Cys Leu
                 70                  75                  80 ccc cgg cag gac gag gag aag ccg ctg cac gcc ctg ctg cac ggc cgc        347
Pro Arg Gln Asp Glu Glu Lys Pro Leu His Ala Leu Leu His Gly Arg
             85                  90                  95 ggg gtt tgc ctc aac gaa aag agc tac cgc gag caa gtc aag atc gag        395
Gly Val Cys Leu Asn Glu Lys Ser Tyr Arg Glu Gln Val Lys Ile Glu
        100                 105                 110 aga gac tcc cgt gag cac gag gag ccc acc acc tct gag atg gcc gag        443
Arg Asp Ser Arg Glu His Glu Glu Pro Thr Thr Ser Glu Met Ala Glu
    115                 120                 125 gag acc tac tcc ccc aag atc ttc cgg ccc aaa cac acc cgc atc tcc        491
Glu Thr Tyr Ser Pro Lys Ile Phe Arg Pro Lys His Thr Arg Ile Ser
130                 135                 140                 145 gag ctg aag gct gaa gca gtg aag aag gac cgc aga aag aag ctg acc        539
Glu Leu Lys Ala Glu Ala Val Lys Lys Asp Arg Arg Lys Lys Leu Thr
                150                 155                 160 cag tcc aag ttt gtc ggg gga gcc gag aac act gcc cac ccc cgg atc        587
Gln Ser Lys Phe Val Gly Gly Ala Glu Asn Thr Ala His Pro Arg Ile
            165                 170                 175 atc tct gca cct gag atg aga cag gag tct gag cag ggc ccc tgc cgc        635
Ile Ser Ala Pro Glu Met Arg Gln Glu Ser Glu Gln Gly Pro Cys Arg
        180                 185                 190 aga cac atg gag gct tcc ctg cag gag ctc aaa gcc agc cca cgc atg        683
Arg His Met Glu Ala Ser Leu Gln Glu Leu Lys Ala Ser Pro Arg Met
    195                 200                 205 gtg ccc cgt gct gtg tac ctg ccc aat tgt gac cgc aaa gga ttc tac        731
Val Pro Arg Ala Val Tyr Leu Pro Asn Cys Asp Arg Lys Gly Phe Tyr
210                 215                 220                 225 aag aga aag cag tgc aaa cct tcc cgt ggc cgc aag cgt ggc atc tgc        779
Lys Arg Lys Gln Cys Lys Pro Ser Arg Gly Arg Lys Arg Gly Ile Cys
                230                 235                 240 tgg tgc gtg gac aag tac ggg atg aag ctg cca ggc atg gag tac gtt        827
Trp Cys Val Asp Lys Tyr Gly Met Lys Leu Pro Gly Met Glu Tyr Val
            245                 250                 255 gac ggg gac ttt cag tgc cac acc ttc gac agc agc aac gtt gag            872
Asp Gly Asp Phe Gln Cys His Thr Phe Asp Ser Ser Asn Val Glu
        260                 265                 270 tgatgcgtcc ccccccaacc tttccctcac cccctcccac ccccagcccc gactccagcc     932
agcgcctccc tccaccccag gacgccactc atttcatctc atttaaggga aaaatatata     992
tctatctatt tgaaaaaaaa aaaaaaaacc c                                    1023

<210> SEQ ID NO 8
<211> LENGTH: 272
<212> TYPE: PRT
<213> ORGANISM: Homo sapiens

<400> SEQUENCE: 8

Met Val Leu Leu Thr Ala Val Leu Leu Leu Leu Ala Ala Tyr Ala Gly
 1               5                  10                  15

Pro Ala Gln Ser Leu Gly Ser Phe Val His Cys Glu Pro Cys Asp Glu
            20                  25                  30
```

-continued

```
Lys Ala Leu Ser Met Cys Pro Pro Ser Pro Leu Gly Cys Glu Leu Val
         35                  40                  45

Lys Glu Pro Gly Cys Gly Cys Met Thr Cys Ala Leu Ala Glu Gly
 50                  55                  60

Gln Ser Cys Gly Val Tyr Thr Glu Arg Cys Ala Gln Gly Leu Arg Cys
 65                  70                  75                  80

Leu Pro Arg Gln Asp Glu Glu Lys Pro Leu His Ala Leu Leu His Gly
                 85                  90                  95

Arg Gly Val Cys Leu Asn Glu Lys Ser Tyr Arg Glu Gln Val Lys Ile
            100                 105                 110

Glu Arg Asp Ser Arg Glu His Glu Glu Pro Thr Thr Ser Glu Met Ala
        115                 120                 125

Glu Glu Thr Tyr Ser Pro Lys Ile Phe Arg Pro Lys His Thr Arg Ile
    130                 135                 140

Ser Glu Leu Lys Ala Glu Ala Val Lys Lys Asp Arg Arg Lys Lys Leu
145                 150                 155                 160

Thr Gln Ser Lys Phe Val Gly Gly Ala Glu Asn Thr Ala His Pro Arg
                165                 170                 175

Ile Ile Ser Ala Pro Glu Met Arg Gln Glu Ser Glu Gln Gly Pro Cys
            180                 185                 190

Arg Arg His Met Glu Ala Ser Leu Gln Glu Leu Lys Ala Ser Pro Arg
        195                 200                 205

Met Val Pro Arg Ala Val Tyr Leu Pro Asn Cys Asp Arg Lys Gly Phe
    210                 215                 220

Tyr Lys Arg Lys Gln Cys Lys Pro Ser Arg Gly Arg Lys Arg Gly Ile
225                 230                 235                 240

Cys Trp Cys Val Asp Lys Tyr Gly Met Lys Leu Pro Gly Met Glu Tyr
                245                 250                 255

Val Asp Gly Asp Phe Gln Cys His Thr Phe Asp Ser Ser Asn Val Glu
            260                 265                 270

<210> SEQ ID NO 9
<211> LENGTH: 1694
<212> TYPE: DNA
<213> ORGANISM: Homo sapiens
<220> FEATURE:
<221> NAME/KEY: CDS
<222> LOCATION: (2)..(931)

<400> SEQUENCE: 9 c tct ctc aag gcc aac atc cct gag gtg gaa gct gtc ctc aac acc gac      49
  Ser Leu Lys Ala Asn Ile Pro Glu Val Glu Ala Val Leu Asn Thr Asp
   1               5                  10                  15 agg agt ttg gtg tgt gat ggg aag agg ggc tta tta act cgt ctg ctg       97
Arg Ser Leu Val Cys Asp Gly Lys Arg Gly Leu Leu Thr Arg Leu Leu
             20                  25                  30 cag gtc atg aag aag gag cca gca gag tcg tct ttc agg ttt tgg caa      145
Gln Val Met Lys Lys Glu Pro Ala Glu Ser Ser Phe Arg Phe Trp Gln
         35                  40                  45 gct cgg gct gtg gag agt ttc ctc cga ggg acc acc tcc tat gca gac      193
Ala Arg Ala Val Glu Ser Phe Leu Arg Gly Thr Thr Ser Tyr Ala Asp
     50                  55                  60 cag atg ttc ctg ctg aag cga ggc ctc ttg gag cac atc ctt tac tgc      241
Gln Met Phe Leu Leu Lys Arg Gly Leu Leu Glu His Ile Leu Tyr Cys
 65                  70                  75                  80 att gtg gac agc gag tgt aag tca agg gat gtg ctc cag agt tac ttt      289
Ile Val Asp Ser Glu Cys Lys Ser Arg Asp Val Leu Gln Ser Tyr Phe
                 85                  90                  95
```

```
gac ctc ctg ggg gag ctg atg aag ttc aac gtt gat gca ttc aag aga        337
Asp Leu Leu Gly Glu Leu Met Lys Phe Asn Val Asp Ala Phe Lys Arg
            100                 105                 110 ttc aat aaa tat atc aac acc gat gca aag ttc cag gta ttc ctg aag        385
Phe Asn Lys Tyr Ile Asn Thr Asp Ala Lys Phe Gln Val Phe Leu Lys
                115                 120                 125 cag atc aac agc tcc ctg gtg gac tcc aac atg ctg gtg cgc tgt gtc        433
Gln Ile Asn Ser Ser Leu Val Asp Ser Asn Met Leu Val Arg Cys Val
130                 135                 140 act ctg tcc ctg gac cga ttt gaa aac cag gtg gat atg aaa gtt gcc        481
Thr Leu Ser Leu Asp Arg Phe Glu Asn Gln Val Asp Met Lys Val Ala
145                 150                 155                 160 gag gta ctg tct gaa tgc cgc ctg ctc gcc tac ata tcc cag gtg ccc        529
Glu Val Leu Ser Glu Cys Arg Leu Leu Ala Tyr Ile Ser Gln Val Pro
                165                 170                 175 acg cag atg tcc ttc ctc ttc cgc ctc atc aac atc atc cac gtg cag        577
Thr Gln Met Ser Phe Leu Phe Arg Leu Ile Asn Ile Ile His Val Gln
            180                 185                 190 acg ctg acc cag gag aac gtc agc tgc ctc aac acc agc ctg gtg atc        625
Thr Leu Thr Gln Glu Asn Val Ser Cys Leu Asn Thr Ser Leu Val Ile
        195                 200                 205 ctg atg ctg gcc cga cgg aaa gag cgg ctg ccc ctg tac ctg cgg ctg        673
Leu Met Leu Ala Arg Arg Lys Glu Arg Leu Pro Leu Tyr Leu Arg Leu
    210                 215                 220 ctg cag cgg atg gag cac agc aag aag tac ccc ggc ttc ctg ctc aac        721
Leu Gln Arg Met Glu His Ser Lys Lys Tyr Pro Gly Phe Leu Leu Asn
225                 230                 235                 240 aac ttc cac aac ctg ctg cgc ttc tgg cag cag cac tac ctg cac aag        769
Asn Phe His Asn Leu Leu Arg Phe Trp Gln Gln His Tyr Leu His Lys
                245                 250                 255 gac aag gac agc acc tgc cta gag aac agc tcc tgc atc agc ttc tca        817
Asp Lys Asp Ser Thr Cys Leu Glu Asn Ser Ser Cys Ile Ser Phe Ser
            260                 265                 270 tac tgg aag gag aca gtg tcc atc ctg ttg aac ccg gac cgg cag tca        865
Tyr Trp Lys Glu Thr Val Ser Ile Leu Leu Asn Pro Asp Arg Gln Ser
        275                 280                 285 ccc tct gct ctc gtt agc tac att gag gag ccc tac atg gac ata gac        913
Pro Ser Ala Leu Val Ser Tyr Ile Glu Glu Pro Tyr Met Asp Ile Asp
    290                 295                 300 agg gac ttc act gag gag tgaccttggg ccaggcctcg ggaggctgct              961
Arg Asp Phe Thr Glu Glu
305                 310 gggccagtgt gggtgagcgt gggtacgatg ccacacgccc tgccctgttc ccgttcctcc     1021
ctgctgctct ctgcctgccc caggtctttg ggtacaggct tggtgggagg gaagtcctag     1081
aagcccttgg tccccctggg tctgagggcc ctaggtcatg gagagcctca gtccccataa     1141
tgaggacagg gtaccatgcc cacctttcct tcagaaccct ggggcccagg ccacccaga     1201 ggtaagagga catttagcat tagctctgtg tgagctcctg ccggtttctt ggctgtcagt     1261
cagtcccaga gtggggagga agatatgggt gaccccacc cccatctgt gagccaagcc      1321 tcccttgtcc ctgccttttg gacccaggca aaggcttctg agccctgggc aggggtggtg    1381
ggtaccagag aatgctgcct tcccccaagc ctgcccctct gcctcatttt cctgtagctc    1441
ctctggttct gtttgctcat tggccgctgt gttcatccaa gggggttctc ccagaagtga    1501
ggggcctttc cctccatccc ttggggcacg ggcagctgt gcctgccctg cctctgcctg    1561
aggcagccgc tcctgcctga gcctggacat ggggcccttc cttgtgttgc caatttatta    1621
```

```
acagcaaata aaccaattaa atgcagacta ttaaataact ttattttaaa aatgaaaaaa    1681
aaaaaaaaaa aaa                                                      1694
```

<210> SEQ ID NO 10
<211> LENGTH: 310
<212> TYPE: PRT
<213> ORGANISM: Homo sapiens

<400> SEQUENCE: 10

```
Ser Leu Lys Ala Asn Ile Pro Glu Val Glu Ala Val Leu Asn Thr Asp
  1               5                  10                  15

Arg Ser Leu Val Cys Asp Gly Lys Gly Leu Leu Thr Arg Leu Leu
             20                  25                  30

Gln Val Met Lys Lys Glu Pro Ala Glu Ser Ser Phe Arg Phe Trp Gln
         35                  40                  45

Ala Arg Ala Val Glu Ser Phe Leu Arg Gly Thr Thr Ser Tyr Ala Asp
     50                  55                  60

Gln Met Phe Leu Leu Lys Arg Gly Leu Leu Glu His Ile Leu Tyr Cys
 65                  70                  75                  80

Ile Val Asp Ser Glu Cys Lys Ser Arg Asp Val Leu Gln Ser Tyr Phe
                 85                  90                  95

Asp Leu Leu Gly Glu Leu Met Lys Phe Asn Val Asp Ala Phe Lys Arg
                100                 105                 110

Phe Asn Lys Tyr Ile Asn Thr Asp Ala Lys Phe Gln Val Phe Leu Lys
            115                 120                 125

Gln Ile Asn Ser Ser Leu Val Asp Ser Asn Met Leu Val Arg Cys Val
        130                 135                 140

Thr Leu Ser Leu Asp Arg Phe Glu Asn Gln Val Asp Met Lys Val Ala
145                 150                 155                 160

Glu Val Leu Ser Glu Cys Arg Leu Leu Ala Tyr Ile Ser Gln Val Pro
                165                 170                 175

Thr Gln Met Ser Phe Leu Phe Arg Leu Ile Asn Ile Ile His Val Gln
            180                 185                 190

Thr Leu Thr Gln Glu Asn Val Ser Cys Leu Asn Thr Ser Leu Val Ile
        195                 200                 205

Leu Met Leu Ala Arg Arg Lys Glu Arg Leu Pro Leu Tyr Leu Arg Leu
    210                 215                 220

Leu Gln Arg Met Glu His Ser Lys Lys Tyr Pro Gly Phe Leu Leu Asn
225                 230                 235                 240

Asn Phe His Asn Leu Leu Arg Phe Trp Gln Gln His Tyr Leu His Lys
                245                 250                 255

Asp Lys Asp Ser Thr Cys Leu Glu Asn Ser Ser Cys Ile Ser Phe Ser
            260                 265                 270

Tyr Trp Lys Glu Thr Val Ser Ile Leu Leu Asn Pro Asp Arg Gln Ser
        275                 280                 285

Pro Ser Ala Leu Val Ser Tyr Ile Glu Glu Pro Tyr Met Asp Ile Asp
    290                 295                 300

Arg Asp Phe Thr Glu Glu
305                 310
```

<210> SEQ ID NO 11
<211> LENGTH: 2735
<212> TYPE: DNA
<213> ORGANISM: Homo sapiens

```
<220> FEATURE:
<221> NAME/KEY: CDS
<222> LOCATION: (2)..(1822)

<400> SEQUENCE: 11 g gag atc agt cgg aag gtg tac aag gga atg tta gac ctc ctc aag tgt      49
  Glu Ile Ser Arg Lys Val Tyr Lys Gly Met Leu Asp Leu Leu Lys Cys
    1               5                  10                  15 aca gtc ctc agc ttg gag cag tcc tat gcc cac gcg ggt ctg ggt ggc        97
Thr Val Leu Ser Leu Glu Gln Ser Tyr Ala His Ala Gly Leu Gly Gly
                20                  25                  30 atg gcc agc atc ttt ggg ctt ttg gag att gcc cag acc cac tac tat       145
Met Ala Ser Ile Phe Gly Leu Leu Glu Ile Ala Gln Thr His Tyr Tyr
             35                  40                  45 agt aaa gaa cca gac aag cgg aag aga agt cca aca gaa agt gta aat       193
Ser Lys Glu Pro Asp Lys Arg Lys Arg Ser Pro Thr Glu Ser Val Asn
     50                  55                  60 acc cca gtt ggc aag gat cct ggc cta gct ggg cgg ggg gac cca aag       241
Thr Pro Val Gly Lys Asp Pro Gly Leu Ala Gly Arg Gly Asp Pro Lys
 65                  70                  75                  80 gct atg gca caa ctg aga gtt cca caa ctg gga cct cgg gca cca agt       289
Ala Met Ala Gln Leu Arg Val Pro Gln Leu Gly Pro Arg Ala Pro Ser
                 85                  90                  95 gcc aca gga aag ggt cct aag gaa ctg gac acc aga agt tta aag gaa       337
Ala Thr Gly Lys Gly Pro Lys Glu Leu Asp Thr Arg Ser Leu Lys Glu
            100                 105                 110 gaa aat ttt ata gca tct att ggg cct gaa gta atc aaa cct gtc ttt       385
Glu Asn Phe Ile Ala Ser Ile Gly Pro Glu Val Ile Lys Pro Val Phe
        115                 120                 125 gac ctt ggt gag aca gag gag aaa aag tcc cag atc agc gca gac agt       433
Asp Leu Gly Glu Thr Glu Glu Lys Lys Ser Gln Ile Ser Ala Asp Ser
    130                 135                 140 ggt gtg agc ctg acg tct agt tcc cag agg act gat caa gac tct gtc       481
Gly Val Ser Leu Thr Ser Ser Ser Gln Arg Thr Asp Gln Asp Ser Val
145                 150                 155                 160 atc ggc gtg agt cca gct gtt atg atc cgc agc tca agt cag gat tct       529
Ile Gly Val Ser Pro Ala Val Met Ile Arg Ser Ser Ser Gln Asp Ser
                165                 170                 175 gaa gtt agc acc gtg gtg agt aat agc tct gga gag acc ctt gga gct       577
Glu Val Ser Thr Val Val Ser Asn Ser Ser Gly Glu Thr Leu Gly Ala
            180                 185                 190 gac agt gac ttg agc agc aat gca ggt gat gga cca ggt ggc gag ggc       625
Asp Ser Asp Leu Ser Ser Asn Ala Gly Asp Gly Pro Gly Gly Glu Gly
        195                 200                 205 agt gtt cac ctg gca agc tct cgg ggc act ttg tct gat agt gaa att       673
Ser Val His Leu Ala Ser Ser Arg Gly Thr Leu Ser Asp Ser Glu Ile
    210                 215                 220 gag acc aac tct gcc aca agc acc atc ttt ggt aaa gcc cac agc ttg       721
Glu Thr Asn Ser Ala Thr Ser Thr Ile Phe Gly Lys Ala His Ser Leu
225                 230                 235                 240 aag cca agc ata aag gag aag ctg gca ggc agc ccc att cgt act tct       769
Lys Pro Ser Ile Lys Glu Lys Leu Ala Gly Ser Pro Ile Arg Thr Ser
                245                 250                 255 gaa gat gtg agc cag cga gtc tat ctc tat gag gga ctc cta ggc aaa       817
Glu Asp Val Ser Gln Arg Val Tyr Leu Tyr Glu Gly Leu Leu Gly Lys
            260                 265                 270 gag cgt tct act tta tgg gac caa atg caa ttc tgg gaa gat gcc ttc       865
Glu Arg Ser Thr Leu Trp Asp Gln Met Gln Phe Trp Glu Asp Ala Phe
        275                 280                 285
```

-continued

| | | |
|---|---|---|
| tta gat gct gtg atg ttg gag aga gaa ggg atg ggt atg gac cag ggt<br>Leu Asp Ala Val Met Leu Glu Arg Glu Gly Met Gly Met Asp Gln Gly<br>290                           295                       300 | | 913 |
| ccc cag gaa atg atc gac agg tac ctg tcc ctt gga gaa cat gac cgg<br>Pro Gln Glu Met Ile Asp Arg Tyr Leu Ser Leu Gly Glu His Asp Arg<br>305                         310                       315                  320 | | 961 |
| aag cgc ctg gaa gat gat gaa gat cgc ttg ctg gcc aca ctt ctg cac<br>Lys Arg Leu Glu Asp Asp Glu Asp Arg Leu Leu Ala Thr Leu Leu His<br>                      325                       330                       335 | | 1009 |
| aac ctc atc tcc tac atg ctg ctg atg aag gta aat aag aat gac atc<br>Asn Leu Ile Ser Tyr Met Leu Leu Met Lys Val Asn Lys Asn Asp Ile<br>         340                       345                       350 | | 1057 |
| cgc aag aag gtg agg cgc cta atg gga aag tcg cac att ggg ctt gtg<br>Arg Lys Lys Val Arg Arg Leu Met Gly Lys Ser His Ile Gly Leu Val<br>355                         360                       365 | | 1105 |
| tac agc cag caa atc aat gag gtg ctt gat cag ctg gcg aac ctg aat<br>Tyr Ser Gln Gln Ile Asn Glu Val Leu Asp Gln Leu Ala Asn Leu Asn<br>         370                       375                       380 | | 1153 |
| gga cgc gat ctc tct atc tgg tcc agt ggc agc cgg cac atg aag aag<br>Gly Arg Asp Leu Ser Ile Trp Ser Ser Gly Ser Arg His Met Lys Lys<br>385                         390                       395                  400 | | 1201 |
| cag aca ttt gtg gta cat gca ggg aca gat aca aac gga gat atc ttt<br>Gln Thr Phe Val Val His Ala Gly Thr Asp Thr Asn Gly Asp Ile Phe<br>                         405                       410                       415 | | 1249 |
| ttc atg gag gtg tgc gat gac tgt gtg gtg ttg cgt agt aac atc gga<br>Phe Met Glu Val Cys Asp Asp Cys Val Val Leu Arg Ser Asn Ile Gly<br>                  420                       425                       430 | | 1297 |
| aca gtg tat gag cgc tgg tgg tac gag aag ctc atc aac atg acc tac<br>Thr Val Tyr Glu Arg Trp Trp Tyr Glu Lys Leu Ile Asn Met Thr Tyr<br>                       435                       440                       445 | | 1345 |
| tgt ccc aag acg aag gtg ttg tgc ttg tgg cgt aga aat ggc tct gag<br>Cys Pro Lys Thr Lys Val Leu Cys Leu Trp Arg Arg Asn Gly Ser Glu<br>450                         455                       460 | | 1393 |
| acc cag ctc aac aag ttc tat act aaa aag tgt cgg gag ctg tac tac<br>Thr Gln Leu Asn Lys Phe Tyr Thr Lys Lys Cys Arg Glu Leu Tyr Tyr<br>465                         470                       475                  480 | | 1441 |
| tgt gtg aag gac agc atg gag cgc gct gcc gcc cga cag caa agc atc<br>Cys Val Lys Asp Ser Met Glu Arg Ala Ala Ala Arg Gln Gln Ser Ile<br>                  485                       490                       495 | | 1489 |
| aaa ccc gga cct gaa ttg ggt ggc gag ttc cct gtg cag gac ctg aag<br>Lys Pro Gly Pro Glu Leu Gly Gly Glu Phe Pro Val Gln Asp Leu Lys<br>                      500                       505                       510 | | 1537 |
| act ggt gag ggt ggc ctg ctg cag gtg acc ctg gaa ggg atc aac ctc<br>Thr Gly Glu Gly Gly Leu Leu Gln Val Thr Leu Glu Gly Ile Asn Leu<br>              515                       520                       525 | | 1585 |
| aaa ttc atg cac aat cag gtt ttc ata gag ctg aat cac att aaa aag<br>Lys Phe Met His Asn Gln Val Phe Ile Glu Leu Asn His Ile Lys Lys<br>530                         535                       540 | | 1633 |
| tgc aat aca gtt cga ggc gtc ttt gtc ctg gag gaa ttt gtt cct gaa<br>Cys Asn Thr Val Arg Gly Val Phe Val Leu Glu Glu Phe Val Pro Glu<br>545                         550                       555                  560 | | 1681 |
| att aaa gaa gtg gtg agc cac aag tac aag aca cca atg gcc cac gaa<br>Ile Lys Glu Val Val Ser His Lys Tyr Lys Thr Pro Met Ala His Glu<br>                       565                       570                       575 | | 1729 |
| atc tgc tac tcc gta tta tgt ctc ttc tcg tac gtg gct gca gtt cat<br>Ile Cys Tyr Ser Val Leu Cys Leu Phe Ser Tyr Val Ala Ala Val His<br>         580                       585                       590 | | 1777 |
| agc agt gag gaa gat ctc aga acc ccg ccc cgg cct gtc tct agc<br>Ser Ser Glu Glu Asp Leu Arg Thr Pro Pro Arg Pro Val Ser Ser<br>595                         600                       605 | | 1822 |

-continued

```
tgatggagag gggctacgca gctgccccag cccagggcac gccccctggcc ccttgctgtt   1882 cccaagtgca cgatgctgct gtgactgagg agtggatgat gctcgtgtgt cctctgcaag   1942 cccccctgctg tggcttggtt ggttaccggt tatgtgtccc tctgagtgtg tcttgagcgt   2002
gtccaccttc tccctctcca ctcccagaag accaaactgc cttcccctca gggctcaaga   2062
atgtgtacag tctgtggggc cggtgtgaac ccactatttt gtgtccttga gacatttgtg   2122
ttgtggttcc ttgtccttgt ccctggcgtt ataactgtcc actgcaagag tctggctctc   2182
ccttctctgt gacccggcat gactgggcgc tggagcagt ttcactctgt gaggagtgag   2242
ggaaccctgg ggctcaccct ctcagaggaa gggcacagag aggaagggaa gaattggggg   2302
gcagccggag tgagtggcag cctccctgct tccttctgca ttcccaagcc ggcagctact   2362
gcccagggcc cgcagtgttg gctgctgcct gccacagcct ctgtgactgc agtggagcgg   2422
cgaattccct gtggcctgcc acgccttcgg catcagagga tggagtggtc gaggctagtg   2482
gagtcccagg gaccgctggc tgctctgcct gagcatcagg gagggggcag gaaagaccaa   2542
gctgggtttg cacatctgtc tgcaggctgt ctctccaggc acgggtgtc aggagggaga   2602 gacagcctgg gtatgggcaa gaaatgactg taaatatttc agccccacat tatttataga   2662
aaatgtacag ttgtgtgaat gtgaaataaa tgtcctcaac tcccaaaaaa aaaaaaaaa    2722 aaaaaaaaaa aaa                                                     2735
```

<210> SEQ ID NO 12
<211> LENGTH: 607
<212> TYPE: PRT
<213> ORGANISM: Homo sapiens

<400> SEQUENCE: 12

```
Glu Ile Ser Arg Lys Val Tyr Lys Gly Met Leu Asp Leu Leu Lys Cys
  1               5                  10                  15

Thr Val Leu Ser Leu Glu Gln Ser Tyr Ala His Ala Gly Leu Gly Gly
             20                  25                  30

Met Ala Ser Ile Phe Gly Leu Leu Glu Ile Ala Gln Thr His Tyr Tyr
         35                  40                  45

Ser Lys Glu Pro Asp Lys Arg Lys Arg Ser Pro Thr Glu Ser Val Asn
     50                  55                  60

Thr Pro Val Gly Lys Asp Pro Gly Leu Ala Gly Arg Gly Asp Pro Lys
 65                  70                  75                  80

Ala Met Ala Gln Leu Arg Val Pro Gln Leu Gly Pro Arg Ala Pro Ser
                 85                  90                  95

Ala Thr Gly Lys Gly Pro Lys Glu Leu Asp Thr Arg Ser Leu Lys Glu
            100                 105                 110

Glu Asn Phe Ile Ala Ser Ile Gly Pro Glu Val Ile Lys Pro Val Phe
        115                 120                 125

Asp Leu Gly Glu Thr Glu Lys Lys Ser Gln Ile Ser Ala Asp Ser
    130                 135                 140

Gly Val Ser Leu Thr Ser Ser Gln Arg Thr Asp Gln Asp Ser Val
145                 150                 155                 160

Ile Gly Val Ser Pro Ala Val Met Ile Arg Ser Ser Gln Asp Ser
                165                 170                 175

Glu Val Ser Thr Val Val Ser Asn Ser Ser Gly Glu Thr Leu Gly Ala
            180                 185                 190

Asp Ser Asp Leu Ser Ser Asn Ala Gly Asp Gly Pro Gly Gly Glu Gly
        195                 200                 205
```

```
Ser Val His Leu Ala Ser Ser Arg Gly Thr Leu Ser Asp Ser Glu Ile
    210                 215                 220

Glu Thr Asn Ser Ala Thr Ser Thr Ile Phe Gly Lys Ala His Ser Leu
225                 230                 235                 240

Lys Pro Ser Ile Lys Glu Lys Leu Ala Gly Ser Pro Ile Arg Thr Ser
                245                 250                 255

Glu Asp Val Ser Gln Arg Val Tyr Leu Tyr Glu Gly Leu Leu Gly Lys
                260                 265                 270

Glu Arg Ser Thr Leu Trp Asp Gln Met Gln Phe Trp Glu Asp Ala Phe
        275                 280                 285

Leu Asp Ala Val Met Leu Glu Arg Glu Gly Met Gly Met Asp Gln Gly
    290                 295                 300

Pro Gln Glu Met Ile Asp Arg Tyr Leu Ser Leu Gly Glu His Asp Arg
305                 310                 315                 320

Lys Arg Leu Glu Asp Asp Glu Asp Arg Leu Leu Ala Thr Leu Leu His
                325                 330                 335

Asn Leu Ile Ser Tyr Met Leu Leu Met Lys Val Asn Lys Asn Asp Ile
                340                 345                 350

Arg Lys Lys Val Arg Arg Leu Met Gly Lys Ser His Ile Gly Leu Val
        355                 360                 365

Tyr Ser Gln Gln Ile Asn Glu Val Leu Asp Gln Leu Ala Asn Leu Asn
370                 375                 380

Gly Arg Asp Leu Ser Ile Trp Ser Ser Gly Ser Arg His Met Lys Lys
385                 390                 395                 400

Gln Thr Phe Val Val His Ala Gly Thr Asp Thr Asn Gly Asp Ile Phe
                405                 410                 415

Phe Met Glu Val Cys Asp Asp Cys Val Val Leu Arg Ser Asn Ile Gly
                420                 425                 430

Thr Val Tyr Glu Arg Trp Trp Tyr Glu Lys Leu Ile Asn Met Thr Tyr
        435                 440                 445

Cys Pro Lys Thr Lys Val Leu Cys Leu Trp Arg Arg Asn Gly Ser Glu
450                 455                 460

Thr Gln Leu Asn Lys Phe Tyr Thr Lys Lys Cys Arg Glu Leu Tyr Tyr
465                 470                 475                 480

Cys Val Lys Asp Ser Met Glu Arg Ala Ala Ala Arg Gln Gln Ser Ile
                485                 490                 495

Lys Pro Gly Pro Glu Leu Gly Gly Glu Phe Pro Val Gln Asp Leu Lys
                500                 505                 510

Thr Gly Glu Gly Gly Leu Leu Gln Val Thr Leu Glu Gly Ile Asn Leu
        515                 520                 525

Lys Phe Met His Asn Gln Val Phe Ile Glu Leu Asn His Ile Lys Lys
530                 535                 540

Cys Asn Thr Val Arg Gly Val Phe Val Leu Glu Glu Phe Val Pro Glu
545                 550                 555                 560

Ile Lys Glu Val Val Ser His Lys Tyr Lys Thr Pro Met Ala His Glu
                565                 570                 575

Ile Cys Tyr Ser Val Leu Cys Leu Phe Ser Tyr Val Ala Ala Val His
                580                 585                 590

Ser Ser Glu Glu Asp Leu Arg Thr Pro Pro Arg Pro Val Ser Ser
        595                 600                 605

<210> SEQ ID NO 13
<211> LENGTH: 3225
<212> TYPE: DNA
```

-continued

```
<213> ORGANISM: Homo sapiens
<220> FEATURE:
<221> NAME/KEY: CDS
<222> LOCATION: (3)..(2846)

<400> SEQUENCE: 13 cc cag act cgc ccc gcc cca gag act gcg cct gcg cgg gca cga gac        47
   Gln Thr Arg Pro Ala Pro Glu Thr Ala Pro Ala Arg Ala Arg Asp
   1               5                  10                  15 acc ctc tcc gcg atg act gcc agc tca gtg gag cag ctg cgg aag gag       95
Thr Leu Ser Ala Met Thr Ala Ser Ser Val Glu Gln Leu Arg Lys Glu
                20                  25                  30 ggc aat gag ctg ttc aaa tgt gga gac tac ggg ggc gcc ctg gcg gcc      143
Gly Asn Glu Leu Phe Lys Cys Gly Asp Tyr Gly Gly Ala Leu Ala Ala
            35                  40                  45 tac act cag gcc ctg ggt ctg gac gcg acg ccc cag gac cag gcc gtt      191
Tyr Thr Gln Ala Leu Gly Leu Asp Ala Thr Pro Gln Asp Gln Ala Val
        50                  55                  60 ctg cac cgg aac cgg gcc gcc tgc cac ctc aag ctg gaa gat tac gac      239
Leu His Arg Asn Arg Ala Ala Cys His Leu Lys Leu Glu Asp Tyr Asp
    65                  70                  75 aaa gca gaa aca gag gca tcc aaa gcc att gaa aag gat ggt ggg gat      287
Lys Ala Glu Thr Glu Ala Ser Lys Ala Ile Glu Lys Asp Gly Gly Asp
80                  85                  90                  95 gtc aaa gca ctc tac cgg cgg agc caa gcc cta gag aag ctg ggc cgc      335
Val Lys Ala Leu Tyr Arg Arg Ser Gln Ala Leu Glu Lys Leu Gly Arg
                100                 105                 110 ctg gac cag gct gtc ctt gac ctg cag aga tgt gtg agc ttg gag ccc      383
Leu Asp Gln Ala Val Leu Asp Leu Gln Arg Cys Val Ser Leu Glu Pro
            115                 120                 125 aag aac aaa gtt ttc cag gag gcc ttg cgg aac atc ggg ggc cag att      431
Lys Asn Lys Val Phe Gln Glu Ala Leu Arg Asn Ile Gly Gly Gln Ile
        130                 135                 140 cag gag aag gtg cga tac atg tcc tcg acg gat gcc aaa gtg gaa cag      479
Gln Glu Lys Val Arg Tyr Met Ser Ser Thr Asp Ala Lys Val Glu Gln
    145                 150                 155 atg ttt cag ata ctg ttg gac cca gaa gag aag ggc act gag aaa aag      527
Met Phe Gln Ile Leu Leu Asp Pro Glu Glu Lys Gly Thr Glu Lys Lys
160                 165                 170                 175 caa aag gct tct cag aac ctg gtg gtg ctg gcc agg gag gat gct gga      575
Gln Lys Ala Ser Gln Asn Leu Val Val Leu Ala Arg Glu Asp Ala Gly
                180                 185                 190 gcg gag aag atc ttc cgg agt aat ggg gtt cag ctc ttg caa cgt tta      623
Ala Glu Lys Ile Phe Arg Ser Asn Gly Val Gln Leu Leu Gln Arg Leu
            195                 200                 205 ctg gac atg gga gag act gac ctc atg ctg gcg gct ctg cgt acg ctg      671
Leu Asp Met Gly Glu Thr Asp Leu Met Leu Ala Ala Leu Arg Thr Leu
        210                 215                 220 gtt ggc att tgc tct gag cat cag tca cgg aca gtg gca acc ctg agc      719
Val Gly Ile Cys Ser Glu His Gln Ser Arg Thr Val Ala Thr Leu Ser
    225                 230                 235 ata ctg gga act cgg cga gta gtc tcc atc ctg ggc gtg gaa agc cag      767
Ile Leu Gly Thr Arg Arg Val Val Ser Ile Leu Gly Val Glu Ser Gln
240                 245                 250                 255 gct gtg tcc ctg gct gcc tgc cac ctg ctg cag gtt atg ttt gat gcc      815
Ala Val Ser Leu Ala Ala Cys His Leu Leu Gln Val Met Phe Asp Ala
                260                 265                 270 ctc aag gaa ggt gtc aaa aaa ggc ttc cga ggc aaa gaa ggt gcc atc      863
Leu Lys Glu Gly Val Lys Lys Gly Phe Arg Gly Lys Glu Gly Ala Ile
            275                 280                 285
```

```
att gtg gat cct gcc cgg gag ctg aag gtc ctc atc agt aac ctc tta        911
Ile Val Asp Pro Ala Arg Glu Leu Lys Val Leu Ile Ser Asn Leu Leu
        290                 295                 300 gat ctg ctg aca gag gtg ggg gtc tct ggc caa ggc cga gac aat gcc        959
Asp Leu Leu Thr Glu Val Gly Val Ser Gly Gln Gly Arg Asp Asn Ala
305                 310                 315 ctg acc ctc ctg att aaa gcg gtg ccc cgg aag tct ctc aag gac ccc       1007
Leu Thr Leu Leu Ile Lys Ala Val Pro Arg Lys Ser Leu Lys Asp Pro
320                 325                 330                 335 aac aac agc ctc acc ctc tgg gtc atc gac caa ggt ctg aaa aag att       1055
Asn Asn Ser Leu Thr Leu Trp Val Ile Asp Gln Gly Leu Lys Lys Ile
            340                 345                 350 ttg gaa gtg ggg ggc tct cta cag gac cct cct ggg gag ctc gca gtg       1103
Leu Glu Val Gly Gly Ser Leu Gln Asp Pro Pro Gly Glu Leu Ala Val
        355                 360                 365 acc gca aac agc cgc atg agc gcc tct att ctc ctc agc aag ctc ttt       1151
Thr Ala Asn Ser Arg Met Ser Ala Ser Ile Leu Leu Ser Lys Leu Phe
370                 375                 380 gat gac ctc aag tgt gat gcg gag agg gag aat ttc cac aga ctt tgt       1199
Asp Asp Leu Lys Cys Asp Ala Glu Arg Glu Asn Phe His Arg Leu Cys
385                 390                 395 gaa aac tac atc aag agc tgg ttt gag ggc caa ggg ctg gcc ggg aag       1247
Glu Asn Tyr Ile Lys Ser Trp Phe Glu Gly Gln Gly Leu Ala Gly Lys
400                 405                 410                 415 cta cgg gcc atc cag acg gtg tcc tgc ctc ctg cag ggc cca tgt gac       1295
Leu Arg Ala Ile Gln Thr Val Ser Cys Leu Leu Gln Gly Pro Cys Asp
            420                 425                 430 gct ggc aac cgg gcc ttg gag ctg agc ggt gtc atg gag agt gtg att       1343
Ala Gly Asn Arg Ala Leu Glu Leu Ser Gly Val Met Glu Ser Val Ile
        435                 440                 445 gct ctg tgt gcc tct gag cag gag gag gag cag ctg gtg gcc gtg gag       1391
Ala Leu Cys Ala Ser Glu Gln Glu Glu Glu Gln Leu Val Ala Val Glu
450                 455                 460 gct ctg atc cat gca gcc ggc aag gct aag cgg gcc tca ttc atc act       1439
Ala Leu Ile His Ala Ala Gly Lys Ala Lys Arg Ala Ser Phe Ile Thr
465                 470                 475 gcc aat ggt gtc tcg ctg ctg aag gac cta tat aag tgc agc gag aag       1487
Ala Asn Gly Val Ser Leu Leu Lys Asp Leu Tyr Lys Cys Ser Glu Lys
480                 485                 490                 495 gac agc atc cgc atc cgg gcg cta gtg gga ctc tgt aag ctc ggt tcg       1535
Asp Ser Ile Arg Ile Arg Ala Leu Val Gly Leu Cys Lys Leu Gly Ser
            500                 505                 510 gct gga ggg act gac ttc agc atg aag cag ttt gct gaa ggc tcc act       1583
Ala Gly Gly Thr Asp Phe Ser Met Lys Gln Phe Ala Glu Gly Ser Thr
        515                 520                 525 ctc aaa ctg gct aag cag tgt cga aag tgg ctg tgc aat gac cag atc       1631
Leu Lys Leu Ala Lys Gln Cys Arg Lys Trp Leu Cys Asn Asp Gln Ile
530                 535                 540 gac gca ggc act cgg cgc tgg gca gtg gag ggc ctg gct tac ctg acc       1679
Asp Ala Gly Thr Arg Arg Trp Ala Val Glu Gly Leu Ala Tyr Leu Thr
545                 550                 555 ttt gat gcc gac gtg aag gaa gag ttt gtg gag gat gcg gct gct ctg       1727
Phe Asp Ala Asp Val Lys Glu Glu Phe Val Glu Asp Ala Ala Ala Leu
560                 565                 570                 575 aaa gct ctg ttc cag ctc agc agg ttg gag gag agg tca gtg ctc ttt       1775
Lys Ala Leu Phe Gln Leu Ser Arg Leu Glu Glu Arg Ser Val Leu Phe
            580                 585                 590 gcg gtg gcc tca gcg ctg gtg aac tgc acc aac agc tat gac tac gag       1823
Ala Val Ala Ser Ala Leu Val Asn Cys Thr Asn Ser Tyr Asp Tyr Glu
        595                 600                 605
```

-continued

| | |
|---|---|
| gag ccc gac ccc aag atg gtg gag ctg gcc aag tat gcc aag cag cat<br>Glu Pro Asp Pro Lys Met Val Glu Leu Ala Lys Tyr Ala Lys Gln His<br>610                     615                   620 | 1871 |
| gtg ccc gag cag cac ccc aag gac aag cca agc ttc gtg cgg gct cgg<br>Val Pro Glu Gln His Pro Lys Asp Lys Pro Ser Phe Val Arg Ala Arg<br>625                     630                   635 | 1919 |
| gtg aag aag ctg ctg gca gcg ggt gtg gtg tcg gcc atg gtg tgc atg<br>Val Lys Lys Leu Leu Ala Ala Gly Val Val Ser Ala Met Val Cys Met<br>640                     645                   650                 655 | 1967 |
| gtg aag acg gag agc cct gtg ctg acc agt tcc tgc aga gag ctg ctc<br>Val Lys Thr Glu Ser Pro Val Leu Thr Ser Ser Cys Arg Glu Leu Leu<br>660                     665                   670 | 2015 |
| tcc agg gtc ttc ttg gct tta gtg gaa gag gta gag gac cga ggc act<br>Ser Arg Val Phe Leu Ala Leu Val Glu Glu Val Glu Asp Arg Gly Thr<br>675                     680                   685 | 2063 |
| gtg gtt gcc cag gga ggc ggc agg gcg ctg atc ccg ctg gcc ctg gaa<br>Val Val Ala Gln Gly Gly Gly Arg Ala Leu Ile Pro Leu Ala Leu Glu<br>690                     695                   700 | 2111 |
| ggc acg gac gtg ggg cag aca aag gca gcc cag gcc ctt gcc aag ctc<br>Gly Thr Asp Val Gly Gln Thr Lys Ala Ala Gln Ala Leu Ala Lys Leu<br>705                     710                   715 | 2159 |
| acc atc acc tcc aac ccg gag atg acc ttc cct ggc gag cgg atc tat<br>Thr Ile Thr Ser Asn Pro Glu Met Thr Phe Pro Gly Glu Arg Ile Tyr<br>720                     725                   730                 735 | 2207 |
| gag gtg gtc cgg ccc ctc gtc tcc ctg ttg cac ctc aac tgc tca ggc<br>Glu Val Val Arg Pro Leu Val Ser Leu Leu His Leu Asn Cys Ser Gly<br>740                     745                   750 | 2255 |
| ctg cag aac ttc gag gcg ctc atg gcc cta aca aac ctg gct ggg atc<br>Leu Gln Asn Phe Glu Ala Leu Met Ala Leu Thr Asn Leu Ala Gly Ile<br>755                     760                   765 | 2303 |
| agc gag agg ctc cgg cag aag atc ctg aag gag aag gct gtg ccc atg<br>Ser Glu Arg Leu Arg Gln Lys Ile Leu Lys Glu Lys Ala Val Pro Met<br>770                     775                   780 | 2351 |
| ata gaa ggc tac atg ttt gag gag cat gag atg atc cgc cgg gca gcc<br>Ile Glu Gly Tyr Met Phe Glu Glu His Glu Met Ile Arg Arg Ala Ala<br>785                     790                   795 | 2399 |
| acg gag tgc atg tgt aac ttg gcc atg agc aag gag gtg cag gac ctc<br>Thr Glu Cys Met Cys Asn Leu Ala Met Ser Lys Glu Val Gln Asp Leu<br>800                     805                   810                 815 | 2447 |
| ttc gaa gcc cag ggc aat gac cga ctg aag ctg ctg gtg ctg tac agt<br>Phe Glu Ala Gln Gly Asn Asp Arg Leu Lys Leu Leu Val Leu Tyr Ser<br>820                     825                   830 | 2495 |
| gga gag gat gat gag ctg cta cag cgg gca gct gcc ggg ggc ttg gcc<br>Gly Glu Asp Asp Glu Leu Leu Gln Arg Ala Ala Ala Gly Gly Leu Ala<br>835                     840                   845 | 2543 |
| atg ctt acc tcc atg cgg ccc acg ctc tgc agc cgc att ccc caa gtg<br>Met Leu Thr Ser Met Arg Pro Thr Leu Cys Ser Arg Ile Pro Gln Val<br>850                     855                   860 | 2591 |
| acc aca cac tgg ctg gag atc ctg cag gcc ctg ctt ctg agc tcc aac<br>Thr Thr His Trp Leu Glu Ile Leu Gln Ala Leu Leu Leu Ser Ser Asn<br>865                     870                   875 | 2639 |
| cag gag ctg cag cac cgg ggt gct gtg gtg gtg ctg aac atg gtg gag<br>Gln Glu Leu Gln His Arg Gly Ala Val Val Val Leu Asn Met Val Glu<br>880                     885                   890                 895 | 2687 |
| gcc tcg agg gag att gcc agc acc ctg atg gag agt gag atg atg gag<br>Ala Ser Arg Glu Ile Ala Ser Thr Leu Met Glu Ser Glu Met Met Glu<br>900                     905                   910 | 2735 |
| atc ttg tca gtg cta gct aag ggt gac cac agc cct gtc aca agg gct<br>Ile Leu Ser Val Leu Ala Lys Gly Asp His Ser Pro Val Thr Arg Ala<br>915                     920                   925 | 2783 |

-continued

```
gct gca gcc tgc ctg gac aaa gca gtg gaa tat ggg ctt atc caa ccc     2831
Ala Ala Ala Cys Leu Asp Lys Ala Val Glu Tyr Gly Leu Ile Gln Pro
            930                 935                 940 aac caa gat gga gag tgagggggtt gtccctgggc ccaaggctca tgcacacgct     2886
Asn Gln Asp Gly Glu
    945 acctattgtg gcacggagag taaggacgga agcagctttg gctggtggtg gctggcatgc   2946 ccaatactct tgcccatcct cgcttgctgc cctaggatgt cctctgttct gagtcagcgg   3006 ccacgttcag tcacacagcc ctgcttggcc agcactgcct gcagcctcac tcagaggggc   3066 ccttttctg tactactgta gtcagctggg aatggggaag gtgcatccca acacagcctg    3126 tggatcctgg ggcatttgga agggcgcaca catcagcagc ctcaccagct gtgagcctgc   3186 tatcaggcct gcccctccaa taaaagtgtg tagaactcc                          3225
```

<210> SEQ ID NO 14
<211> LENGTH: 948
<212> TYPE: PRT
<213> ORGANISM: Homo sapiens

<400> SEQUENCE: 14

```
Gln Thr Arg Pro Ala Pro Glu Thr Ala Pro Ala Arg Ala Arg Asp Thr
  1               5                  10                  15

Leu Ser Ala Met Thr Ala Ser Ser Val Glu Gln Leu Arg Lys Glu Gly
             20                  25                  30

Asn Glu Leu Phe Lys Cys Gly Asp Tyr Gly Gly Ala Leu Ala Ala Tyr
         35                  40                  45

Thr Gln Ala Leu Gly Leu Asp Ala Thr Pro Gln Asp Gln Ala Val Leu
     50                  55                  60

His Arg Asn Arg Ala Ala Cys His Leu Lys Leu Glu Asp Tyr Asp Lys
 65                  70                  75                  80

Ala Glu Thr Glu Ala Ser Lys Ala Ile Glu Lys Asp Gly Gly Asp Val
                 85                  90                  95

Lys Ala Leu Tyr Arg Arg Ser Gln Ala Leu Glu Lys Leu Gly Arg Leu
            100                 105                 110

Asp Gln Ala Val Leu Asp Leu Gln Arg Cys Val Ser Leu Glu Pro Lys
        115                 120                 125

Asn Lys Val Phe Gln Glu Ala Leu Arg Asn Ile Gly Gly Gln Ile Gln
    130                 135                 140

Glu Lys Val Arg Tyr Met Ser Ser Thr Asp Ala Lys Val Glu Gln Met
145                 150                 155                 160

Phe Gln Ile Leu Leu Asp Pro Glu Glu Lys Gly Thr Glu Lys Lys Gln
                165                 170                 175

Lys Ala Ser Gln Asn Leu Val Val Leu Ala Arg Glu Asp Ala Gly Ala
            180                 185                 190

Glu Lys Ile Phe Arg Ser Asn Gly Val Gln Leu Leu Gln Arg Leu Leu
        195                 200                 205

Asp Met Gly Glu Thr Asp Leu Met Leu Ala Ala Leu Arg Thr Leu Val
    210                 215                 220

Gly Ile Cys Ser Glu His Gln Ser Arg Thr Val Ala Thr Leu Ser Ile
225                 230                 235                 240

Leu Gly Thr Arg Arg Val Val Ser Ile Leu Gly Val Glu Ser Gln Ala
                245                 250                 255

Val Ser Leu Ala Ala Cys His Leu Leu Gln Val Met Phe Asp Ala Leu
            260                 265                 270
```

```
Lys Glu Gly Val Lys Lys Gly Phe Arg Gly Lys Glu Gly Ala Ile Ile
            275                 280                 285

Val Asp Pro Ala Arg Glu Leu Lys Val Leu Ile Ser Asn Leu Leu Asp
        290                 295                 300

Leu Leu Thr Glu Val Gly Val Ser Gly Gln Gly Arg Asp Asn Ala Leu
305                 310                 315                 320

Thr Leu Leu Ile Lys Ala Val Pro Arg Lys Ser Leu Lys Asp Pro Asn
                325                 330                 335

Asn Ser Leu Thr Leu Trp Val Ile Asp Gln Gly Leu Lys Lys Ile Leu
            340                 345                 350

Glu Val Gly Gly Ser Leu Gln Asp Pro Pro Gly Glu Leu Ala Val Thr
        355                 360                 365

Ala Asn Ser Arg Met Ser Ala Ser Ile Leu Leu Ser Lys Leu Phe Asp
    370                 375                 380

Asp Leu Lys Cys Asp Ala Glu Arg Glu Asn Phe His Arg Leu Cys Glu
385                 390                 395                 400

Asn Tyr Ile Lys Ser Trp Phe Glu Gly Gln Gly Leu Ala Gly Lys Leu
                405                 410                 415

Arg Ala Ile Gln Thr Val Ser Cys Leu Leu Gln Gly Pro Cys Asp Ala
            420                 425                 430

Gly Asn Arg Ala Leu Glu Leu Ser Gly Val Met Glu Ser Val Ile Ala
        435                 440                 445

Leu Cys Ala Ser Glu Gln Glu Glu Gln Leu Val Ala Val Glu Ala
450                 455                 460

Leu Ile His Ala Ala Gly Lys Ala Lys Arg Ala Ser Phe Ile Thr Ala
465                 470                 475                 480

Asn Gly Val Ser Leu Leu Lys Asp Leu Tyr Lys Cys Ser Glu Lys Asp
                485                 490                 495

Ser Ile Arg Ile Arg Ala Leu Val Gly Leu Cys Lys Leu Gly Ser Ala
            500                 505                 510

Gly Gly Thr Asp Phe Ser Met Lys Gln Phe Ala Glu Gly Ser Thr Leu
        515                 520                 525

Lys Leu Ala Lys Gln Cys Arg Lys Trp Leu Cys Asn Asp Gln Ile Asp
    530                 535                 540

Ala Gly Thr Arg Arg Trp Ala Val Glu Gly Leu Ala Tyr Leu Thr Phe
545                 550                 555                 560

Asp Ala Asp Val Lys Glu Glu Phe Val Glu Asp Ala Ala Leu Lys
                565                 570                 575

Ala Leu Phe Gln Leu Ser Arg Leu Glu Glu Arg Ser Val Leu Phe Ala
            580                 585                 590

Val Ala Ser Ala Leu Val Asn Cys Thr Asn Ser Tyr Asp Tyr Glu Glu
        595                 600                 605

Pro Asp Pro Lys Met Val Glu Leu Ala Lys Tyr Ala Lys Gln His Val
    610                 615                 620

Pro Glu Gln His Pro Lys Asp Lys Pro Ser Phe Val Arg Ala Arg Val
625                 630                 635                 640

Lys Lys Leu Leu Ala Gly Val Val Ser Ala Met Val Cys Met Val
                645                 650                 655

Lys Thr Glu Ser Pro Val Leu Thr Ser Ser Cys Arg Glu Leu Leu Ser
            660                 665                 670

Arg Val Phe Leu Ala Leu Val Glu Glu Val Glu Asp Arg Gly Thr Val
        675                 680                 685
```

-continued

| | | | | | | | | | | | |
|---|---|---|---|---|---|---|---|---|---|---|---|
|Val|Ala|Gln|Gly|Gly|Arg|Ala|Leu|Ile|Pro|Leu|Ala|Leu|Glu|Gly|
| |690| | | |695| | | |700| | |

Thr Asp Val Gly Gln Thr Lys Ala Ala Gln Ala Leu Ala Lys Leu Thr
705                 710                 715                 720

Ile Thr Ser Asn Pro Glu Met Thr Phe Pro Gly Glu Arg Ile Tyr Glu
                725                 730                 735

Val Val Arg Pro Leu Val Ser Leu Leu His Leu Asn Cys Ser Gly Leu
        740                 745                 750

Gln Asn Phe Glu Ala Leu Met Ala Leu Thr Asn Leu Ala Gly Ile Ser
    755                 760                 765

Glu Arg Leu Arg Gln Lys Ile Leu Lys Glu Lys Ala Val Pro Met Ile
770                 775                 780

Glu Gly Tyr Met Phe Glu His Glu Met Ile Arg Arg Ala Ala Thr
785                 790                 795                 800

Glu Cys Met Cys Asn Leu Ala Met Ser Lys Glu Val Gln Asp Leu Phe
                805                 810                 815

Glu Ala Gln Gly Asn Asp Arg Leu Lys Leu Leu Val Leu Tyr Ser Gly
        820                 825                 830

Glu Asp Asp Glu Leu Leu Gln Arg Ala Ala Ala Gly Gly Leu Ala Met
    835                 840                 845

Leu Thr Ser Met Arg Pro Thr Leu Cys Ser Arg Ile Pro Gln Val Thr
850                 855                 860

Thr His Trp Leu Glu Ile Leu Gln Ala Leu Leu Leu Ser Ser Asn Gln
865                 870                 875                 880

Glu Leu Gln His Arg Gly Ala Val Val Leu Asn Met Val Glu Ala
                885                 890                 895

Ser Arg Glu Ile Ala Ser Thr Leu Met Glu Ser Glu Met Met Glu Ile
        900                 905                 910

Leu Ser Val Leu Ala Lys Gly Asp His Ser Pro Val Thr Arg Ala Ala
    915                 920                 925

Ala Ala Cys Leu Asp Lys Ala Val Glu Tyr Gly Leu Ile Gln Pro Asn
930                 935                 940

Gln Asp Gly Glu
945

<210> SEQ ID NO 15
<211> LENGTH: 6002
<212> TYPE: DNA
<213> ORGANISM: Homo sapiens
<220> FEATURE:
<221> NAME/KEY: CDS
<222> LOCATION: (326)..(5089)

<400> SEQUENCE: 15
cacgtgcatg tgtagcatgc cttggttttt cctttggcat ctgaaaaagg cacaacctga        60
aagacctaga acccagtgtc ggtccccagg cccttgggga caggaagaga agagccgtgt       120
ggccgcgggg aggatgtcct gcggcggggc tgtcctcgcg gactgactgg actccatctc       180
ccagcgggcg ccgcggcgcg gccacgcccc cccactcccc gcgcgcgccc ggtggagact       240
tcgattttca gaattcctcc tgggaatgct gactccttgc ttggtgccct gatgcttctc       300
tgagataaac tgatgaattg gaacc atg gtg caa aag aag aag ttc tgt cct        352
                            Met Val Gln Lys Lys Lys Phe Cys Pro
                              1               5 cgg tta ctt gac tat cta gtg atc gta ggg gcc agg cac ccg agc agt        400
Arg Leu Leu Asp Tyr Leu Val Ile Val Gly Ala Arg His Pro Ser Ser
 10              15                  20                  25

```
gat agc gtg gcc cag act cct gaa ttg cta cgg cga tac ccc ttg gag      448
Asp Ser Val Ala Gln Thr Pro Glu Leu Leu Arg Arg Tyr Pro Leu Glu
            30                  35                  40 gat cac act gag ttt ccc ctg ccc cca gat gta gtg ttc ttc tgc cag      496
Asp His Thr Glu Phe Pro Leu Pro Pro Asp Val Val Phe Phe Cys Gln
        45                  50                  55 ccc gag ggc tgc ctg agc gtg cgg cag cgg cgc atg agc ctt cgg gat      544
Pro Glu Gly Cys Leu Ser Val Arg Gln Arg Arg Met Ser Leu Arg Asp
                60                  65                  70 gat acc tct ttt gtc ttc acc ctc act gac aag gac act gga gtc acg      592
Asp Thr Ser Phe Val Phe Thr Leu Thr Asp Lys Asp Thr Gly Val Thr
    75                  80                  85 cga tat ggc atc tgt gtt aac ttc tac cgc tcc ttc caa aag cga atc      640
Arg Tyr Gly Ile Cys Val Asn Phe Tyr Arg Ser Phe Gln Lys Arg Ile
90                  95                  100                 105 tct aag gag aag ggg gaa ggt ggg gca ggg tcc cgt ggg aag gaa gga      688
Ser Lys Glu Lys Gly Glu Gly Gly Ala Gly Ser Arg Gly Lys Glu Gly
                    110                 115                 120 acc cat gcc acc tgt gcc tca gaa gag ggt ggc act gag agc tca gag      736
Thr His Ala Thr Cys Ala Ser Glu Glu Gly Gly Thr Glu Ser Ser Glu
        125                 130                 135 agt ggc tca tcc ctg cag cct ctc agt gct gac tct acc cct gat gtg      784
Ser Gly Ser Ser Leu Gln Pro Leu Ser Ala Asp Ser Thr Pro Asp Val
            140                 145                 150 aac cag tct cct cgg ggc aaa cgc cgg gcc aag gcg ggg agc cgc tcc      832
Asn Gln Ser Pro Arg Gly Lys Arg Arg Ala Lys Ala Gly Ser Arg Ser
                155                 160                 165 cgc aac agt act ctc acg tcc ctg tgc gtg ctc agc cac tac cct ttc      880
Arg Asn Ser Thr Leu Thr Ser Leu Cys Val Leu Ser His Tyr Pro Phe
170                 175                 180                 185 ttc tcc acc ttc cga gag tgt ttg tat act ctc aag cgc ctg gtg gac      928
Phe Ser Thr Phe Arg Glu Cys Leu Tyr Thr Leu Lys Arg Leu Val Asp
                    190                 195                 200 tgc tgt agt gag cgc ctt ctg ggc aag aaa ctg ggc atc cct cga ggc      976
Cys Cys Ser Glu Arg Leu Leu Gly Lys Lys Leu Gly Ile Pro Arg Gly
        205                 210                 215 gta caa agg gac acc atg tgg cgg atc ttt act gga tcg ctg ctg gta     1024
Val Gln Arg Asp Thr Met Trp Arg Ile Phe Thr Gly Ser Leu Leu Val
            220                 225                 230 gag gag aag tca agt gcc ctt ctg cat gac ctt cga gag att gag gcc     1072
Glu Glu Lys Ser Ser Ala Leu Leu His Asp Leu Arg Glu Ile Glu Ala
                235                 240                 245 tgg atc tat cga ttg ctg cgc tcc cca gta ccc gtc tct ggg cag aag     1120
Trp Ile Tyr Arg Leu Leu Arg Ser Pro Val Pro Val Ser Gly Gln Lys
250                 255                 260                 265 cga gta gac atc gag gtc cta ccc caa gag ctc cag cca gct ctg acc     1168
Arg Val Asp Ile Glu Val Leu Pro Gln Glu Leu Gln Pro Ala Leu Thr
                    270                 275                 280 ttt gct ctt cca gac cca tct cga ttc acc cta gtg gat ttc cca ctg     1216
Phe Ala Leu Pro Asp Pro Ser Arg Phe Thr Leu Val Asp Phe Pro Leu
        285                 290                 295 cac ctt ccc ttg gaa ctt cta ggt gtg gac gcc tgt ctc cag gtg cta     1264
His Leu Pro Leu Glu Leu Leu Gly Val Asp Ala Cys Leu Gln Val Leu
            300                 305                 310 acc tgc att ctg tta gag cac aag gtg gtg cta cag tcc cga gac tac     1312
Thr Cys Ile Leu Leu Glu His Lys Val Val Leu Gln Ser Arg Asp Tyr
                315                 320                 325 aat gca ctc tcc atg tct gtg atg gca ttc gtg gca atg atc tac cca     1360
Asn Ala Leu Ser Met Ser Val Met Ala Phe Val Ala Met Ile Tyr Pro
330                 335                 340                 345
```

```
ctg gaa tat atg ttt cct gtc atc ccg ctg cta ccc acc tgc atg gca       1408
Leu Glu Tyr Met Phe Pro Val Ile Pro Leu Leu Pro Thr Cys Met Ala
            350                 355                 360 tca gca gag cag ctg ctg ttg gct cca acc ccg tac atc att ggg gtt       1456
Ser Ala Glu Gln Leu Leu Leu Ala Pro Thr Pro Tyr Ile Ile Gly Val
        365                 370                 375 cct gcc agc ttc ttc ctc tac aaa ctg gac ttc aaa atg cct gat gat       1504
Pro Ala Ser Phe Phe Leu Tyr Lys Leu Asp Phe Lys Met Pro Asp Asp
                380                 385                 390 gta tgg cta gtg gat ctg gac agc aat agg gtg att gcc ccc acc aat       1552
Val Trp Leu Val Asp Leu Asp Ser Asn Arg Val Ile Ala Pro Thr Asn
395                 400                 405 gca gaa gtg ctg cct atc ctg cca gaa cca gaa tca cta gag ctg aaa       1600
Ala Glu Val Leu Pro Ile Leu Pro Glu Pro Glu Ser Leu Glu Leu Lys
410                 415                 420                 425 aag cat tta aag cag gcc ttg gcc agc atg agt ctc aac acc cag ccc       1648
Lys His Leu Lys Gln Ala Leu Ala Ser Met Ser Leu Asn Thr Gln Pro
                430                 435                 440 atc ctc aat ctg gag aaa ttt cat gag ggc cag gag atc ccc ctt ctc       1696
Ile Leu Asn Leu Glu Lys Phe His Glu Gly Gln Glu Ile Pro Leu Leu
                445                 450                 455 ttg gga agg cct tct aat gac ctg cag tcc aca ccg tcc act gaa ttc       1744
Leu Gly Arg Pro Ser Asn Asp Leu Gln Ser Thr Pro Ser Thr Glu Phe
            460                 465                 470 aac cca ctc atc tat ggc aat gat gtg gat tct gtg gat gtt gca acc       1792
Asn Pro Leu Ile Tyr Gly Asn Asp Val Asp Ser Val Asp Val Ala Thr
475                 480                 485 agg gtt gcc atg gta cgg ttc ttc aat tcc gcc aac gtg ctg cag gga       1840
Arg Val Ala Met Val Arg Phe Phe Asn Ser Ala Asn Val Leu Gln Gly
490                 495                 500                 505 ttt cag atg cac acg cgt acc ctg cgc ctc ttt cct cgg cct gtg gta       1888
Phe Gln Met His Thr Arg Thr Leu Arg Leu Phe Pro Arg Pro Val Val
                510                 515                 520 gct ttt caa gct ggc tcc ttt cta gcc tca cgt ccc cgg cag act cct       1936
Ala Phe Gln Ala Gly Ser Phe Leu Ala Ser Arg Pro Arg Gln Thr Pro
            525                 530                 535 ttt gcc gag aaa ttg gcc agg act cag gct gtg gag tac ttt ggg gaa       1984
Phe Ala Glu Lys Leu Ala Arg Thr Gln Ala Val Glu Tyr Phe Gly Glu
        540                 545                 550 tgg atc ctt aac ccc acc aac tat gcc ttt cag cga att cac aac aat       2032
Trp Ile Leu Asn Pro Thr Asn Tyr Ala Phe Gln Arg Ile His Asn Asn
555                 560                 565 atg ttt gat cca gcc ctg att ggt gac aag cca aag tgg tat gct cat       2080
Met Phe Asp Pro Ala Leu Ile Gly Asp Lys Pro Lys Trp Tyr Ala His
570                 575                 580                 585 cag ctg cag cct atc cac tat cgc gtc tat gac agc aat tcc cag ctg       2128
Gln Leu Gln Pro Ile His Tyr Arg Val Tyr Asp Ser Asn Ser Gln Leu
                590                 595                 600 gct gag gcc ctg agt gta cca cca gag cgg gac tct gac tcc gaa cct       2176
Ala Glu Ala Leu Ser Val Pro Pro Glu Arg Asp Ser Asp Ser Glu Pro
            605                 610                 615 act gat gat agt ggc agt gat agt atg gat tat gac gat tca agc tct       2224
Thr Asp Asp Ser Gly Ser Asp Ser Met Asp Tyr Asp Asp Ser Ser Ser
        620                 625                 630 tct tac tcc tcc ctt ggt gac ttt gtc agt gaa atg atg aaa tgt gac       2272
Ser Tyr Ser Ser Leu Gly Asp Phe Val Ser Glu Met Met Lys Cys Asp
635                 640                 645 att aat ggt gat act ccc aat gtg gac cct ctg aca cat gca gca ctg       2320
Ile Asn Gly Asp Thr Pro Asn Val Asp Pro Leu Thr His Ala Ala Leu
650                 655                 660                 665
```

| | |
|---|---|
| ggg gat gcc agc gag gtg gag att gac gag ctg cag aat cag aag gaa<br>Gly Asp Ala Ser Glu Val Glu Ile Asp Glu Leu Gln Asn Gln Lys Glu<br>670               675               680 | 2368 |
| gca gaa gag cct ggc cca gac agt gag aac tct cag gaa aac ccc cca<br>Ala Glu Glu Pro Gly Pro Asp Ser Glu Asn Ser Gln Glu Asn Pro Pro<br>685               690               695 | 2416 |
| ctg cgc tcc agc tct agc acc aca gcc agc agc agc ccc agc act gtc<br>Leu Arg Ser Ser Ser Ser Thr Thr Ala Ser Ser Ser Pro Ser Thr Val<br>700               705               710 | 2464 |
| atc cac gga gcc aac tct gaa cct gct gac tct acg gag atg gat gat<br>Ile His Gly Ala Asn Ser Glu Pro Ala Asp Ser Thr Glu Met Asp Asp<br>715               720               725 | 2512 |
| aag gca gca gta ggc gtc tcc aag ccc ctc cct tcc gtg cct ccc agc<br>Lys Ala Ala Val Gly Val Ser Lys Pro Leu Pro Ser Val Pro Pro Ser<br>730               735               740               745 | 2560 |
| att ggc aaa tcg aac atg gac aga cgt cag gca gaa att gga gag ggg<br>Ile Gly Lys Ser Asn Met Asp Arg Arg Gln Ala Glu Ile Gly Glu Gly<br>750               755               760 | 2608 |
| tca gtg cgc cgg cga atc tat gac aat cca tac ttc gag ccc caa tat<br>Ser Val Arg Arg Arg Ile Tyr Asp Asn Pro Tyr Phe Glu Pro Gln Tyr<br>765               770               775 | 2656 |
| ggc ttt ccc cct gag gaa gat gag gat gag cag ggg gaa agt tac act<br>Gly Phe Pro Pro Glu Glu Asp Glu Asp Glu Gln Gly Glu Ser Tyr Thr<br>780               785               790 | 2704 |
| ccc cga ttc agc caa cat gtc agt ggc aat cgg gct caa aag ctg ctg<br>Pro Arg Phe Ser Gln His Val Ser Gly Asn Arg Ala Gln Lys Leu Leu<br>795               800               805 | 2752 |
| cgg ccc aac agc ttg aga ctg gca agt gac tca gat gca gag tca gac<br>Arg Pro Asn Ser Leu Arg Leu Ala Ser Asp Ser Asp Ala Glu Ser Asp<br>810               815               820               825 | 2800 |
| tct cgg gca agc tct ccc aac tcc acc gtc tcc aac acc agc acc gag<br>Ser Arg Ala Ser Ser Pro Asn Ser Thr Val Ser Asn Thr Ser Thr Glu<br>830               835               840 | 2848 |
| ggc ttc ggg ggc atc atg tct ttt gcc agc agc ctc tat cgg aac cac<br>Gly Phe Gly Gly Ile Met Ser Phe Ala Ser Ser Leu Tyr Arg Asn His<br>845               850               855 | 2896 |
| agt acc agc ttc agt ctt tca aac ctc aca ctg ccc acc aaa ggt gcc<br>Ser Thr Ser Phe Ser Leu Ser Asn Leu Thr Leu Pro Thr Lys Gly Ala<br>860               865               870 | 2944 |
| cga gag aag gcc acg ccc ttc ccc agt ctg aaa gga aac agg agg gcg<br>Arg Glu Lys Ala Thr Pro Phe Pro Ser Leu Lys Gly Asn Arg Arg Ala<br>875               880               885 | 2992 |
| tta gtg gat cag aag tca tct gtc att aaa cac agc cca aca gtg aaa<br>Leu Val Asp Gln Lys Ser Ser Val Ile Lys His Ser Pro Thr Val Lys<br>890               895               900               905 | 3040 |
| aga gaa cct cca tca ccc cag ggt cga tcc agc aat tct agt gag aac<br>Arg Glu Pro Pro Ser Pro Gln Gly Arg Ser Ser Asn Ser Ser Glu Asn<br>910               915               920 | 3088 |
| cag cag ttc ctg aag gag gtg gtg cac agc gtg ctg gac ggc cag gga<br>Gln Gln Phe Leu Lys Glu Val Val His Ser Val Leu Asp Gly Gln Gly<br>925               930               935 | 3136 |
| gtt ggc tgg ctc aac atg aaa aag gtg cgc cgg ctg ctg gag agc gag<br>Val Gly Trp Leu Asn Met Lys Lys Val Arg Arg Leu Leu Glu Ser Glu<br>940               945               950 | 3184 |
| cag ctg cga gtc ttt gtc ctg agc aag ctg aac cgc atg gtg cag tca<br>Gln Leu Arg Val Phe Val Leu Ser Lys Leu Asn Arg Met Val Gln Ser<br>955               960               965 | 3232 |
| gag gac gat gcc cgg cag gac atc atc ccg gat gtg gag atc agt cgg<br>Glu Asp Asp Ala Arg Gln Asp Ile Ile Pro Asp Val Glu Ile Ser Arg<br>970               975               980               985 | 3280 |

-continued

| | |
|---|---|
| aag gtg tac aag gga atg tta gac ctc ctc aag tgt aca gtc ctc agc<br>Lys Val Tyr Lys Gly Met Leu Asp Leu Leu Lys Cys Thr Val Leu Ser<br>          990                995                1000 | 3328 |
| ttg gag cag tcc tat gcc cac gcg ggt ctg ggt ggc atg gcc agc atc<br>Leu Glu Gln Ser Tyr Ala His Ala Gly Leu Gly Gly Met Ala Ser Ile<br>          1005               1010               1015 | 3376 |
| ttt ggg ctt ttg gag att gcc cag acc cac tac tat agt aaa gaa cca<br>Phe Gly Leu Leu Glu Ile Ala Gln Thr His Tyr Tyr Ser Lys Glu Pro<br>      1020               1025               1030 | 3424 |
| gac aag cgg aag aga agt cca aca gaa agt gta aat acc cca gtt ggc<br>Asp Lys Arg Lys Arg Ser Pro Thr Glu Ser Val Asn Thr Pro Val Gly<br>          1035               1040               1045 | 3472 |
| aag gat cct ggc cta gct ggg cgg ggg gac cca aag gct atg gca caa<br>Lys Asp Pro Gly Leu Ala Gly Arg Gly Asp Pro Lys Ala Met Ala Gln<br>1050               1055               1060               1065 | 3520 |
| ctg aga gtt cca caa ctg gga cct cgg gca cca agt gcc aca gga aag<br>Leu Arg Val Pro Gln Leu Gly Pro Arg Ala Pro Ser Ala Thr Gly Lys<br>                1070               1075               1080 | 3568 |
| ggt cct aag gaa ctg gac acc aga agt tta aag gaa gaa aat ttt ata<br>Gly Pro Lys Glu Leu Asp Thr Arg Ser Leu Lys Glu Glu Asn Phe Ile<br>                   1085               1090               1095 | 3616 |
| gca tct att ggg cct gaa gta atc aaa cct gtc ttt gac ctt ggt gag<br>Ala Ser Ile Gly Pro Glu Val Ile Lys Pro Val Phe Asp Leu Gly Glu<br>          1100               1105               1110 | 3664 |
| aca gag gag aaa aag tcc cag atc agc gca gac agt ggt gtg agc ctg<br>Thr Glu Glu Lys Lys Ser Gln Ile Ser Ala Asp Ser Gly Val Ser Leu<br>                1115               1120               1125 | 3712 |
| acg tct agt tcc cag agg act gat caa gac tct gtc atc ggc gtg agt<br>Thr Ser Ser Ser Gln Arg Thr Asp Gln Asp Ser Val Ile Gly Val Ser<br>1130               1135               1140               1145 | 3760 |
| cca gct gtt atg atc cgc agc tca agt cag gat tct gaa gtt agc acc<br>Pro Ala Val Met Ile Arg Ser Ser Ser Gln Asp Ser Glu Val Ser Thr<br>                1150               1155               1160 | 3808 |
| gtg gtg agt aat agc tct gga gag acc ctt gga gct gac agt gac ttg<br>Val Val Ser Asn Ser Ser Gly Glu Thr Leu Gly Ala Asp Ser Asp Leu<br>          1165               1170               1175 | 3856 |
| agc agc aat gca ggt gat gga cca ggt ggc gag ggc agt gtt cac ctg<br>Ser Ser Asn Ala Gly Asp Gly Pro Gly Gly Glu Gly Ser Val His Leu<br>                1180               1185               1190 | 3904 |
| gca agc tct cgg ggc act ttg tct gat agt gaa att gag acc aac tct<br>Ala Ser Ser Arg Gly Thr Leu Ser Asp Ser Glu Ile Glu Thr Asn Ser<br>            1195               1200               1205 | 3952 |
| gcc aca agc acc atc ttt ggt aaa gcc cac agc ttg aag cca agc ata<br>Ala Thr Ser Thr Ile Phe Gly Lys Ala His Ser Leu Lys Pro Ser Ile<br>1210               1215               1220               1225 | 4000 |
| aag gag aag ctg gca ggc agc ccc att cgt act tct gaa gat gtg agc<br>Lys Glu Lys Leu Ala Gly Ser Pro Ile Arg Thr Ser Glu Asp Val Ser<br>                1230               1235               1240 | 4048 |
| cag cga gtc tat ctc tat gag gga ctc cta ggc aaa gag cgt tct act<br>Gln Arg Val Tyr Leu Tyr Glu Gly Leu Leu Gly Lys Glu Arg Ser Thr<br>                   1245               1250               1255 | 4096 |
| tta tgg gac caa atg caa ttc tgg gaa gat gcc ttc tta gat gct gtg<br>Leu Trp Asp Gln Met Gln Phe Trp Glu Asp Ala Phe Leu Asp Ala Val<br>          1260               1265               1270 | 4144 |
| atg ttg gag aga gaa ggg atg ggt atg gac cag ggt ccc cag gaa atg<br>Met Leu Glu Arg Glu Gly Met Gly Met Asp Gln Gly Pro Gln Glu Met<br>                1275               1280               1285 | 4192 |
| atc gac agg tac ctg tcc ctt gga gaa cat gac cgg aag cgc ctg gaa<br>Ile Asp Arg Tyr Leu Ser Leu Gly Glu His Asp Arg Lys Arg Leu Glu<br>1290               1295               1300               1305 | 4240 |

```
gat gat gaa gat cgc ttg ctg gcc aca ctt ctg cac aac ctc atc tcc    4288
Asp Asp Glu Asp Arg Leu Leu Ala Thr Leu Leu His Asn Leu Ile Ser
            1310                1315                1320 tac atg ctg ctg atg aag gta aat aag aat gac atc cgc aag aag gtg    4336
Tyr Met Leu Leu Met Lys Val Asn Lys Asn Asp Ile Arg Lys Lys Val
1325                1330                1335 agg cgc cta atg gga aag tcg cac att ggg ctt gtg tac agc cag caa    4384
Arg Arg Leu Met Gly Lys Ser His Ile Gly Leu Val Tyr Ser Gln Gln
        1340                1345                1350 atc aat gag gtg ctt gat cag ctg gcg aac ctg aat gga cgc gat ctc    4432
Ile Asn Glu Val Leu Asp Gln Leu Ala Asn Leu Asn Gly Arg Asp Leu
    1355                1360                1365 tct atc tgg tcc agt ggc agc cgg cac atg aag aag cag aca ttt gtg    4480
Ser Ile Trp Ser Ser Gly Ser Arg His Met Lys Lys Gln Thr Phe Val
1370                1375                1380                1385 gta cat gca ggg aca gat aca aac gga gat atc ttt ttc atg gag gtg    4528
Val His Ala Gly Thr Asp Thr Asn Gly Asp Ile Phe Phe Met Glu Val
        1390                1395                1400 tgc gat gac tgt gtg gtg ttg cgt agt aac atc gga aca gtg tat gag    4576
Cys Asp Asp Cys Val Val Leu Arg Ser Asn Ile Gly Thr Val Tyr Glu
    1405                1410                1415 cgc tgg tgg tac gag aag ctc atc aac atg acc tac tgt ccc aag acg    4624
Arg Trp Trp Tyr Glu Lys Leu Ile Asn Met Thr Tyr Cys Pro Lys Thr
        1420                1425                1430 aag gtg ttg tgc ttg tgg cgt aga aat ggc tct gag acc cag ctc aac    4672
Lys Val Leu Cys Leu Trp Arg Arg Asn Gly Ser Glu Thr Gln Leu Asn
1435                1440                1445 aag ttc tat act aaa aag tgt cgg gag ctg tac tac tgt gtg aag gac    4720
Lys Phe Tyr Thr Lys Lys Cys Arg Glu Leu Tyr Tyr Cys Val Lys Asp
1450                1455                1460                1465 agc atg gag cgc gct gcc gcc cga cag caa agc atc aaa ccc gga cct    4768
Ser Met Glu Arg Ala Ala Ala Arg Gln Gln Ser Ile Lys Pro Gly Pro
        1470                1475                1480 gaa ttg ggt ggc gag ttc cct gtg cag gac ctg aag act ggt gag ggt    4816
Glu Leu Gly Gly Glu Phe Pro Val Gln Asp Leu Lys Thr Gly Glu Gly
    1485                1490                1495 ggc ctg ctg cag gtg acc ctg gaa ggg atc aac ctc aaa ttc atg cac    4864
Gly Leu Leu Gln Val Thr Leu Glu Gly Ile Asn Leu Lys Phe Met His
        1500                1505                1510 aat cag gtt ttc ata gag ctg aat cac att aaa aag tgc aat aca gtt    4912
Asn Gln Val Phe Ile Glu Leu Asn His Ile Lys Lys Cys Asn Thr Val
    1515                1520                1525 cga ggc gtc ttt gtc ctg gag gaa ttt gtt cct gaa att aaa gaa gtg    4960
Arg Gly Val Phe Val Leu Glu Glu Phe Val Pro Glu Ile Lys Glu Val
1530                1535                1540                1545 gtg agc cac aag tac aag aca cca atg gcc cac gaa atc tgc tac tcc    5008
Val Ser His Lys Tyr Lys Thr Pro Met Ala His Glu Ile Cys Tyr Ser
        1550                1555                1560 gta tta tgt ctc ttc tcg tac gtg gct gca gtt cat agc agt gag gaa    5056
Val Leu Cys Leu Phe Ser Tyr Val Ala Ala Val His Ser Ser Glu Glu
        1565                1570                1575 gat ctc aga acc ccg ccc cgg cct gtc tct agc tgatggagag gggctacgca    5109
Asp Leu Arg Thr Pro Pro Arg Pro Val Ser Ser
        1580                1585 gctgccccag cccagggcac gcccctggcc ccttgctgtt cccaagtgca cgatgctgct    5169
gtgactgagg agtggatgat gctcgtgtgt cctctgcaag cccctgctg tggcttggtt     5229 ggttaccggt tatgtgtccc tctgagtgtg tcttgagcgt gtccaccttc tccctctcca    5289
ctcccagaag accaaactgc cttcccctca gggctcaaga atgtgtacag tctgtggggc    5349
```

-continued

```
cggtgtgaac ccactatttt gtgtccttga cacatttgtg ttgtggttcc ttgtccttgt    5409
ccctggcgtt ataactgtcc actgcaagag tctggctctc ccttctctgt gacccggcat    5469
gactgggcgc ctggagcagt ttcactctgt gaggagtgag ggaaccctgg ggctcaccct    5529
ctcagaggaa gggcacagag aggaagggaa gaattggggg gcagccggag tgagtggcag    5589
cctccctgct tccttctgca ttcccaagcc ggcagctact gcccagggcc cgcagtgttg    5649
gctgctgcct gccacagcct ctgtgactgc agtggagcgg cgaattccct gtggcctgcc    5709
acgccttcgg catcagagga tggagtggtc gaggctagtg gagtcccagg accgctggc    5769 tgctctgcct gagcatcagg gaggggggcag gaaagaccaa gctgggtttg cacatctgtc    5829
tgcaggctgt ctccaggc acggggtgtc aggagggaga gacagcctgg gtatgggcaa    5889
gaaatgactg taaatatttc agccccacat tatttataga aaatgtacag ttgtgtgaat    5949
gtgaaataaa tgtcctcaac tcccaaaaaa aaaaaaaaaa aaaaaaaaaa aaa           6002
```

<210> SEQ ID NO 16
<211> LENGTH: 1588
<212> TYPE: PRT
<213> ORGANISM: Homo sapiens

<400> SEQUENCE: 16

```
Met Val Gln Lys Lys Phe Cys Pro Arg Leu Leu Asp Tyr Leu Val
 1               5                  10                  15

Ile Val Gly Ala Arg His Pro Ser Ser Asp Ser Val Ala Gln Thr Pro
                20                  25                  30

Glu Leu Leu Arg Arg Tyr Pro Leu Glu Asp His Thr Glu Phe Pro Leu
            35                  40                  45

Pro Pro Asp Val Val Phe Phe Cys Gln Pro Glu Gly Cys Leu Ser Val
        50                  55                  60

Arg Gln Arg Arg Met Ser Leu Arg Asp Asp Thr Ser Phe Val Phe Thr
    65                  70                  75                  80

Leu Thr Asp Lys Asp Thr Gly Val Thr Arg Tyr Gly Ile Cys Val Asn
                85                  90                  95

Phe Tyr Arg Ser Phe Gln Lys Arg Ile Ser Lys Glu Lys Gly Glu Gly
                100                 105                 110

Gly Ala Gly Ser Arg Gly Lys Glu Gly Thr His Ala Thr Cys Ala Ser
            115                 120                 125

Glu Glu Gly Gly Thr Glu Ser Ser Glu Ser Gly Ser Ser Leu Gln Pro
        130                 135                 140

Leu Ser Ala Asp Ser Thr Pro Asp Val Asn Gln Ser Pro Arg Gly Lys
145                 150                 155                 160

Arg Arg Ala Lys Ala Gly Ser Arg Ser Arg Asn Ser Thr Leu Thr Ser
                165                 170                 175

Leu Cys Val Leu Ser His Tyr Pro Phe Phe Ser Thr Phe Arg Glu Cys
                180                 185                 190

Leu Tyr Thr Leu Lys Arg Leu Val Asp Cys Cys Ser Glu Arg Leu Leu
            195                 200                 205

Gly Lys Lys Leu Gly Ile Pro Arg Gly Val Gln Arg Asp Thr Met Trp
        210                 215                 220

Arg Ile Phe Thr Gly Ser Leu Leu Val Glu Glu Lys Ser Ser Ala Leu
225                 230                 235                 240

Leu His Asp Leu Arg Glu Ile Glu Ala Trp Ile Tyr Arg Leu Leu Arg
                245                 250                 255
```

```
Ser Pro Val Pro Val Ser Gly Gln Lys Arg Val Asp Ile Glu Val Leu
        260                 265                 270

Pro Gln Glu Leu Gln Pro Ala Leu Thr Phe Ala Leu Pro Asp Pro Ser
            275                 280                 285

Arg Phe Thr Leu Val Asp Phe Pro Leu His Leu Pro Leu Glu Leu Leu
        290                 295                 300

Gly Val Asp Ala Cys Leu Gln Val Leu Thr Cys Ile Leu Leu Glu His
305                 310                 315                 320

Lys Val Val Leu Gln Ser Arg Asp Tyr Asn Ala Leu Ser Met Ser Val
                325                 330                 335

Met Ala Phe Val Ala Met Ile Tyr Pro Leu Glu Tyr Met Phe Pro Val
            340                 345                 350

Ile Pro Leu Leu Pro Thr Cys Met Ala Ser Ala Glu Gln Leu Leu Leu
        355                 360                 365

Ala Pro Thr Pro Tyr Ile Ile Gly Val Pro Ala Ser Phe Phe Leu Tyr
    370                 375                 380

Lys Leu Asp Phe Lys Met Pro Asp Asp Val Trp Leu Val Asp Leu Asp
385                 390                 395                 400

Ser Asn Arg Val Ile Ala Pro Thr Asn Ala Glu Val Leu Pro Ile Leu
                405                 410                 415

Pro Glu Pro Glu Ser Leu Glu Leu Lys Lys His Leu Lys Gln Ala Leu
            420                 425                 430

Ala Ser Met Ser Leu Asn Thr Gln Pro Ile Leu Asn Leu Glu Lys Phe
        435                 440                 445

His Glu Gly Gln Glu Ile Pro Leu Leu Leu Gly Arg Pro Ser Asn Asp
    450                 455                 460

Leu Gln Ser Thr Pro Ser Thr Glu Phe Asn Pro Leu Ile Tyr Gly Asn
465                 470                 475                 480

Asp Val Asp Ser Val Asp Val Ala Thr Arg Val Ala Met Val Arg Phe
                485                 490                 495

Phe Asn Ser Ala Asn Val Leu Gln Gly Phe Gln Met His Thr Arg Thr
            500                 505                 510

Leu Arg Leu Phe Pro Arg Pro Val Val Ala Phe Gln Ala Gly Ser Phe
        515                 520                 525

Leu Ala Ser Arg Pro Arg Gln Thr Pro Phe Ala Glu Lys Leu Ala Arg
    530                 535                 540

Thr Gln Ala Val Glu Tyr Phe Gly Glu Trp Ile Leu Asn Pro Thr Asn
545                 550                 555                 560

Tyr Ala Phe Gln Arg Ile His Asn Asn Met Phe Asp Pro Ala Leu Ile
                565                 570                 575

Gly Asp Lys Pro Lys Trp Tyr Ala His Gln Leu Gln Pro Ile His Tyr
            580                 585                 590

Arg Val Tyr Asp Ser Asn Ser Gln Leu Ala Glu Ala Leu Ser Val Pro
        595                 600                 605

Pro Glu Arg Asp Ser Asp Ser Glu Pro Thr Asp Asp Ser Gly Ser Asp
    610                 615                 620

Ser Met Asp Tyr Asp Asp Ser Ser Ser Tyr Ser Ser Leu Gly Asp
625                 630                 635                 640

Phe Val Ser Glu Met Met Lys Cys Asp Ile Asn Gly Asp Thr Pro Asn
                645                 650                 655

Val Asp Pro Leu Thr His Ala Ala Leu Gly Asp Ala Ser Glu Val Glu
            660                 665                 670
```

-continued

```
Ile Asp Glu Leu Gln Asn Gln Lys Glu Ala Glu Pro Gly Pro Asp
        675                 680                 685

Ser Glu Asn Ser Gln Glu Asn Pro Pro Leu Arg Ser Ser Ser Thr
    690                 695                 700

Thr Ala Ser Ser Ser Pro Ser Thr Val Ile His Gly Ala Asn Ser Glu
705                 710                 715                 720

Pro Ala Asp Ser Thr Glu Met Asp Asp Lys Ala Ala Val Gly Val Ser
                725                 730                 735

Lys Pro Leu Pro Ser Val Pro Pro Ser Ile Gly Lys Ser Asn Met Asp
                740                 745                 750

Arg Arg Gln Ala Glu Ile Gly Glu Gly Ser Val Arg Arg Arg Ile Tyr
            755                 760                 765

Asp Asn Pro Tyr Phe Glu Pro Gln Tyr Gly Phe Pro Pro Glu Glu Asp
    770                 775                 780

Glu Asp Glu Gln Gly Glu Ser Tyr Thr Pro Arg Phe Ser Gln His Val
785                 790                 795                 800

Ser Gly Asn Arg Ala Gln Lys Leu Leu Arg Pro Asn Ser Leu Arg Leu
                805                 810                 815

Ala Ser Asp Ser Asp Ala Glu Ser Asp Ser Arg Ala Ser Ser Pro Asn
            820                 825                 830

Ser Thr Val Ser Asn Thr Ser Thr Glu Gly Phe Gly Gly Ile Met Ser
        835                 840                 845

Phe Ala Ser Ser Leu Tyr Arg Asn His Ser Thr Ser Phe Ser Leu Ser
    850                 855                 860

Asn Leu Thr Leu Pro Thr Lys Gly Ala Arg Glu Lys Ala Thr Pro Phe
865                 870                 875                 880

Pro Ser Leu Lys Gly Asn Arg Arg Ala Leu Val Asp Gln Lys Ser Ser
                885                 890                 895

Val Ile Lys His Ser Pro Thr Val Lys Arg Glu Pro Pro Ser Pro Gln
            900                 905                 910

Gly Arg Ser Ser Asn Ser Ser Glu Asn Gln Gln Phe Leu Lys Glu Val
            915                 920                 925

Val His Ser Val Leu Asp Gly Gln Gly Val Gly Trp Leu Asn Met Lys
    930                 935                 940

Lys Val Arg Arg Leu Leu Glu Ser Glu Gln Leu Arg Val Phe Val Leu
945                 950                 955                 960

Ser Lys Leu Asn Arg Met Val Gln Ser Glu Asp Ala Arg Gln Asp
                965                 970                 975

Ile Ile Pro Asp Val Glu Ile Ser Arg Lys Val Tyr Lys Gly Met Leu
            980                 985                 990

Asp Leu Leu Lys Cys Thr Val Leu Ser Leu Glu Gln Ser Tyr Ala His
            995                 1000                1005

Ala Gly Leu Gly Gly Met Ala Ser Ile Phe Gly Leu Leu Glu Ile Ala
    1010                1015                1020

Gln Thr His Tyr Tyr Ser Lys Glu Pro Asp Lys Arg Lys Arg Ser Pro
1025                1030                1035                1040

Thr Glu Ser Val Asn Thr Pro Val Gly Lys Asp Pro Gly Leu Ala Gly
                1045                1050                1055

Arg Gly Asp Pro Lys Ala Met Ala Gln Leu Arg Val Pro Gln Leu Gly
            1060                1065                1070

Pro Arg Ala Pro Ser Ala Thr Gly Lys Gly Pro Lys Glu Leu Asp Thr
    1075                1080                1085
```

-continued

```
Arg Ser Leu Lys Glu Glu Asn Phe Ile Ala Ser Ile Gly Pro Glu Val
    1090                1095                1100

Ile Lys Pro Val Phe Asp Leu Gly Thr Glu Glu Lys Lys Ser Gln
1105                1110                1115                1120

Ile Ser Ala Asp Ser Gly Val Ser Leu Thr Ser Ser Ser Gln Arg Thr
                1125                1130                1135

Asp Gln Asp Ser Val Ile Gly Val Ser Pro Ala Val Met Ile Arg Ser
            1140                1145                1150

Ser Ser Gln Asp Ser Glu Val Ser Thr Val Val Ser Asn Ser Ser Gly
            1155                1160                1165

Glu Thr Leu Gly Ala Asp Ser Asp Leu Ser Ser Asn Ala Gly Asp Gly
    1170                1175                1180

Pro Gly Gly Glu Gly Ser Val His Leu Ala Ser Ser Arg Gly Thr Leu
1185                1190                1195                1200

Ser Asp Ser Glu Ile Glu Thr Asn Ser Ala Thr Ser Thr Ile Phe Gly
                1205                1210                1215

Lys Ala His Ser Leu Lys Pro Ser Ile Lys Glu Lys Leu Ala Gly Ser
            1220                1225                1230

Pro Ile Arg Thr Ser Glu Asp Val Ser Gln Arg Val Tyr Leu Tyr Glu
            1235                1240                1245

Gly Leu Leu Gly Lys Glu Arg Ser Thr Leu Trp Asp Gln Met Gln Phe
    1250                1255                1260

Trp Glu Asp Ala Phe Leu Asp Ala Val Met Leu Glu Arg Glu Gly Met
1265                1270                1275                1280

Gly Met Asp Gln Gly Pro Gln Glu Met Ile Asp Arg Tyr Leu Ser Leu
                1285                1290                1295

Gly Glu His Asp Arg Lys Arg Leu Glu Asp Asp Glu Asp Arg Leu Leu
            1300                1305                1310

Ala Thr Leu Leu His Asn Leu Ile Ser Tyr Met Leu Leu Met Lys Val
            1315                1320                1325

Asn Lys Asn Asp Ile Arg Lys Lys Val Arg Arg Leu Met Gly Lys Ser
    1330                1335                1340

His Ile Gly Leu Val Tyr Ser Gln Gln Ile Asn Glu Val Leu Asp Gln
1345                1350                1355                1360

Leu Ala Asn Leu Asn Gly Arg Asp Leu Ser Ile Trp Ser Ser Gly Ser
                1365                1370                1375

Arg His Met Lys Lys Gln Thr Phe Val Val His Ala Gly Thr Asp Thr
            1380                1385                1390

Asn Gly Asp Ile Phe Phe Met Glu Val Cys Asp Asp Cys Val Val Leu
            1395                1400                1405

Arg Ser Asn Ile Gly Thr Val Tyr Glu Arg Trp Trp Tyr Glu Lys Leu
    1410                1415                1420

Ile Asn Met Thr Tyr Cys Pro Lys Thr Lys Val Leu Cys Leu Trp Arg
1425                1430                1435                1440

Arg Asn Gly Ser Glu Thr Gln Leu Asn Lys Phe Tyr Thr Lys Lys Cys
                1445                1450                1455

Arg Glu Leu Tyr Tyr Cys Val Lys Asp Ser Met Glu Arg Ala Ala Ala
            1460                1465                1470

Arg Gln Gln Ser Ile Lys Pro Gly Pro Glu Leu Gly Gly Glu Phe Pro
            1475                1480                1485

Val Gln Asp Leu Lys Thr Gly Glu Gly Gly Leu Leu Gln Val Thr Leu
    1490                1495                1500
```

```
Glu Gly Ile Asn Leu Lys Phe Met His Asn Gln Val Phe Ile Glu Leu
1505                1510                1515                1520

Asn His Ile Lys Lys Cys Asn Thr Val Arg Gly Val Phe Val Leu Glu
                1525                1530                1535

Glu Phe Val Pro Glu Ile Lys Glu Val Val Ser His Lys Tyr Lys Thr
            1540                1545                1550

Pro Met Ala His Glu Ile Cys Tyr Ser Val Leu Cys Leu Phe Ser Tyr
        1555                1560                1565

Val Ala Ala Val His Ser Ser Glu Gly Asp Leu Arg Thr Pro Pro Arg
    1570                1575                1580

Pro Val Ser Ser
1585

<210> SEQ ID NO 17
<211> LENGTH: 2473
<212> TYPE: DNA
<213> ORGANISM: Homo sapiens
<220> FEATURE:
<221> NAME/KEY: CDS
<222> LOCATION: (14)..(2404)

<400> SEQUENCE: 17
ccgacgagga gac atg gcg gcg gcg ccg gta gcg gct ggg tct gga gcc       49
            Met Ala Ala Ala Pro Val Ala Ala Gly Ser Gly Ala
            1               5                   10 ggc cga ggg aga cgg tcg gca gcc aca gtg gcg gct tgg ggc gga tgg      97
Gly Arg Gly Arg Arg Ser Ala Ala Thr Val Ala Ala Trp Gly Gly Trp
        15                  20                  25 ggc ggc cgg ccg cgg cct ggt aac att ctg ctg cag ctg cgg cag ggc     145
Gly Gly Arg Pro Arg Pro Gly Asn Ile Leu Leu Gln Leu Arg Gln Gly
    30                  35                  40 cag ctg acc ggc cgg ggc ctg gtc cgg gcg gtg cag ttc act gag act     193
Gln Leu Thr Gly Arg Gly Leu Val Arg Ala Val Gln Phe Thr Glu Thr
45                  50                  55                  60 ttt ttg acg gag agg gac aaa caa tcc aag tgg agt gga att cct cag     241
Phe Leu Thr Glu Arg Asp Lys Gln Ser Lys Trp Ser Gly Ile Pro Gln
                65                  70                  75 ctg ctc ctc aag ctg cac acc acc agc cac ctc cac agt gac ttt gtt     289
Leu Leu Leu Lys Leu His Thr Thr Ser His Leu His Ser Asp Phe Val
            80                  85                  90 gag tgt caa aac atc ctc aag gaa att tct cct ctt ctc tcc atg gag     337
Glu Cys Gln Asn Ile Leu Lys Glu Ile Ser Pro Leu Leu Ser Met Glu
        95                  100                 105 gct atg gca ttt gtt act gaa gag agg aaa ctt acc caa gaa acc act     385
Ala Met Ala Phe Val Thr Glu Glu Arg Lys Leu Thr Gln Glu Thr Thr
110                 115                 120 tat cca aat act tac att ttt gac ttg ttt gga ggt gtt gat ctt ctt     433
Tyr Pro Asn Thr Tyr Ile Phe Asp Leu Phe Gly Gly Val Asp Leu Leu
125                 130                 135                 140 gta gaa att ctt atg agg cct acg atc tct atc cgg gga cag aaa ctg     481
Val Glu Ile Leu Met Arg Pro Thr Ile Ser Ile Arg Gly Gln Lys Leu
                145                 150                 155 aaa ata agt gat gaa atg tcc aag gac tgc ttg agt atc ctg tat aat     529
Lys Ile Ser Asp Glu Met Ser Lys Asp Cys Leu Ser Ile Leu Tyr Asn
            160                 165                 170 acc tgt gtc tgt aca gag gga gtt aca aag cgt ttg gca gaa aag aat     577
Thr Cys Val Cys Thr Glu Gly Val Thr Lys Arg Leu Ala Glu Lys Asn
        175                 180                 185
```

```
gac ttt gtg atc ttc ctg ttt aca ttg atg aca agt aag aag aca ttc      625
Asp Phe Val Ile Phe Leu Phe Thr Leu Met Thr Ser Lys Lys Thr Phe
    190                 195                 200 tta caa aca gca acc ctc att gaa gat att tta ggt gtt aaa aag gaa      673
Leu Gln Thr Ala Thr Leu Ile Glu Asp Ile Leu Gly Val Lys Lys Glu
205                 210                 215                 220 atg atc cga cta gat gaa gtc ccc aat ctg agt tcc tta gta tcc aat      721
Met Ile Arg Leu Asp Glu Val Pro Asn Leu Ser Ser Leu Val Ser Asn
                225                 230                 235 ttc gat cag cag cag ctc gct aat ttc tgc cgg att ctg gct gtc acc      769
Phe Asp Gln Gln Gln Leu Ala Asn Phe Cys Arg Ile Leu Ala Val Thr
            240                 245                 250 att tca gag atg gat aca ggg aat gat gac aag cac acg ctt ctt gcc      817
Ile Ser Glu Met Asp Thr Gly Asn Asp Asp Lys His Thr Leu Leu Ala
        255                 260                 265 aaa aat gct caa cag aag aag agc ttg agt ttg ggg cct tct gca gct      865
Lys Asn Ala Gln Gln Lys Lys Ser Leu Ser Leu Gly Pro Ser Ala Ala
    270                 275                 280 gaa atc aat caa gcg gcc ctt ctc agc att cct ggc ttt gtt gag cgg      913
Glu Ile Asn Gln Ala Ala Leu Leu Ser Ile Pro Gly Phe Val Glu Arg
285                 290                 295                 300 ctt tgc aaa ctg gcg act cga aag gtg tca gag tca acg ggc aca gcc      961
Leu Cys Lys Leu Ala Thr Arg Lys Val Ser Glu Ser Thr Gly Thr Ala
                305                 310                 315 agc ttc ctt cag gag ttg gaa gag tgg tac aca tgg cta gac aat gct     1009
Ser Phe Leu Gln Glu Leu Glu Glu Trp Tyr Thr Trp Leu Asp Asn Ala
            320                 325                 330 ttg gtg cta gat gcc ctg atg cga gtg gcc aat gag gag tca gag cac     1057
Leu Val Leu Asp Ala Leu Met Arg Val Ala Asn Glu Glu Ser Glu His
        335                 340                 345 aat caa gcc tcc att gtg ttc cct cct cca ggg gct tct gag gag aat     1105
Asn Gln Ala Ser Ile Val Phe Pro Pro Pro Gly Ala Ser Glu Glu Asn
    350                 355                 360 ggc ctg cct cac acg tca gcc aga acc cag ctg ccc cag tca atg aag     1153
Gly Leu Pro His Thr Ser Ala Arg Thr Gln Leu Pro Gln Ser Met Lys
365                 370                 375                 380 att atg cat gag atc atg tac aaa ctg gaa gtg ctc tat gtc ctc tgc     1201
Ile Met His Glu Ile Met Tyr Lys Leu Glu Val Leu Tyr Val Leu Cys
                385                 390                 395 gtg ctg ctg atg ggg cgt cag cga aac cag gtt cac aga atg att gca     1249
Val Leu Leu Met Gly Arg Gln Arg Asn Gln Val His Arg Met Ile Ala
            400                 405                 410 gag ttc aag ctg atc cct gga ctt aat aat ttg ttt gac aaa ctg att     1297
Glu Phe Lys Leu Ile Pro Gly Leu Asn Asn Leu Phe Asp Lys Leu Ile
        415                 420                 425 tgg agg aag cat tca gca tct gcc ctt gtc ctc cat ggt cac aac cag     1345
Trp Arg Lys His Ser Ala Ser Ala Leu Val Leu His Gly His Asn Gln
    430                 435                 440 aac tgt gac tgt agc ccg gac atc acc ttg aag ata cag ttt ttg agg     1393
Asn Cys Asp Cys Ser Pro Asp Ile Thr Leu Lys Ile Gln Phe Leu Arg
445                 450                 455                 460 ctt ctt cag agc ttc agt gac cac cac gag aac aag tac ttg tta ctc     1441
Leu Leu Gln Ser Phe Ser Asp His His Glu Asn Lys Tyr Leu Leu Leu
                465                 470                 475 aac aac cag gag ctg aat gaa ctc agt gcc atc tct ctc aag gcc aac     1489
Asn Asn Gln Glu Leu Asn Glu Leu Ser Ala Ile Ser Leu Lys Ala Asn
            480                 485                 490 atc cct gag gtg gaa gct gtc ctc aac acc gac agg agt ttg gtg tgt     1537
Ile Pro Glu Val Glu Ala Val Leu Asn Thr Asp Arg Ser Leu Val Cys
        495                 500                 505
```

```
gat ggg aag agg ggc tta tta act cgt ctg ctg cag gtc atg aag aag    1585
Asp Gly Lys Arg Gly Leu Leu Thr Arg Leu Leu Gln Val Met Lys Lys
    510             515                 520 gag cca gca gag tcg tct ttc agg ttt tgg caa gct cgg gct gtg gag    1633
Glu Pro Ala Glu Ser Ser Phe Arg Phe Trp Gln Ala Arg Ala Val Glu
525             530                 535                 540 agt ttc ctc cga ggg acc acc tcc tat gca gac cag atg ttc ctg ctg    1681
Ser Phe Leu Arg Gly Thr Thr Ser Tyr Ala Asp Gln Met Phe Leu Leu
                545                 550                 555 aag cga ggc ctc ttg gag cac atc ctt tac tgc att gtg gac agc gag    1729
Lys Arg Gly Leu Leu Glu His Ile Leu Tyr Cys Ile Val Asp Ser Glu
            560                 565                 570 tgt aag tca agg gat gtg ctc cag agt tac ttt gac ctc ctg ggg gag    1777
Cys Lys Ser Arg Asp Val Leu Gln Ser Tyr Phe Asp Leu Leu Gly Glu
        575                 580                 585 ctg atg aag ttc aac gtt gat gca ttc aag aga ttc aat aaa aat atc    1825
Leu Met Lys Phe Asn Val Asp Ala Phe Lys Arg Phe Asn Lys Asn Ile
    590                 595                 600 aac acc gat gca aag ttc cag gta ttc ctg aag cag atc aac agc tcc    1873
Asn Thr Asp Ala Lys Phe Gln Val Phe Leu Lys Gln Ile Asn Ser Ser
605                 610                 615                 620 ctg gtg gac tcc aac atg ctg gtg cgc tgt gtc act ctg tcc ctg gac    1921
Leu Val Asp Ser Asn Met Leu Val Arg Cys Val Thr Leu Ser Leu Asp
                625                 630                 635 cga ttt gaa aac cag gtg gat atg aaa gtt gcc gag gta ctg tct gaa    1969
Arg Phe Glu Asn Gln Val Asp Met Lys Val Ala Glu Val Leu Ser Glu
            640                 645                 650 tgc cgc ctg ctc gcc tac ata tcc cag gtg ccc acg cag atg tcc ttc    2017
Cys Arg Leu Leu Ala Tyr Ile Ser Gln Val Pro Thr Gln Met Ser Phe
        655                 660                 665 ctc ttc cgc ctc atc aac atc atc cac gtg cag acg ctg acc cag gag    2065
Leu Phe Arg Leu Ile Asn Ile Ile His Val Gln Thr Leu Thr Gln Glu
    670                 675                 680 aac gtc agc tgc ctc aac acc agc ctg gtg atc ctg atg ctg gcc cga    2113
Asn Val Ser Cys Leu Asn Thr Ser Leu Val Ile Leu Met Leu Ala Arg
685                 690                 695                 700 cgg aaa gag cgg ctg ccc ctg tac ctg cgg ctg ctg cag cgg atg gag    2161
Arg Lys Glu Arg Leu Pro Leu Tyr Leu Arg Leu Leu Gln Arg Met Glu
                705                 710                 715 cac agc aag aag tac ccc ggc ttc ctg ctc aac aac ttc cac aac ctg    2209
His Ser Lys Lys Tyr Pro Gly Phe Leu Leu Asn Asn Phe His Asn Leu
            720                 725                 730 ctg cgc ttc tgg cag cag cac tac ctg cac aag gac aag gac agc acc    2257
Leu Arg Phe Trp Gln Gln His Tyr Leu His Lys Asp Lys Asp Ser Thr
        735                 740                 745 tgc cta gag aac agc tcc tgc atc agc ttc tca tac tgg aag gag aca    2305
Cys Leu Glu Asn Ser Ser Cys Ile Ser Phe Ser Tyr Trp Lys Glu Thr
    750                 755                 760 gtg tcc atc ctg ttg aac ccg gac cgg cag tca ccc tct gct ctc gtt    2353
Val Ser Ile Leu Leu Asn Pro Asp Arg Gln Ser Pro Ser Ala Leu Val
765                 770                 775                 780 agc tac att gag gag ccc tac atg gac ata gac agg gac ttc act gag    2401
Ser Tyr Ile Glu Glu Pro Tyr Met Asp Ile Asp Arg Asp Phe Thr Glu
                785                 790                 795 gag tgaccttggg ccaggcctcg ggaggctgct gggccagtgt gggtgagcgt        2454
Glu gggtacgatg ccacacgcc                                              2473
```

<210> SEQ ID NO 18
<211> LENGTH: 797
<212> TYPE: PRT
<213> ORGANISM: Homo sapiens

<400> SEQUENCE: 18

```
Met Ala Ala Pro Val Ala Gly Ser Gly Ala Gly Arg Gly Arg
 1               5                  10                  15

Arg Ser Ala Ala Thr Val Ala Ala Trp Gly Gly Trp Gly Gly Arg Pro
                20                  25                  30

Arg Pro Gly Asn Ile Leu Leu Gln Leu Arg Gln Gly Gln Leu Thr Gly
            35                  40                  45

Arg Gly Leu Val Arg Ala Val Gln Phe Thr Glu Thr Phe Leu Thr Glu
    50                  55                  60

Arg Asp Lys Gln Ser Lys Trp Ser Gly Ile Pro Gln Leu Leu Leu Lys
65                  70                  75                  80

Leu His Thr Thr Ser His Leu His Ser Asp Phe Val Glu Cys Gln Asn
                85                  90                  95

Ile Leu Lys Glu Ile Ser Pro Leu Leu Ser Met Glu Ala Met Ala Phe
            100                 105                 110

Val Thr Glu Glu Arg Lys Leu Thr Gln Glu Thr Thr Tyr Pro Asn Thr
        115                 120                 125

Tyr Ile Phe Asp Leu Phe Gly Gly Val Asp Leu Leu Val Glu Ile Leu
    130                 135                 140

Met Arg Pro Thr Ile Ser Ile Arg Gly Gln Lys Leu Lys Ile Ser Asp
145                 150                 155                 160

Glu Met Ser Lys Asp Cys Leu Ser Ile Leu Tyr Asn Thr Cys Val Cys
                165                 170                 175

Thr Glu Gly Val Thr Lys Arg Leu Ala Glu Lys Asn Asp Phe Val Ile
            180                 185                 190

Phe Leu Phe Thr Leu Met Thr Ser Lys Lys Thr Phe Leu Gln Thr Ala
        195                 200                 205

Thr Leu Ile Glu Asp Ile Leu Gly Val Lys Lys Glu Met Ile Arg Leu
    210                 215                 220

Asp Glu Val Pro Asn Leu Ser Ser Leu Val Ser Asn Phe Asp Gln Gln
225                 230                 235                 240

Gln Leu Ala Asn Phe Cys Arg Ile Leu Ala Val Thr Ile Ser Glu Met
                245                 250                 255

Asp Thr Gly Asn Asp Asp Lys His Thr Leu Leu Ala Lys Asn Ala Gln
            260                 265                 270

Gln Lys Lys Ser Leu Ser Leu Gly Pro Ser Ala Ala Glu Ile Asn Gln
        275                 280                 285

Ala Ala Leu Leu Ser Ile Pro Gly Phe Val Glu Arg Leu Cys Lys Leu
    290                 295                 300

Ala Thr Arg Lys Val Ser Glu Ser Thr Gly Thr Ala Ser Phe Leu Gln
305                 310                 315                 320

Glu Leu Glu Glu Trp Tyr Thr Trp Leu Asp Asn Ala Leu Val Leu Asp
                325                 330                 335

Ala Leu Met Arg Val Ala Asn Glu Glu Ser Glu His Asn Gln Ala Ser
            340                 345                 350

Ile Val Phe Pro Pro Gly Ala Ser Glu Glu Asn Gly Leu Pro His
        355                 360                 365

Thr Ser Ala Arg Thr Gln Leu Pro Gln Ser Met Lys Ile Met His Glu
    370                 375                 380
```

-continued

```
Ile Met Tyr Lys Leu Glu Val Leu Tyr Val Leu Cys Val Leu Leu Met
385                 390                 395                 400

Gly Arg Gln Arg Asn Gln Val His Arg Met Ile Ala Glu Phe Lys Leu
                405                 410                 415

Ile Pro Gly Leu Asn Asn Leu Phe Asp Lys Leu Ile Trp Arg Lys His
            420                 425                 430

Ser Ala Ser Ala Leu Val Leu His Gly His Asn Gln Asn Cys Asp Cys
        435                 440                 445

Ser Pro Asp Ile Thr Leu Lys Ile Gln Phe Leu Arg Leu Leu Gln Ser
    450                 455                 460

Phe Ser Asp His His Glu Asn Lys Tyr Leu Leu Leu Asn Asn Gln Glu
465                 470                 475                 480

Leu Asn Glu Leu Ser Ala Ile Ser Leu Lys Ala Asn Ile Pro Glu Val
                485                 490                 495

Glu Ala Val Leu Asn Thr Asp Arg Ser Leu Val Cys Asp Gly Lys Arg
                500                 505                 510

Gly Leu Leu Thr Arg Leu Leu Gln Val Met Lys Lys Glu Pro Ala Glu
            515                 520                 525

Ser Ser Phe Arg Phe Trp Gln Ala Arg Ala Val Glu Ser Phe Leu Arg
        530                 535                 540

Gly Thr Thr Ser Tyr Ala Asp Gln Met Phe Leu Leu Lys Arg Gly Leu
545                 550                 555                 560

Leu Glu His Ile Leu Tyr Cys Ile Val Asp Ser Glu Cys Lys Ser Arg
                565                 570                 575

Asp Val Leu Gln Ser Tyr Phe Asp Leu Leu Gly Glu Leu Met Lys Phe
            580                 585                 590

Asn Val Asp Ala Phe Lys Arg Phe Asn Lys Asn Ile Asn Thr Asp Ala
        595                 600                 605

Lys Phe Gln Val Phe Leu Lys Gln Ile Asn Ser Ser Leu Val Asp Ser
610                 615                 620

Asn Met Leu Val Arg Cys Val Thr Leu Ser Leu Asp Arg Phe Glu Asn
625                 630                 635                 640

Gln Val Asp Met Lys Val Ala Glu Val Leu Ser Glu Cys Arg Leu Leu
                645                 650                 655

Ala Tyr Ile Ser Gln Val Pro Thr Gln Met Ser Phe Leu Phe Arg Leu
            660                 665                 670

Ile Asn Ile Ile His Val Gln Thr Leu Thr Gln Glu Asn Val Ser Cys
        675                 680                 685

Leu Asn Thr Ser Leu Val Ile Leu Met Leu Ala Arg Arg Lys Glu Arg
    690                 695                 700

Leu Pro Leu Tyr Leu Arg Leu Leu Gln Arg Met Glu His Ser Lys Lys
705                 710                 715                 720

Tyr Pro Gly Phe Leu Leu Asn Asn Phe His Asn Leu Leu Arg Phe Trp
                725                 730                 735

Gln Gln His Tyr Leu His Lys Asp Lys Asp Ser Thr Cys Leu Glu Asn
                740                 745                 750

Ser Ser Cys Ile Ser Phe Ser Tyr Trp Lys Glu Thr Val Ser Ile Leu
        755                 760                 765

Leu Asn Pro Asp Arg Gln Ser Pro Ser Ala Leu Val Ser Tyr Ile Glu
    770                 775                 780

Glu Pro Tyr Met Asp Ile Asp Arg Asp Phe Thr Glu Glu
785                 790                 795
```

```
<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Flag-tag

<400> SEQUENCE: 19

Asp Tyr Lys Asp Asp Asp Asp Lys
 1               5
```

TNF RECEPTOR DEATH DOMAIN LIGAND PROTEINS AND INHIBITORS OF LIGAND BINDING

This application is a divisional application of application Ser. No. 08/839,032, filed Apr. 23, 1997, U.S. Pat. No. 5,891,675, which was a divisional application of application Ser. No. 08/698,551, filed Aug. 15, 1996 and issued as U.S. Pat. No. 5,712,381 on Jan. 27, 1998, which was a continuation-in-part of application Ser. No. 08/602,228, filed Feb. 15, 1996, now U.S. Pat. No. 5,843,675, which was a continuation-in-part of application Ser. No. 08/533,901, filed Sep. 26, 1995, now U.S. Pat. No. 5,852,173, which was a continuation-in-part of application Ser. No. 08/494,440, filed Jun. 19, 1995, now U.S. Pat. No. 5,849,501, which was a continuation-in-part of application Ser. No. 08/327,514, filed Oct. 19, 1994 now abandoned.

BACKGROUND OF THE INVENTION

The present invention relates to the field of anti-inflammatory substances and other substances which act by inhibiting binding to the intracellular domain of a tumor necrosis factor receptor (hereinafter "TNF-R"), such as, for example the P55 type (or TNF-R1) TNF receptor. More particularly, the present invention is directed to novel ligands which bind to the TNF-R intracellular domain and to inhibition or modulation of signal transduction by this receptor.

Tumor necrosis factor (herein "TNF") is a cytokine which produces a wide range of cellular activities. TNF causes an inflammatory response, which can be beneficial, such as in mounting an immune response to a pathogen, or when overexpressed can lead to other detrimental effects of inflammation.

The cellular effects of TNF are initiated by the binding of TNF to its receptors (TNF-Rs) on the surface of target cells. The isolation of polynucleotides encoding TNF-Rs and variant forms of such receptors has been described in European patent publication Nos. EP 308,378, EP 393,438, EP 433,900, EP 526,905 and EP 568,925; in PCT patent publication Nos. WO91/03553 and WO93/19777; and by Schall et al., Cell 61:361–370 (1990) (disclosing the P55 type TNF receptor). Processes for purification of TNF-Rs have also been disclosed in U.S. Pat. No. 5,296,592.

Native TNF-Rs are characterized by distinct extracellular, transmembrane and intracellular domains. The primary purpose of the extracellular domain is to present a binding site for TNF on the outside of the cell. When TNF is bound to the binding site, a "signal" is transmitted to the inside of the cell through the transmembrane and intracellular domains, indicating that binding has occurred. Transmission or "transduction" of the signal to the inside of the cell occurs by a change in conformation of the transmembrane and/or intracellular domains of the receptor. This signal is "received" by the binding of proteins and other molecules to the intracellular domain of the receptor, resulting in the effects seen upon TNF stimulation. Two distinct TNF receptors of ~55 kd ("TNF-R1") and ~75 kd ("TNF-R2") have been identified. Numerous studies with anti-TNF receptor antibodies have demonstrated that TNF-R1 is the receptor which signals the majority of the pleiotropic activities of TNF. Recently, the domain required for signaling cytotoxicity and other TNF-mediated responses has been mapped to the ~80 amino acid near the C-terminus of TNF-R1. This domain is therefore termed the "death domain" (hereinafter referred to as "TNF-R death domain" and "TNF-R1-DD") (see, Tartaglia et al., Cell 74:845–853 (1993)).

While TNF binding by TNF-Rs results in beneficial cellular effects, it is often desirable to prevent or deter TNF binding from causing other detrimental cellular effects. Although substantial effort has been expended investigating inhibition of TNF binding to the extracellular domain of TNF-Rs, examination of binding of proteins and other molecules to the intracellular domain of TNF-Rs has received much less attention.

However, ligands which bind to the TNF-R intracellular domain have yet to be identified. It would be desirable to identify and isolate such ligands to examine their effects upon TNF-R signal transduction and their use as therapeutic agents for treatment of TNF-induced conditions. Furthermore, identification of such ligands would provide a means for screening for inhibitors of TNF-R/intracellular ligand binding, which will also be useful as anti-inflammatory agents.

SUMMARY OF THE INVENTION

Applicants have for the first time identified novel TNF-R1-DD ligand proteins and have isolated polynucleotides encoding such ligands. Applicants have also identified a known protein which may also bind to the death domain of TNF-R.

In one embodiment, the present invention provides a composition comprising an isolated polynucleotide encoding a protein having TNF-R1-DD ligand protein activity. In preferred embodiments, the polynucleotide is selected from the group consisting of:

(a) a polynucleotide comprising the nucleotide sequence of SEQ ID NO:1 from nucleotide 2 to nucleotide 1231;

(b) a polynucleotide comprising a fragment of the nucleotide sequence of SEQ ID NO:1;

(c) a polynucleotide encoding an TNF-R1-DD ligand protein comprising the amino acid sequence of SEQ ID NO:2;

(d) a polynucleotide encoding an TNF-R1-DD ligand protein comprising a fragment of the amino acid sequence of SEQ ID NO:2;

(e) a polynucleotide comprising the nucleotide sequence of SEQ ID NO:3 from nucleotide 2 to nucleotide 415;

(f) a polynucleotide comprising a fragment of the nucleotide sequence of SEQ ID NO:3;

(g) a polynucleotide encoding an TNF-R1-DD ligand protein comprising the amino acid sequence of SEQ ID NO:4;

(h) a polynucleotide encoding an TNF-R1-DD ligand protein comprising a fragment of the amino acid sequence of SEQ ID NO:4;

(i) a polynucleotide comprising the nucleotide sequence of SEQ ID NO:9 from nucleotide 2 to nucleotide 931;

(j) a polynucleotide comprising a fragment of the nucleotide sequence of SEQ ID NO:9;

(k) a polynucleotide encoding an TNF-R1-DD ligand protein comprising the amino acid sequence of SEQ ID NO:10;

(l) a polynucleotide encoding an TNF-R1-DD ligand protein comprising a fragment of the amino acid sequence of SEQ ID NO:10;

(m) a polynucleotide comprising the nucleotide sequence of SEQ ID NO:11 from nucleotide 2 to nucleotide 1822;

(n) a polynucleotide comprising a fragment of the nucleotide sequence of SEQ ID NO:11;

(o) a polynucleotide encoding an TNF-R1-DD ligand protein comprising the amino acid sequence of SEQ ID NO:12;

(p) a polynucleotide encoding an TNF-R1-DD ligand protein comprising a fragment of the amino acid sequence of SEQ ID NO:12;

(q) a polynucleotide comprising the nucleotide sequence of SEQ ID NO:13 from nucleotide 3 to nucleotide 2846;

(r) a polynucleotide comprising a fragment of the nucleotide sequence of SEQ ID NO:13, which encodes a protein having TNF-R1-DD ligand protein activity;

(s) a polynucleotide encoding an TNF-R1-DD ligand protein comprising the amino acid sequence of SEQ ID NO:14;

(t) a polynucleotide encoding an TNF-R1-DD ligand protein comprising a fragment of the amino acid sequence of SEQ ID NO:14 and having TNF-R1-DD ligand protein activity;

(u) a polynucleotide comprising the nucleotide sequence of SEQ ID NO:15 from nucleotide 326 to nucleotide 5092;

(v) a polynucleotide comprising a fragment of the nucleotide sequence of SEQ ID NO:15;

(w) a polynucleotide encoding an TNF-R1-DD ligand protein comprising the amino acid sequence of SEQ ID NO:16;

(x) a polynucleotide encoding an TNF-R1-DD ligand protein comprising a fragment of the amino acid sequence of SEQ ID NO:16;

(y) a polynucleotide comprising the nucleotide sequence of SEQ ID NO:17 from nucleotide 14 to nucleotide 2404;

(z) a polynucleotide comprising a fragment of the nucleotide sequence of SEQ ID NO:17;

(aa) a polynucleotide encoding an TNF-R1-DD ligand protein comprising the amino acid sequence of SEQ ID NO:18;

(bb) a polynucleotide encoding an TNF-R1-DD ligand protein comprising a fragment of the amino acid sequence of SEQ ID NO:18; and (cc) a polynucleotide capable of hybridizing under stringent conditions to any one of the polynucleotides specified in (a)–(cc).

In certain preferred embodiments, the polynucleotide is operably linked to an expression control sequence. The invention also provides a host cell, including bacterial, yeast, insect and mammalian cells, transformed with such polynucleotide compositions:

Processes are also provided for producing an TNF-R1-DD ligand protein, which comprises:

(a) growing a culture of the host cell transformed with such polynucleotide compositions in a suitable culture medium; and (b) purifying the TNF-R1-DD ligand protein from the culture. The ligand protein produced according to such methods is also provided by the present invention.

Compositions comprising a protein having TNF-R1-DD ligand protein activity are also disclosed. In preferred embodiments the protein comprises an amino acid sequence selected from the group consisting of:

(a) the amino acid sequence of SEQ ID NO:2;

(b) fragments of the amino acid sequence of SEQ ID NO:2;

(c) the amino acid sequence of SEQ ID NO:4;

(d) fragments of the amino acid sequence of SEQ ID NO:4;

(e) the amino acid sequence of SEQ ID NO:6;

(f) fragments of the amino acid sequence of SEQ ID NO:6;

(g) the amino acid sequence of SEQ ID NO:10;

(h) fragments of the amino acid sequence of SEQ ID NO:10;

(i) the amino acid sequence of SEQ ID NO:12;

(j) fragments of the amino acid sequence of SEQ ID NO:12;

(k) the amino acid sequence of SEQ ID NO:14;

(l) fragments of the amino acid sequence of SEQ ID NO:14;

(m) the amino acid sequence of SEQ ID NO:16;

(n) fragments of the amino acid sequence of SEQ ID NO:16;

(o) the amino acid sequence of SEQ ID NO:18; and (p) fragments of the amino acid sequence of SEQ ID NO:18;

the protein being substantially free from other mammalian proteins. Such compositions may further comprise a pharmaceutically acceptable carrier.

Compositions comprising an antibody which specifically reacts with such TNF-R1-DD ligand protein are also provided by the present invention.

Methods are also provided for identifying an inhibitor of TNF-R death domain binding which comprise:

(a) combining an TNF-R death domain protein with an TNF-R1-DD ligand protein, said combination forming a first binding mixture; p1 (b) measuring the amount of binding between the TNF-R death domain protein and the TNF-R1-DD ligand protein in the first binding mixture;

(c) combining a compound with the TNF-R death domain protein and an TNF-R1-DD ligand protein to form a second binding mixture;

(d) measuring the amount of binding in the second binding mixture; and (e) comparing the amount of binding in the first binding mixture with the amount of binding in the second binding mixture;

wherein the compound is capable of inhibiting TNF-R death domain binding when a decrease in the amount of binding of the second binding mixture occurs. In certain preferred embodiments the TNF-R1-DD ligand protein used in such method comprises an amino acid sequence selected from the group consisting of:

(a) the amino acid sequence of SEQ ID NO:2;

(b) fragments of the amino acid sequence of SEQ ID NO:2;

(c) the amino acid sequence of SEQ ID NO:4;

(d) fragments of the amino acid sequence of SEQ ID NO:4;

(e) the amino acid sequence of SEQ ID NO:6;

(f) fragments of the amino acid sequence of SEQ ID NO:6;

(g) the amino acid sequence of SEQ ID NO:8;

(h) fragments of the amino acid sequence of SEQ ID NO:8

(i) the amino acid sequence of SEQ ID NO:10;

(j) fragments of the amino acid sequence of SEQ ID NO:10;
(k) the amino acid sequence of SEQ ID NO:12;
(l) fragments of the amino acid sequence of SEQ ID NO:12;
(m) the amino acid sequence of SEQ ID NO:14;
(n) fragments of the amino acid sequence of SEQ ID NO:14;
(o) the amino acid sequence of SEQ ID NO:16;
(p) fragments of the amino acid sequence of SEQ ID NO:16;
(q) the amino acid sequence of SEQ ID NO:18;
(r) fragments of the amino acid sequence of SEQ ID NO:18.

Compositions comprising inhibitors identified according to such method are also provided. Such compositions may include pharmaceutically acceptable carriers.

Methods are also provided for preventing or ameliorating an inflammatory condition which comprises administering a therapeutically effective amount of a composition comprising a protein having TNF-R1-DD ligand protein activity and a pharmaceutically acceptable carrier.

Other embodiments provide methods of inhibiting TNF-R death domain binding comprising administering a therapeutically effective amount of a composition comprising a protein having TNF-R1-DD ligand protein activity and a pharmaceutically acceptable carrier.

Methods are also provided for preventing or ameliorating an inflammatory condition which comprises administering to a mammalian subject a therapeutically effective amount of a composition comprising a pharmaceutically acceptable carrier and a protein selected from the group consisting of insulin-like growth factor binding protein-5 ("IGFBP-5"), and fragments thereof having TNF-R1-DD ligand protein activity. Such proteins may also be administered for inhibiting TNF-R death domain binding.

Methods of preventing or ameliorating an inflammatory condition or of inhibiting TNF-R death domain binding are provided, which comprise administering to a mammalian subject a therapeutically effective amount of inhibitors of TNF-R death domain binding, are also provided.

Methods of identifying an inhibitor of TNF-R death domain binding are also provided by the present invention which comprise:

(a) transforming a cell with a first polynucleotide encoding an TNF-R death domain protein, a second polynucleotide encoding an TNF-R1-DD ligand protein, and at least one reporter gene, wherein the expression of the reporter gene is regulated by the binding of the TNF-R1-DD ligand protein encoded by the second polynucleotide to the TNF-R death domain protein encoded by the first polynucleotide;

(b) growing the cell in the presence of and in the absence of a compound; and (c) comparing the degree of expression of the reporter gene in the presence of and in the absence of the compound;

wherein the compound is capable of inhibiting TNF-R death domain binding when a decrease in the degree of expression of the reporter gene occurs. In preferred embodiments, the cell is a yeast cell and the second polynucleotide is selected from the group consisting of:

(a) a polynucleotide comprising the nucleotide sequence of SEQ ID NO:1 from nucleotide 2 to nucleotide 1231;
(b) a polynucleotide comprising a fragment of the nucleotide sequence of SEQ ID NO:1, which encodes a protein having TNF-R1-DD ligand protein activity;
(c) a polynucleotide encoding an INF-R1-DD ligand protein comprising the amino acid sequence of SEQ ID NO:2;
(d) a polynucleotide encoding an TNF-R1-DD ligand protein comprising a fragment of the amino acid sequence of SEQ ID NO:2 and having TNF-R1-DD ligand protein activity;
(e) a polynucleotide comprising the nucleotide sequence of SEQ ID NO:3 from nucleotide 2 to nucleotide 415;
(f) a polynucleotide comprising a fragment of the nucleotide sequence of SEQ ID NO:3, which encodes a protein having TNF-R1-DD ligand protein activity;
(g) a polynucleotide encoding an TNF-R1-DD ligand protein comprising the amino acid sequence of SEQ ID NO:4;
(h) a polynucleotide encoding an TNF-R1-DD ligand protein comprising a fragment of the amino acid sequence of SEQ ID NO:4 and having TNF-R1-DD ligand protein activity;
(i) a polynucleotide comprising the nucleotide sequence of SEQ ID NO:5 from nucleotide 2 to nucleotide 559;
(j) a polynucleotide comprising a fragment of the nucleotide sequence of SEQ ID NO:5, which encodes a protein having TNF-R1-DD ligand protein activity;
(k) a polynucleotide encoding an TNF-R1-DD ligand protein comprising the amino acid sequence of SEQ ID NO:6;
(l) a polynucleotide encoding an TNF-R1-DD ligand protein comprising a fragment of the amino acid sequence of SEQ ID NO:6 and having TNF-R1-DD ligand protein activity;
(m) a polynucleotide comprising the nucleotide sequence of SEQ ID NO:7 from nucleotide 57 to nucleotide 875;
(n) a polynucleotide comprising a fragment of the nucleotide sequence of SEQ ID NO:7, which encodes a protein having TNF-R1-DD ligand protein activity;
(o) a polynucleotide encoding an TNF-R1-DD ligand protein comprising the amino acid sequence of SEQ ID NO:8;
(p) a polynucleotide encoding an INF-R1-DD ligand protein comprising a fragment of the amino acid sequence of SEQ ID NO:8 and having TNF-R1-DD ligand protein activity;
(q) a polynucleotide comprising the nucleotide sequence of SEQ ID NO:9 from nucleotide 2 to nucleotide 931;
(r) a polynucleotide comprising a fragment of the nucleotide sequence of SEQ ID NO:9;
(s) a polynucleotide encoding an TNF-R1-DD ligand protein comprising the amino acid sequence of SEQ ID NO:10;
(t) a polynucleotide encoding an TNF-R1-DD ligand protein comprising a fragment of the amino acid sequence of SEQ ID NO:10;
(u) a polynucleotide comprising the nucleotide sequence of SEQ ID NO:11 from nucleotide 2 to nucleotide 1822;
(v) a polynucleotide comprising a fragment of the nucleotide sequence of SEQ ID NO:11;
(w) a polynucleotide encoding an TNF-R1-DD ligand protein comprising the amino acid sequence of SEQ ID NO:12;
(x) a polynucleotide encoding an TNF-R1-DD ligand protein comprising a fragment of the amino acid sequence of SEQ ID NO:12;

(y) a polynucleotide comprising the nucleotide sequence of SEQ ID NO:13 from nucleotide 3 to nucleotide 2846;

(z) a polynucleotide comprising a fragment of the nucleotide sequence of SEQ ID NO:13, which encodes a protein having TNF-R1-DD ligand protein activity;

(aa) a polynucleotide encoding an TNF-R1-DD ligand protein comprising the amino acid sequence of SEQ ID NO:14;

(bb) a polynucleotide encoding an TNF-R1-DD ligand protein comprising a fragment of the amino acid sequence of SEQ ID NO:14 and having TNF-R1-DD ligand protein activity;

(cc) a polynucleotide comprising the nucleotide sequence of SEQ ID NO:15 from nucleotide 326 to nucleotide 5092;

(dd) a polynucleotide comprising a fragment of the nucleotide sequence of SEQ ID NO:15, which encodes a protein having TNF-R1-DD ligand protein activity;

(ee) a polynucleotide encoding an TNF-R1-DD ligand protein comprising the amino acid sequence of SEQ ID NO:16;

(ff) a polynucleotide encoding an TNF-R1-DD ligand protein comprising a fragment of the amino acid sequence of SEQ ID NO:16 and having TNF-R1-DD ligand protein activity;

(gg) a polynucleotide comprising the nucleotide sequence of SEQ ID NO:17 from nucleotide 14 to nucleotide 2404;

(hh) a polynucleotide comprising a fragment of the nucleotide sequence of SEQ ID NO:17, which encodes a protein having TNF-R1-DD ligand protein activity;

(ii) a polynucleotide encoding an TNF-R1-DD ligand protein comprising the amino acid sequence of SEQ ID NO:18;

(jj) a polynucleotide encoding an TNF-R1-DD ligand protein comprising a fragment of the amino acid sequence of SEQ iD NO:18 and having TNF-R1-DD ligand protein activity; and (kk) a polynucleotide capable of hybridizing under stringent conditions to any one of the polynucleotides specified in (a)–(jj), which encodes a protein having TNF-R1-DD ligand protein activity.

DETAILED DESCRIPTION OF THE INVENTION

Figure 1:
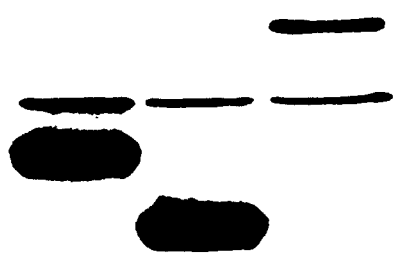
FIGS. 1 and 2 depict autoradiographs demonstrating the expression of TNF-R1-DD ligand proteins of the present invention.

The present inventors have for the first time identified and isolated novel polynucleotides which encode proteins which bind to the TNF-R death domain. As used herein "TNF-R" includes all receptors for tumor necrosis factor. The P55 type TNF-R is the preferred receptor for practicing the present invention.

The sequence of a polynucleotide encoding one such protein is set forth in SEQ ID NO:1 from nucleotides 2 to 1231. This polynucleotide has been identified as "clone 2DD." The amino acid sequence of the TNF-R1-DD ligand protein encoded by clone 2DD is set forth in SEQ ID NO:2. It is believed that clone 2DD is a partial cDNA clone of a longer full length coding sequence. However, as demonstrated herein the protein encoded by clone 2DD does bind the death domain of TNF-R (i.e., has "TNF-R1-DD ligand protein activity" as defined herein). Clone 2DD was deposited with the American Type Culture Collection on Oct. 13, 1994 and given the accession number ATCC 69706.

The protein encoded by clone 2DD is 410 amino acids in length. No identical or closely related sequences were found using BLASTN/BLASTX or FASTA searches. Therefore, clone 2DD encodes a novel protein.

The sequence of a polynucleotide encoding one such protein is set forth in SEQ ID NO:3 from nucleotides 2 to 415. This polynucleotide has been identified as "clone 3DD". The amino acid sequence of the TNF-R1-DD ligand protein encoded by clone 3DD is set forth in SEQ ID NO:4. It is believed that clone 3DD is a partial cDNA clone of a longer full length coding sequence. However, as demonstrated herein the protein encoded by clone 3DD does bind the death domain of TNF-R (i.e., has "TNF-R1-DD ligand protein activity" as defined herein). Clone 3DD was deposited with the American Type Culture Collection on Oct. 13, 1994 and given the accession number ATCC 69705.

The protein encoded by clone 3DD is 138 amino acids. No identical or closely related sequences were found using BLASTN/BLASTX or FASTA searches. Therefore, clone 3DD encodes a novel protein.

A full-length clone corresponding to clone 3DD was also isolated and identified as "clone 3TW". The nucleotide sequence of clone 3TW is reported as SEQ ID NO:13. Nucleotides 3 to 2846 of SEQ ID NO:13 encode a TNF-R1-DD ligand protein, the amino acid sequence of which is reported as SEQ ID NO:14. Amino acids 811 to 948 of SEQ ID NO:14 correspond to amino acids 1 to 138 of SEQ ID NO:4 (clone 3DD). Clone 3TW was deposited with the American Type Culture Collection on Sep. 26, 1995 and given the accession number ATCC 69904.

The sequence of a polynucleotide encoding another such protein is set forth in SEQ ID NO:5 from nucleotides 2 to 559. This polynucleotide has been identified as "clone 20DD." The amino acid sequence of the TNF-R1-DD ligand protein encoded by clone 20DD is set forth in SEQ ID NO:6. It is believed that clone 20DD is a partial cDNA clone of a longer full length coding sequence. However, as demonstrated herein the protein encoded by clone 20DD does bind the death domain of TNF-R (i.e., has "TNF-R1-DD ligand protein activity" as defined herein). Clone 20DD was deposited with the American Type Culture Collection on Oct. 13, 1994 and given the accession number ATCC 69704.

The protein encoded by clone 20DD is identical to amino acids 87 to 272 of insulin-like growth factor binding protein-5 ("IGFBP-5"), a sequence for which was disclosed in J. Biol. Chem. 266:1064–10653 (1991) by Shimasaki et al., which is incorporated herein by reference. The polynucleotide and amino acid sequences of IGFBP-5 are set forth in SEQ ID NO:7 and SEQ ID NO:8, respectively. Based upon the sequence identity between clone 20DD and IGFBP-5, IGFBP-5 and certain fragments thereof will exhibit TNF-R1-DD ligand binding activity (as defined herein).

The sequence of a polynucleotide encoding another such protein is set forth in SEQ ID NO:9 from nucleotides 2 to 931. This polynucleotide has been identified as "clone 1TU" The amino acid sequence of the TNF-R1-DD ligand protein encoded by clone 1TU is set forth in SEQ ID NO:10. It is believed that clone 1TU is a partial cDNA clone of a longer full length coding sequence. However, as demonstrated herein the protein encoded by clone 1TU does bind the death domain of TNF-R (i.e., has "TNF-R1-DD ligand protein activity" as defined herein). Clone 1TU was deposited with the American Type Culture Collection on Jun. 7, 1995 and given the accession number ATCC 69848.

The protein encoded by clone 1TU is 310 amino acids in length. No identical or closely related sequences were found using BLASTN/BLASTX or FASTA searches. Therefore, clone 1TU encodes a novel protein.

The sequence of a polynucleotide encoding another such protein is set forth in SEQ ID NO:11 from nucleotides 2 to 1822. This polynucleotide has been identified as "clone 27TU" The amino acid sequence of the TNF-R1-DD ligand protein encoded by clone 27TU is set forth in SEQ ID NO:12. It is believed that clone 27TU is a partial cDNA clone of a longer full length coding sequence. However, as demonstrated herein the protein encoded by clone 27TU does bind the death domain of TNF-R (i.e., has "TNF-R1-DD ligand protein activity" as defined herein). Clone 27TU was deposited with the American Type Culture Collection on Jun. 7, 1995 and given the accession number ATCC 69846.

The protein encoded by clone 27TU is 607 amino acids in length. No identical or closely related sequences were found using BLASTN/BLASTX or FASTA searches. Therefore, clone 27TU encodes a novel protein. 27TU may be a longer version of clone 2DD. 2DD encodes the same amino acid sequence (SEQ ID NO:2) as amino acids 198–607 encoded by 27TU (SEQ ID NO:12). The nucleotide sequences of 2DD and 27TU are also identical within this region of identity.

An additional "clone 15TU" was isolated which encoded a portion of the 27TU sequence (approximately amino acids 289–607 of SEQ ID NO:12). Clone 15TU was deposited with the American Type Culture Collection on Jun. 7, 1995 and given the accession number ATCC 69847. 15TU comprises the same nucleotide sequence as 27TU over this region of amino acids.

A full-length clone corresponding to clone 27TU was also isolated and identified as "clone 57TU4A". The nucleotide sequence of clone 57TU4A is reported as SEQ ID NO:15. Nucleotides 336 to 5092 of SEQ ID NO:15 encode a TNF-R1-DD ligand protein, the amino acid sequence of which is reported as SEQ ID NO:146 Amino acids 982 to 1588 of SEQ ID NO:16 correspond to amino acids 1 to 607 of SEQ ID NO:12 (clone 27TU). Clone 57TU4A was deposited with the American Type Culture Collection on Feb. 13, 1996 and given the accession number ATCC 69988.

A full-length clone corresponding to clone 1TU was also isolated and identified as "clone 33-1B". The nucleotide sequence of clone 33-1B is reported as SEQ ID NO:17. Nucleotides 14 to 2404 of SEQ ID NO:17 encode a TNF-R1-DD ligand protein, the amino acid sequence of which is reported as SEQ ID NO:18. Amino acids 488 to 797 of SEQ ID NO:18 correspond to amino acids 1 to 310 of SEQ ID NO:10 (clone 1TU). Clone 33-1B was deposited with the American Type Culture Collection on Aug. 13, 1996 and given the accession number ATCC 98137.

Polynucleotides hybridizing to the polynucleotides of the present invention under stringent conditions and highly stringent conditions are also part of the present invention. As used herein, "highly stringent conditions" include, for example, 0.2×SSC at 65° C.; and "stringent conditions" include, for example, 4×SSC at 65° C. or 50% formamide and 4×SSC at 42° C.

For the purposes of the present application, "TNF-R1-DD ligand protein" includes proteins which exhibit TNF-R1-DD ligand protein activity. For the purposes of the present application, a protein is defined as having "TNF-R1-DD ligand protein activity" when it binds to a protein derived from the TNF-R death domain. Activity can be measured by using any assay which will detect binding to an TNF-R death domain protein. Examples of such assays include without limitation the interaction trap assays and assays in which TNF-R death domain protein which is affixed to a surface in a manner conducive to observing binding, including without limitation those described in Examples 1 and 3. As used herein an "TNF-R death domain protein" includes the entire death domain or fragments thereof.

Fragments of the TNF-R1-DD ligand protein which are capable of interacting with the TNF-R death domain or which are capable of inhibiting TNF-R death domain binding (i.e., exhibit TNF-R1-DD ligand protein activity) are also encompassed by the present invention. Fragments of the TNF-R1-DD ligand protein may be in linear form or they may be cyclized using known methods, for example, as described in H. U. Saragovi, et al., Bio/Technology 10, 773–778 (1992) and in R. S. McDowell, et al., J. Amer. Chem. Soc. 114, 9245–9253 (1992), both of which are incorporated herein by reference. Such fragments may be fused to carrier molecules such as immunoglobulins for many purposes, including increasing the valency of TNF-R1-DD ligand protein binding sites. For example, fragments of the TNF-R1-DD ligand protein may be fused through "linker" sequences to the Fc portion of an immunoglobulin. For a bivalent form of the TNF-R1-DD ligand protein, such a fusion could be to the Fc portion of an IgG molecule. Other immunoglobulin isotypes may also be used to generate such fusions. For example, an TNF-R1-DD ligand protein—IgM fusion would generate a decavalent form of the TNF-R1-DD ligand protein of the invention.

The isolated polynucleotide of the invention may be operably linked to an expression control sequence such as the pMT2 or pED expression vectors disclosed in Kaufman et al., Nucleic Acids Res. 19, 4485–4490 (1991), in order to produce the TNF-R1-DD ligand protein recombinantly.

Many suitable expression control sequences are known in the art. General methods of expressing recombinant proteins are also known and are exemplified in R. Kaufman, Methods in Enzymology 185, 537–566 (1990). As defined herein "operably linked" means that the isolated polynucleotide of the invention and the expression control sequence are situated within a vector or cell in such a way that the TNF-R1-DD ligand protein is expressed by a host cell which has been transformed (transfected) with the ligated polynucleotide/expression control sequence.

A number of types of cells may act as suitable host cells for expression of the TNF-R1-DD ligand protein. Host cells include, for example, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL60, U937, HaK or Jurkat cells.

The TNF-R1-DD ligand protein may also be produced by operably linking the isolated polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBac® kit), and such methods are well known in the art, as described in Summers and Smith, *Texas Agricultural Experiment Station Bulletin No.* 1555 (1987), incorporated herein by reference.

Alternatively, it may be possible to produce the TNF-R1-DD ligand protein in lower eukaryotes such as yeast or in prokaryotes such as bacteria. Potentially suitable yeast strains include *Saccharomyces cerevisiae, Schizosaccharomyces pombe,* Kluyveromyces strains, Candida, or any yeast strain capable of expressing heterologous proteins. Potentially suitable bacterial strains include *Escherichia coli, Bacillus subtilis, Salmonella typhimurium,* or any bacterial strain capable of expressing heterologous proteins. If the TNF-R1-DD ligand protein is made in yeast or bacteria, it may be necessary to modify the protein produced therein, for example by phosphorylation or glycosylation of the appropriate sites, in order to obtain the functional TNF-R1-DD ligand protein. Such covalent attachments may be accomplished using known chemical or enzymatic methods.

The TNF-R1-DD ligand protein of the invention may also be expressed as a product of transgenic animals, e.g., as a component of the milk of transgenic cows, goats, pigs, or sheep which are characterized by somatic or germ cells containing a nucleotide sequence encoding the TNF-R1-DD ligand protein.

The TNF-R1-DD ligand protein of the invention may be prepared by culturing transformed host cells under culture conditions suitable to express the recombinant protein. The resulting expressed protein may then be purified from such culture (i.e., from culture medium or cell extracts) using known purification processes, such as gel filtration and ion exchange chromatography. The purification of the TNF-R1-DD ligand protein may also include an affinity column containing the TNF-R death domain or other TNF-R death domain protein; one or more column steps over such affinity resins as concanavalin A-agarose, heparin-toyopearl® or Cibacrom blue 3GA Sepharose®; one or more steps involving hydrophobic interaction chromatography using such resins as phenyl ether, butyl ether, or propyl ether; or immunoaffinity chromatography.

Alternatively, the TNF-R1-DD ligand protein of the invention may also be expressed in a form which will facilitate purification. For example, it may be expressed as a fusion protein, such as those of maltose binding protein (MBP) or glutathione-S-transferase (GST). Kits for expression and purification of such fusion proteins are commercially available from New England BioLab (Beverly, Mass.) and Pharmacia (Piscataway, N.J.), respectively. The TNF-R ligand protein can also be tagged with an epitope and subsequently purified by using a specific antibody directed to such epitope. One such epitope ("Flag") is commercially available from Kodak (New Haven, Conn.).

Finally, one or more reverse-phase high performance liquid chromatography (RP-HPLC) steps employing hydrophobic RP-HPLC media, e.g., silica gel having pendant methyl or other aliphatic groups, can be employed to further purify the TNF-R1-DD ligand protein. Some or all of the foregoing purification steps. in various combinations, can also be employed to provide a substantially homogeneous isolated recombinant protein. The TNF-R1-DD ligand protein thus purified is substantially free of other mammalian proteins and is defined in accordance with the present invention as an "isolated TNF-R1-DD ligand protein."

TNF-R1-DD ligand proteins may also be produced by known conventional chemical synthesis. Methods for constructing the proteins of the present invention by synthetic means are known to those skilled in the art. The synthetically-constructed protein sequences, by virtue of sharing primary, secondary or tertiary structural and/or conformational characteristics with TNF-R1-DD ligand proteins may possess biological properties in common therewith, including TNF-R1-DD ligand protein activity. Thus, they may be employed as biologically active or immunological substitutes for natural, purified TNF-R1-DD ligand proteins in screening of therapeutic compounds and in immunological processes for the development of antibodies.

The TNF-R1-DD ligand proteins provided herein also include proteins characterized by amino acid sequences similar to those of purified TNF-R1-DD ligand proteins but into which modification are naturally provided or deliberately engineered. For example, modifications in the peptide or DNA sequences can be made by those skilled in the art using known techniques. Modifications of interest in the TNF-R1-DD ligand protein sequences may include the replacement, insertion or deletion of a selected amino acid residue in the coding sequence. For example, one or more of the cysteine residues may be deleted or replaced with another amino acid to alter the conformation of the molecule. Mutagenic techniques for such replacement, insertion or deletion are well known to those skilled in the art (see, e.g., U.S. Pat. No. 4,518,584).

Other fragments and derivatives of the sequences of TNF-R1-DD ligand proteins which would be expected to retain TNF-R1-DD ligand protein activity in whole or in part and may thus be useful for screening or other immunological methodologies may also be easily made by those skilled in the art given the disclosures herein. Such modifications are believed to be encompassed by the present invention.

TNF-R1-DD ligand protein of the invention may also be used to screen for agents which are capable of inhibiting or blocking binding of an TNF-R1-DD ligand protein to the death domain of TNF-R, and thus may act as inhibitors of TNF-R death domain binding and/or TNF activity. Binding assays using a desired binding protein, immobilized or not, are well known in the art and may be used for this purpose using the TNF-R1-DD ligand protein of the invention. Examples 1 and 3 describe examples of such assays. Appropriate screening assays may be cell-based or cell-free. Alternatively, purified protein based screening assays may be used to identify such agents. For example, TNF-R1-DD ligand protein may be immobilized in purified form on a carrier and binding to purified TNF-R death domain may be measured in the presence and in the absence of potential inhibiting agents. A suitable binding assay may alternatively employ purified TNF-R death domain immobilized on a carrier, with a soluble form of a TNF-R1-DD ligand protein of the invention. Any TNF-R1-DD ligand protein may be used in the screening assays described above.

In such a screening assay, a first binding mixture is formed by combining TNF-R death domain protein and TNF-R1-DD ligand protein, and the amount of binding in the first binding mixture ($B_o$) is measured. A second binding mixture is also formed by combining TNF-R death domain protein, TNF-1R-DD ligand protein, and the compound or agent to be screened, and the amount of binding in the second binding mixture (B) is measured. The amounts of binding in the first and second binding mixtures are compared, for example, by performing a $B/B_o$ calculation. A compound or agent is considered to be capable of inhibiting TNF-R death domain binding if a decrease in binding in the second binding mixture as compared to the first binding mixture is observed. The formulation and optimization of binding mixtures is within the level of skill in the art. Such binding mixtures may also contain buffers and salts necessary to enhance or to optimize binding, and additional control assays may be included in the screening assay of the invention.

Alternatively, appropriate screening assays may be cell based. For example, the binding or interaction between an TNF-R ligand protein and the TNF-R death domain can be measured in yeast as described below in Examples 1 and 3.

Compounds found to reduce, preferably by at least about 10%, more preferably greater than about 50% or more, the binding activity of TNF-R1-DD ligand protein to TNF-R death domain may thus be identified and then secondarily screened in other binding assays, including in vivo assays. By these means compounds having inhibitory activity for TNF-R death domain binding which may be suitable as anti-inflammatory agents may be identified.

Isolated TNF-R1-DD ligand protein may be useful in treating, preventing or ameliorating inflammatory conditions and other conditions, such as cachexia, autoimmune disease, graft versus host reaction, osteoporosis, colitis, myelogenous leukemia, diabetes, wasting, and atherosclerosis. Isolated TNF-R1-DD ligand protein may be used itself as an inhibitor of TNF-R death domain binding or to design inhibitors of TNF-R death domain binding. Inhibitors of binding of TNF-R1-DD ligand protein to the TNF-R death domain ("TNF-R intracellular binding inhibitors") are also useful for treating such conditions.

The present invention encompasses both pharmaceutical compositions and therapeutic methods of treatment or use which employ isolated TNF-R1-DD ligand protein and/or binding inhibitors of TNF-R intracellular binding.

Isolated TNF-R1-DD ligand protein or binding inhibitors (from whatever source derived, including without limitation from recombinant and non-recombinant cell lines) may be used in a pharmaceutical composition when combined with a pharmaceutically acceptable carrier. Such a composition may also contain (in addition to TNF-R1-DD ligand protein or binding inhibitor and a carrier) diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration. The pharmaceutical composition of the invention may also contain cytokines, lymphokines, or other hematopoietic factors such as M-CSF, GM-CSF, TNF, IL-2, IL-3, IL-4, IL-5, IL-6, IL-7, IL-8, IL-9, G-CSF, Meg-CSF, stem cell factor, and erythropoietin. The pharmaceutical composition may further contain other anti-inflammatory agents. Such additional factors and/or agents may be included in the pharmaceutical composition to produce a synergistic effect with isolated TNF-R1-DD ligand protein or binding inhibitor, or to minimize side effects caused by the isolated TNF-R1-DD ligand protein or binding inhibitor. Conversely, isolated TNF-R1-DD ligand protein or binding inhibitor may be included in formulations of the particular cytokine, lymphokine, other hematopoietic factor, thrombolytic or anti-thrombotic factor, or anti-inflammatory agent to minimize side effects of the cytokine, lymphokine, other hematopoietic factor, thrombolytic or anti-thrombotic factor, or anti-inflammatory agent.

The pharmaceutical composition of the invention may be in the form of a liposome in which isolated TNF-R1-DD ligand protein or binding inhibitor is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,235,871; 4,501, 728; 4,837,028; and 4,737,323, all of which are incorporated herein by reference.

As used herein, the term "therapeutically effective amount" means the total amount of each active component of the pharmaceutical composition or method that is sufficient to show a meaningful patient benefit, i.e., treatment, healing, prevention or amelioration of an inflammatory response or condition, or an increase in rate of treatment, healing, prevention or amelioration of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of treatment or use of the present invention, a therapeutically effective amount of isolated TNF-R1-DD ligand protein or binding inhibitor is administered to a mammal having a condition to be treated. Isolated TNF-R1-DD ligand protein or binding inhibitor may be administered in accordance with the method of the invention either alone or in combination with other therapies such as treatments employing cytokines, lymphokines or other hematopoietic factors. When co-administered with one or more cytokines, lymphokines or other hematopoietic factors, isolated TNF-R1-DD ligand protein or binding inhibitor may be administered either simultaneously with the cytokine(s), lymphokine(s), other hematopoietic factor(s), thrombolytic or anti-thrombotic factors, or sequentially. If administered sequentially, the attending physician will decide on the appropriate sequence of administering isolated TNF-R1-DD ligand protein or binding inhibitor in combination with cytokine(s), lymphokine(s), other hematopoietic factor(s), thrombolytic or anti-thrombotic factors.

Administration of isolated TIN-R1-DD ligand protein or binding inhibitor used in the pharmaceutical composition or to practice the method of the present invention can be carried out in a variety of conventional ways, such as oral ingestion, inhalation, or cutaneous, subcutaneous, or intravenous injection. Intravenous administration to the patient is preferred.

When a therapeutically effective amount of isolated TNF-R1-DD ligand protein or binding inhibitor is administered orally, isolated TNF-R1-DD ligand protein or binding inhibitor will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% isolated TNF-R1-DD ligand protein or binding inhibitor, and preferably from about 25 to 90% isolated TNF-R1-DD ligand protein or binding inhibitor. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of isolated TNF-R1-DD ligand protein or binding inhibitor, and preferably from about 1 to 50% isolated TNF-R1-DD ligand protein or binding inhibitor.

When a therapeutically effective amount of isolated TNF-R1-DD ligand protein or binding inhibitor is administered by intravenous, cutaneous or subcutaneous injection, isolated TNF-R1-DD ligand protein or binding inhibitor will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to isolated TNF-R1-DD ligand protein or binding inhibitor, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art.

The amount of isolated TNF-R1-DD ligand protein or binding inhibitor in the pharmaceutical composition of the present invention will depend upon the nature and severity of the condition being treated, and on the nature of prior treatments which the patient has undergone. Ultimately, the attending physician will decide the amount of isolated TNF-R1-DD ligand protein or binding inhibitor with which to treat each individual patient. Initially, the attending physician will administer low doses of isolated TNF-R1-DD ligand protein or binding inhibitor and observe the patient's response. Larger doses of isolated TNF-R1-DD ligand protein or binding inhibitor may be administered until the optimal therapeutic effect is obtained for the patient, and at that point the dosage is not increased further. It is contemplated that the various pharmaceutical compositions used to practice the method of the present invention should contain about 0.1 µg to about 100 mg of isolated TNF-R1-DD ligand protein or binding inhibitor per kg body weight.

The duration of intravenous therapy using the pharmaceutical composition of the present invention will vary, depending on the severity of the disease being treated and the condition and potential idiosyncratic response of each individual patient. It is contemplated that the duration of each application of the isolated TNF-R1-DD ligand protein or binding inhibitor will be in the range of 12 to 24 hours of continuous intravenous administration. Ultimately the attending physician will decide on the appropriate duration of intravenous therapy using the pharmaceutical composition of the present invention.

Isolated TNF-R1-DD ligand protein of the invention may also be used to immunize animals to obtain polyclonal and monoclonal antibodies which specifically react with the TNF-R1-DD ligand protein and which may inhibit TNF-R death domain binding. Such antibodies may be obtained using either the entire TNF-R1-DD ligand protein or fragments of TNF-R1-DD ligand protein as an immunogen. The peptide immunogens additionally may contain a cysteine residue at the carboxyl terminus, and are conjugated to a hapten such as keyhole limpet hemocyanin (KLH). Methods for synthesizing such peptides are known in the art, for example, as in R. P. Merrifield, J. Amer.Chem.Soc. 85, 2149–2154 (1963); J. L. Krstenansky, et al., FEBS Lett. 211, 10 (1987).

Monoclonal antibodies binding to TNF-R1-DD ligand protein or to complex carbohydrate moieties characteristic of the TNF-R1-DD ligand glycoprotein may be useful diagnostic agents for the immunodetection of TNF-R ligand protein.

Neutralizing monoclonal antibodies binding to TNF-R1-DD ligand protein or to complex carbohydrates characteristic of TNF-R1-DD ligand glycoprotein may also be useful therapeutics for both inflammatory conditions and also in the treatment of some forms of cancer where abnormal expression of TNF-R1-DD ligand protein is involved. These neutralizing monoclonal antibodies are capable of blocking the signaling function of the TNF-R1-DD ligand protein. By blocking the binding of TNF-R1-DD ligand protein, certain biological responses to TNF are either abolished or markedly reduced. In the case of cancerous cells or leukemic cells, neutralizing monoclonal antibodies against TNF-R1-DD ligand protein may be useful in detecting and preventing the metastatic spread of the cancerous cells, which may be mediated by the TNF-R1-DD ligand protein.

Due to the similarity of their sequences to the insulin growth factor binding protein ("IGFBP-5") and fragments thereof which bind to the TNF-R death domain are proteins having TNF-R1-DD ligand protein activity as defined herein. As a result, they are also useful in pharmaceutical compositions, for treating inflammatory conditions and for inhibiting TNF-R death domain binding as described above for TNF-R1-DD ligand proteins generally.

EXAMPLE 1

Cloning of TNF-R Death Domain Ligand Protein Encoding Polynucleotide

A yeast genetic selection method, the "interaction trap" [Gyuris et al, Cell 75:791–803, 1993, which is incorporated herein by reference], was used to screen WI38 cell cDNA libraries (preparation, see below) for proteins that interact with the death domain of the P55 type 1 TNF receptor (TNF-R1-DD ). A polynucleotide encoding amino acids 326 to 413 of the P55 type TNF receptor. TNF-R1-DD, was obtained via the polymerase chain reaction (PCR) using a grafting method. This TNF-R1-DD DNA was then cloned into pEG202 by BamHI and SalI sites, generating the bait plasmid, pEG202-TNF-R1-DD. This plasmid contains the HIS3 selectable marker, and expression of the bait, the LexA-TNF-R1-DD fusion protein, is from the strong constitutive ADH1 promoter. To create the reporter strain carrying the bait protein, yeast strain EGY48, containing the reporter sequence LexAop-Leu2 in place of the chromosomal LEU2, was transformed with pEG202-TNF-R1-DD and pSH18-34 (Ura+), which carries another reporter sequence, LexAop-lacZ. For screening cDNAs encoding proteins that interact with TNF-R1-DD, the expression vector pJG4-5 (TRP1), containing the WI38 cell cDNA library (see below for the cDNA library construction), was transformed into the above strain (EGY48/pEG202-TNF-R1-DD/pSH18-34) according to the method described by Gietz et al., Nucleic Acids Res., 20:1425 (1992).

cDNA Library Construction

WI38 cell cDNA library: Double stranded cDNA was prepared from 3 ug of WI38 mRNA using reagents provided by the Superscript Choice System (Gibco/BRL, Gaithersberg, Md.) with the following substitutions: the first strand synthesis was primed using an oligo dT/XhoI primer/linker, and the dNTP mix was substituted with a mix containing methyl dCTP (Stratagene, LaJolla, Calif.). The cDNA was modified at both ends by addition of an EcoRI/NotI/SalI adapter linker and subsequently digested with XhoI. This produced cDNA molecules possessing an EcoRI/NotI/SalI overhang at the 5' end of the gene and an XhoI overhang at the 3' end. These fragments were then ligated into the yeast expression/fusion vector pJG4-5 (Gyuris et al., Cell, 75, 791–803, 1993), which contains at its amino terminus, the influenza virus HA1 epitope tag, the B42 acidic transcription activation domain, and the SV40 nuclear localization signal, all under the control of the galactose-dependent GAL1 promoter. The resulting plasmids were then electroporated into DH10B cells (Gibco/BRL). A total of $7.1 \times 10^6$ colonies were plated on LB plates containing 100 ug/ml of ampicillin. These $E.coli$ were scraped, pooled, and a large scale plasmid prep was performed using the Wizard Maxi Prep kit (Promega, Madison, Wis.), yielding 3.2 mg of supercoiled plasmid DNA.

WI38 Cell cDNA Screening Results $1 \times 10^6$ transformants were obtained on glucose Ura⁻His⁻Trp⁻ plates. These transformants were pooled and resuspended in a solution of 65% glycerol, 10 mM Tris-HCl (pH 7.5), 10 mM $MgCl_2$ and stored at −80° C. in 1 mL aliquots. For screening purposes, aliquots of these were diluted 10-fold into Ura⁻His⁻Trp⁻ CM dropout gal/raff medium (containing 2% galactose, 1% raffinose), which induces the expresssion of the library encoded proteins, and incubated at 30° C. for 4 hours. $12 \times 10^6$ colony forming units (CFUs) were then plated on standard 10 cm galactose X-Gal Ura⁻His⁻Trp⁻Leu⁻ plates at a density of $2 \times 10^5$ CFU/plate. After three days at 30° C., about 1,000 colonies were formed (Leu⁺) and of those, sixty-four colonies were LacZ⁺. In order to test if the Leu⁺/LacZ⁺ phenotype was due to the library-encoded protein, the galactose dependency of the phenotype was tested. Expression of the library-encoded proteins was turned off by growth on glucose Ura⁻His Trp⁻ master plates and then retested for galactose-dependency on glucose Ura⁻His⁻Trp⁻Leu⁻, galactose Ura⁻His⁻Trp⁻Leu⁻, glucose X-Gal Ura⁻His⁻Trp⁻, and galactose X-Gal Ura⁻His⁻Trp⁻ plates. Of these 32 colonies showed galactose-dependent growth on Leu⁻ plates and galactose-dependent blue color on X-Gal-containing medium (LacZ⁺ phenotype). Total yeast DNA was prepared from these colonies according to the method described previously (Hoffman and Winston, 1987). In order to analyze the cDNA sequences, PCR reactions were performed using the above yeast DNA as a template and oligo primers specific for the vector pJG4-5, flanking the cDNA insertion point. PCR products were purified (Qiagen PCR purification kit), subjected to restriction digest with the enzyme HaeIII, run on 1.8% agarose gels, and the restriction patterns compared. Similar and identical restriction patterns were grouped and representatives of each group were sequenced and compared to Genbank and other databases to identify any sequence homologies.

One clone of unique sequence ("2DD") and three clones with identical sequence ("3DD") were isolated and showed no signficant sequence homologies compared to Genbank and other databases. Additionally, four other clones ("20DD") with identical sequence to a portion of human insulin-like growth factor binding protein-5 (Shunichi Shimasaki et al., J. Biol. Chem. 266:10646–10653 (1991)) were isolated. The clones "2DD," "3DD" and "20DD" were chosen for further analysis. Library vector pJG4-5 containing these clones sequences were rescued from yeast by transforming the total yeast DNAs into the $E. coli$ strain KC8 and selecting for growth on Trp-ampicillin plates. These putative TNFR1 interacting proteins were then tested further for specificity of interaction with the TNF-R1-DD by the reintroduction of JG4-5 clone into EGY48 derivatives containing a panel of different baits, including bicoid, the cytoplasmic domain of the IL-1 receptor, and TNF-R1-DD. The above clones were found to interact only with the TNF-R1-DD. The interaction between these clones and TNF-R1-DD was thus judged to be specific.

U937 cDNA Screening Results

A U937 cDNA library was also constructed and screened as described above. 1,020 Leu+ colonies were found and of those, 326 colonies were also LacZ+. 62 colonies of these Leu+/LacZ+ colonies showed a galactose-dependent phenotype. One of these clones, 1TU, encodes a novel sequence. Interestingly, two clones, 15TU and 27TU, encode related or identical sequences, except that 27TU contains about 864 additional nucleotides (or about 288 amino acids) at the 5' end. 15/27TU also encode a novel sequence.

EXAMPLE 2

Expression of the TNF-R1-DD Ligand Protein cDNAs encoding TNF-R intracellular ligand proteins were released from the pJG4-5 vector with the appropriate restriction enzymes. For example, EcoRI and XhoI or NotI and XhoI were used to release cDNA from clone 2DD and clone 20DD. Where the restriction sites were also present in the internal sequence of the cDNA, PCR was performed to obtain the cDNA. For example, the cDNA fragrnent encoding "clone 3DD" was obtained through PCR due to the presence of an internal XhoI site. These cDNAs were then cloned into various expression vectors. These included pGEX (Pharmacia) or pMAL (New England Biolabs) for expression as a GST (Glutathione-S-transferase) or MBP (maltose binding protein) fusion protein in $E. coli$, a pED-based vector for mammalian expression, and pVL or pBlue-BacHis (Invitrogen) for baculovirus/insect expression. For the immunodetection of TNF-R intracellular ligand expression in mammalian cells, an epitope sequence, "Flag," was inserted into the translational start site of the pED vector, generating the pED-Flag vector. cDNAs were then inserted into the pED-Flag vector. Thus, the expression of cDNA from pED-Flag yields a protein with an amino terminal Met, followed by the "Flag" sequence, Asp-Tyr-Lys-Asp-Asp-Asp-Asp-Lys (SEQ ID NO:19). Standard DEAE-Dextran or lipofectamine methods were used to transfect COS or CHO dukx cells. Immunodetection of Flag-tagged proteins was achieved using the M2 antibody (Kodak). Moreover, an immunoaffinity column using the M2 antibody, followed by elution with the "Flag" peptide, can be used for the rapid purification of the flag-tagged protein. Similarly, affinity purification of GST-, MBP- or His-tagged fusion proteins can be performed using glutathione, amylose, or nickel columns. Detailed purification protocols are provided by the manufacturers. For many fusion proteins, the TNF-R intracellular ligand can be released by the action of thrombin, factor Xa, or enterokinase cleavage. In the case where highly purified material is required, standard purification procedures, such as ion-exchange, hydrophobic, and gel filtration chromatography will be applied in addition to the affinity purification step.

Figure 2:
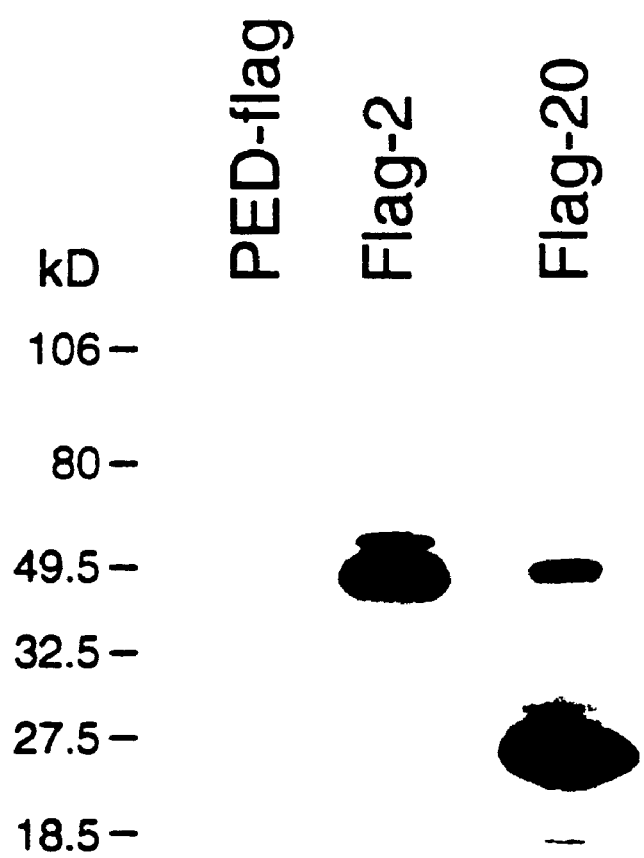

FIGS. 1 and 2 depict autoradiographs demonstrating the expression of TNF-R1-DD ligand proteins in yeast and mammalian cells. FIG. 1 shows the results of expression of isloated clones of the present invention in yeast. EGY48 was transformed with pJG4-5 containing clone 2DD, 3DD or 20DD. Cells were then grown overnight in the galactose/raffinose medium. Cell lysates were prepared and subject to 4–20% SDS gel electrophoresis, followed by Western blot analysis using anti-HA antibody (12CA5, Boehringer Mannheim, Indianapolis, Ind.). FIG. 2 shows the results of expression of Flag-2DD and Flag-20DD in COS cells. COS cells were transfected with either pED-Flag (Vector control), Flag-2DD or Flag-20DD plasmid by the lipofectamine method. Third µg of each cell lysate were prepared and subjected to 4–20% SDS gel electrophoresis, followed by Western blot analysis using M2 antibody (Kodak). The bands in the Flag-2DD and Flag-20DD lanes indicate significant expression of the respective TNF-R1-DD ligand proteins.

EXAMPLE 3

Assays of TNF-R Death Domain Binding

Two different methods were used to assay for TNF-R1-DD ligand protein activity. The first assay measures binding in the yeast strain in "interaction trap," the system used here to screen for TNF-R1-DD interacting proteins. In this system, the expression of reporter genes from both LexAop-Leu2 and LexAop-LacZ relies on the interaction between the bait protein, in this case TNF-R1DD, and the prey, the TNF-R intracellular ligand. Thus, one can measure the strength of the interaction by the level of Leu2 or LacZ expression. The most simple method is to measure the activity of the LacZ encoded protein, β-galactosidase. This activity can be judged by the degree of blueness on the X-Gal containing medium or filter. For the quantitative measurement of β-galactosidase activity, standard assays can be found in "Methods in Yeast Genetics" Cold Spring Harbor, N.Y., 1990 (by Rose, M. D., Winston, F., and Hieter, P.).

The second assay for measuring binding is a cell-free system. An example of a typical assay is described below. Purified GST-TNF-R1-DD fusion protein (2 ug) was mixed with amylose resins bound with a GST-TNF-R1-DD intracellular ligand for 2 hour at 4° C. The mixture was then centrifuged to separate bound (remained with the beads) and unbound (remained in the supernatant) GST-TNF-R1-DD. After extensive washing, the bound GST-TNF-R1-DD was eluted with maltose and detected by Western blot analysis using a GST antibody. The TNF-R1-DD or the intracellular ligand can also be immobilized on other solid supports, such as on plates or fluorobeads. The binding can then be measured using ELISA or SPA (scintillation proximity assay).

EXAMPLE 4

Characterization of TNF-R Death Domain Ligand Protein

Mapping the Interaction Site in TNF-R1

Many of the key amino acids for TNF-R signaling have been determined by site-directed mutagenesis (Tataglia et al., Cell 74:845–853 (1993). These amino acids are conserved between TNF-R and the Fas antigen, which is required for mediating cytotoxicity and other cellular responses. In order to test if the TNF-R intracellular proteins interact with these residues, the following mutations were constructed: F345A (substitution of phe at amino acid 345 to Ala), R347A, L351A, F345A/R347A/L351A, E369A, W378A and I408A. The ability of the mutant protein to interact with the intracellular ligand in the "interaction trap" system was tested.

Effect on the TNF-mediated Response

The effect of the TNF-R intracellular ligands on the TNF-mediated response can be evaluated in cells overexpressing the ligands. A number of TNF-mediated responses, including transient or prolonged responses, can be measured. For example, TNF-induced kinase activity toward either MBP (myelin basic protein) or the N-terminus (amino acids 1–79) of c-jun can be measured in COS cells or CHO cells either transiently or stably overexpressing clone 2DD, 3DD or clone 20DD. The significance of these ligand proteins in TNF-mediated cytotoxicity and other cellular responses can be measured in L929 or U937 overexpressing cells. Alternatively, other functional assays, such as the induction of gene expression or $PGE_2$ production after prolonged incubation with TNF, can also be used to measure the TNF mediated response. Conversely, the significance of the TNF-R1-DD ligand proteins in TNF signaling can be established by lowering or eliminating the expression of the ligands. These experiments can be performed using antisense expression or transgenic mice.

Enzymatic or Functional Assays

The signal transduction events initiated by TNF binding to its receptor are still largely unknown. However, one major result of TNF binding is the stimulation of cellular serine/threonine kinase activity. In addition, TNF has been shown to stimulate the activity of PC-PLC, $PLA_2$, and sphingomyelinase. Therefore, some of the TNF-R1-DD ligand proteins may possess intrinsic enzymatic activity that is responsible for these activities. Therefore, enzymatic assays can be performed to test this possibility, particularly with those clones that encode proteins with sequence homology to known enzymes. In addition to enzymatic activity, based on the sequence homology to proteins with known function, other functional assays can also be measured.

EXAMPLE 5

Isolation of Full Length Clones

In many cases, cDNAs obtained from the interaction trap method each encode only a portion of the full length protein. For example, based on identity and sequence and the lack of the initiating methionine codon, clones 2DD, 3DD and 2ODD apparently do not encode full length proteins.

Therefore, it is desirable to isolate full length clones. The cDNAs obtained from the screening, such as clone 2DD, are used as probes, and the cDNA libraries described herein, or alternatively phage cDNA libraries, are screened to obtain full length clones in accordance with known methods (see for example, "Molecular Cloning, A Laboratory Manual", by Sambrook et al., 1989 Cold Spring Harbor).

EXAMPLE 6

Antibodies Specific for TNF-R Intracellular Ligand Protein

Antibodies specific for TNF-R intracellular ligand proteins can be produced using purified recombinant protein, as described in Example 2, as antigen. Both polyclonal and monoclonal antibodies will be produced using standard techniques, such as those described in "Antibodies, a Laboratory Manual" by Ed Harlow and David Lane (1988), Cold Spring Harbor Laboratory.

EXAMPLE 7

Characterization of Clones 1TU and 15/27TU

Specificity of Interaction

The specificity of clones 1TU, 15TU and 27TU was tested using a panel of baits. The ability of these clones to bind the TNF-R death domain was compared to their binding to the intracellular domain of the second TNF-R (TNF-R $p75_{IC}$), the entire intracellular domain of TNF-R (TNF-R $p55_{IC}$), the death domain of the fas antigen (which shares 28% identity with TNF-R-DD) ($Fas_{DD}$), the Drosophila transcription factor bicoid, and a region of the IL-1 receptor known to be critical for signalling (IL-1 $R_{477-527}$). As shown in Table 1, none of these clones interacted with TNF-R $p75_{IC}$ or $Fas_{DD}$, and only 1TU interacted with bicoid. In contrast, both 1TU and 15TU bound the cytoplasmic domain of the p55 TNF-R, as well as residues 477–527 of the IL-1R. 27TU interacted relatively weakly with these sequences.

TABLE 1

| clone | TNF-$R_{DD}$ | TNF-R $p75_{IC}$ | TNF-R $p55_{IC}$ | $Fas_{DD}$ | biocoid | IL-1R (477–527) |
|---|---|---|---|---|---|---|
| 1TU | +++ | − | +++ | − | ++ | +++ |
| 15TU | +++ | ± | +++ | − | − | ++ |
| 27TU | +++ | − | + | − | − | + |

Interaction with Amino Acids Critical for Signalling

The ability of each clone to interact with four single-site mutations in the TNF-R death domain (each known to abolish signalling) was measured. As shown in Table 2, each of the clones interacted less strongly with the death domain mutants than with the wild type death domain, suggesting that these clones may bind critical residues in vivo.

TABLE 2

| clone | TNF-$R_{DD}$ | F345A | L351A | W378A | I408A |
|---|---|---|---|---|---|
| 1TU | +++ | + | ++ | ++ | + |
| 15TU | +++ | + | + | ++ | ++ |
| 27TU | +++ | + | + | ± | ++ |

Expression of 1TU, 15TU and 27TU

Figure 3A:
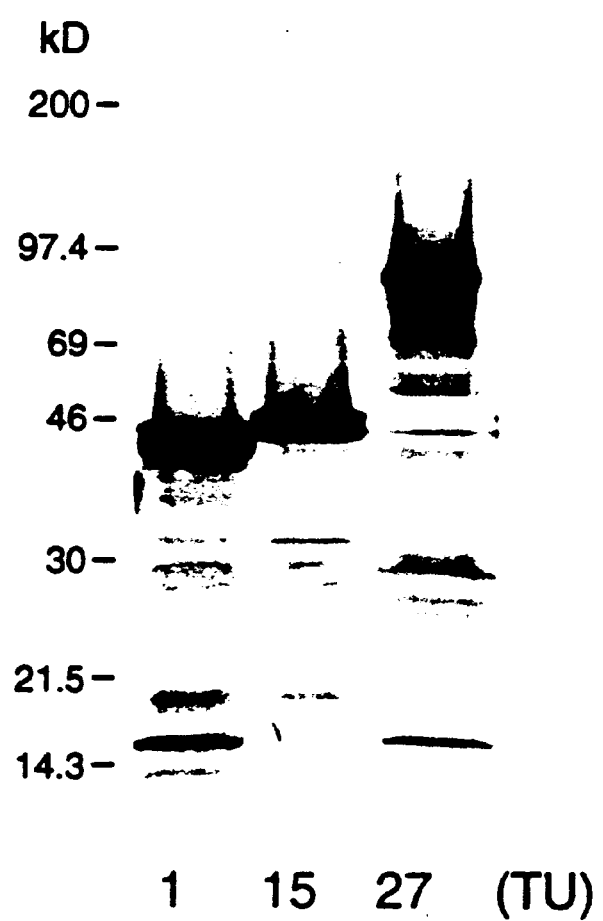
FIGS. 3A and 3B depict an autoradiograph demonstrating the expression of clones 1TU, 15TU and 27TU.
Figure 3B:
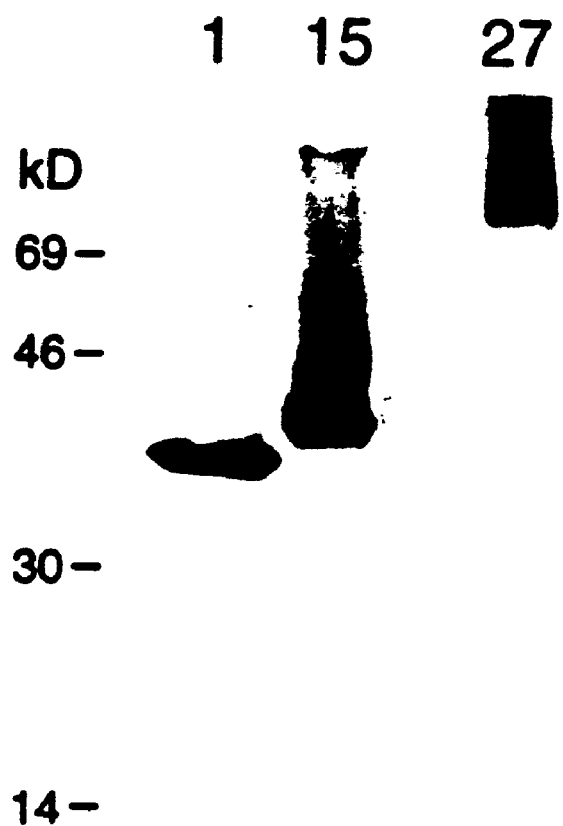

FIG. 3 depicts an autoradiograph demonstrating the expression of clones 1TU, 15TU and 27TU in yeast (A) and COS cells (B).

In (A): EGY48 was transformed with pJG4-5 containing clones 1TU, 15TU or 27TU. Cells were then grown overnight in galactose/raffinose medium. Cell lysates were prepared and subjected to 4–20% SDS gel electrophoresis, followed by Western blot analysis using anti-HA antibody (12CA5, Boehringer Mannheim).

In (B): COS cells were transfected with pED-Flag containing clones 1TU, 15TU and 27TU. Cell lysates were prepared and analyzed by Western blot using anti-Flag antibody (M2, Kodak).

Specific Binding of 1TU and 27TU to TNF-R1-DD

Figure 4:
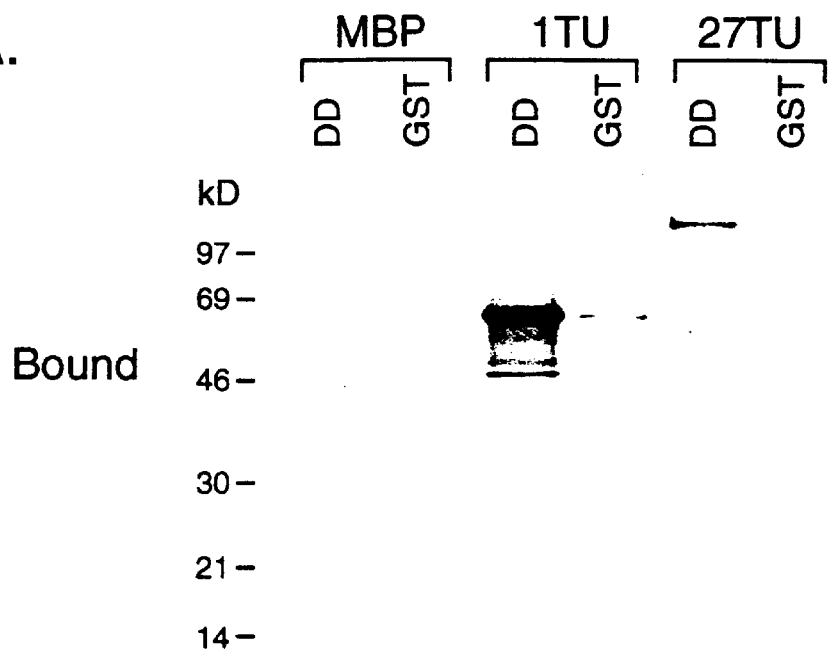
FIG. 4 demonstrates the binding of 1TU and 27TU to TNF-R1-DD. MBP, MBP-1TU or MBP-27TU (3 μg) was incubated with glutathione beads containing 3μg of either GST or GST-TNF-R1-DD in 100 μl of binding buffer (0.2% Triton, 20 mM Tris pH 7.5, 140 mM NaCl, 0.1 mM EDTA, 10 mM DTT and 5% glycerol). The reaction ws performed at 4° C. for 2 hours and centrifuged to remove unbound fraction (Unbound). The beads were then washed with 500 μl binding buffer four times and resuspended into SDS-sample buffer (Bound). These samples were analyzed by Western blot using anti-MBP antibody (New England Biolab).
Figure 4:
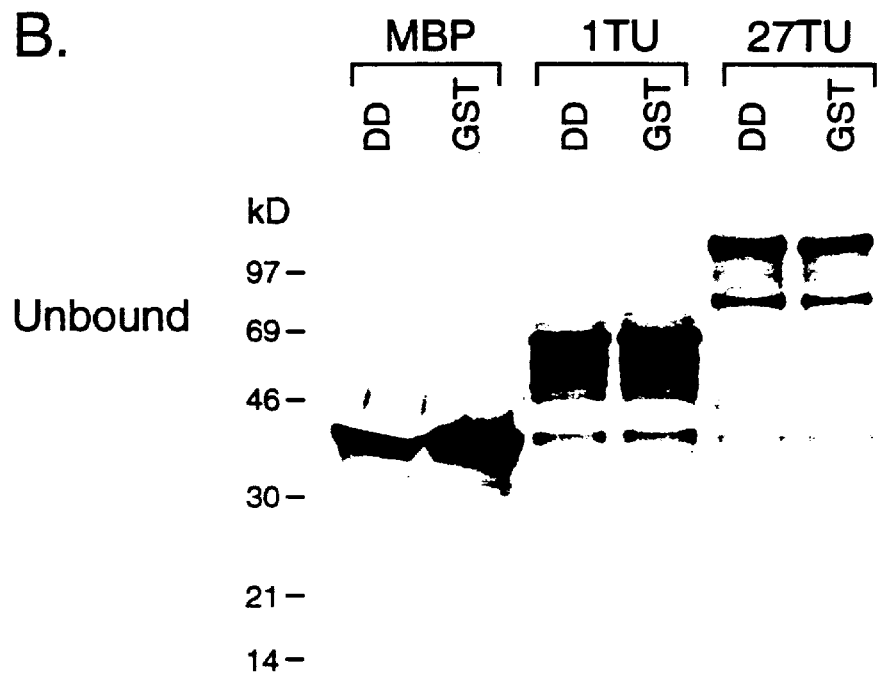

The interaction of 1TU and 27TU with TNF-R1-DD was tested using purified bacterially expressed fusion proteins. As shown in FIG. 4, MBP fusion proteins containing 1TU or 27TU bound only to TNF-R1-DD expressed as a GST fusion protein, but not to GST protein alone. In the control experiment, MBP protein did not bind either GST or GST/TNF-R1-DD. These results indicate that 1TU and 27TU bound specifically to the TNF-R1 death domain in vitro, confirming the data obtained in the interaction trap.

15TU and 27TU Activation of JNK Activity

Figure 5:
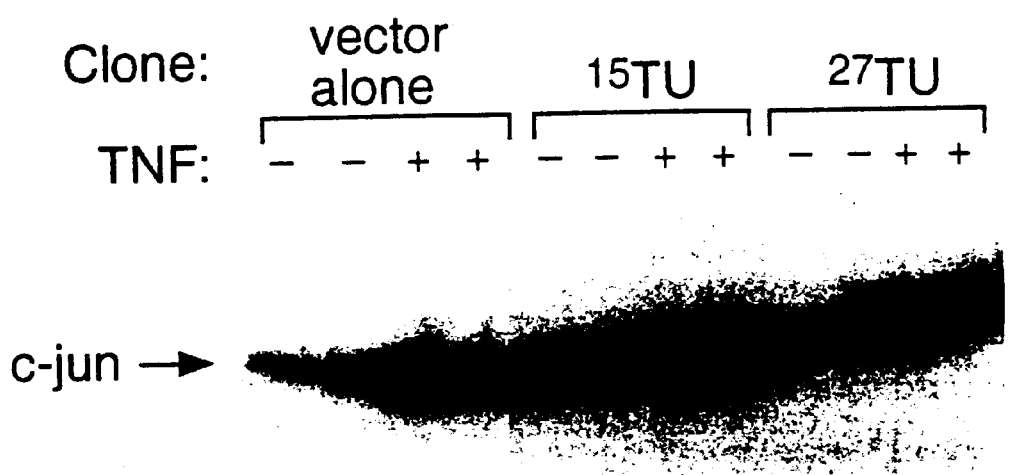
FIG. 5 demonstrates the ability of 15TU and 27TU to activate the JNK pathway. COS cells were contransfected with HA-tagged NJK1 and clones 15tu or 27TU. Cells were left untreated or treated for 15 min with 50 ng/ml TNF, and HA-JNK1 was immunoprecipitated with anti-HA antibody. JNK activity was measured in an in vitro kinase assay using GST-c-jun (amino acids 1–79) as substrate, and reactions were electrophoresed on SDS-PAGE.

The jun N-terminal kinase (JNK) is normally activated within 15 min of TNF treatment in COS cells. 15TU and 27TU were cotransfected with an epitope tagged version of JNK, HA-JNK, in duplicate. After TNF treatment, JNK was immunoprecipitated with anti-HA antibody and JNK activity was measured in immunoprecipitation kinase assays, using GST-c-jun (amino acids 1–79) as substrate). Reactions were electrophoresed on SDS-PAGE. As shown in FIG. 5, transfection of 15TU and 27TU, but not vector alone, into COS cells activated JNK even in the absence of TNF, suggesting that these clones are involved in signal transduction of TNF and the pathway leading to JNK activation in vivo.

EXAMPLE 8

Isolation, Expression and Assay of Clone 3TW

Figure 6:
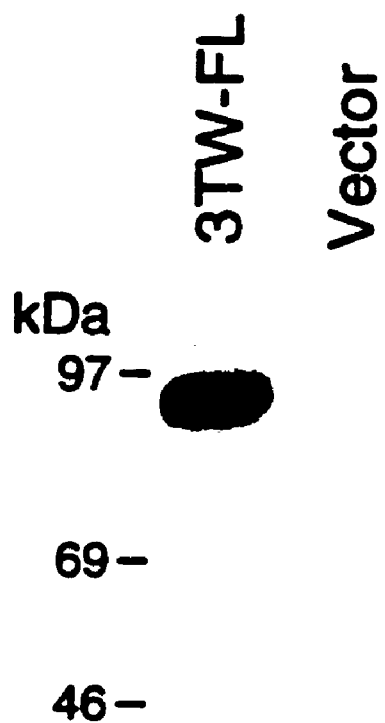
FIG. 6 is an autoradiograph of an SDS-PAGE gel of conditioned media from COS cells transfected with clone 3TW.

Clone 3TW was isolated from the W138 cDNA library using clone 3DD as a probe. Clone 3TW was expressed. FIG. 6 is an autoradiograph which demonstrates expression of 3TW (indicated by arrow).

Figure 7:
FIG. 7 is an autoradiograph which demonstrates that an antisense oligonucleotide derived from the sequence of clone 3TW inhibits TNF-induced cPLA$_2$ phosphorylation.

An antisense oligonucleotide was derived from the sequence of clone 3TW. The antisense oligonucleotide was assayed to determine its ability to inhibit TNF-induced $cPLA_2$ phosphorylation. FIG. 7 depicts the results of that experiment. Activity of the anitsense oligonucleotide (3TWAS) was compared with the full-length clone (3TWFL), Flag-3TW full length (3TWFLflag) and pED-flag vector (pEDflag). The antisense oligonucleotide inhibited phosphorylation.

What is claimed is:

1. A method of identifying an inhibitor of TNF-R death domain binding which comprises:
   (a) transforming cells with a first polynucleotide encoding a TNF-R death domain protein, a second polynucleotide encoding a TNF-R1-DD ligand protein, and at least one reporter gene, wherein the expression of the reporter gene is regulated by the binding of the TNF-R1-DD ligand protein encoded by the second polynucleotide to the TNF-R death domain protein encoded by the first polynucleotide and wherein said second polynucleotide is selected from the group consisting of:
   (i) a polynucleotide comprising the nucleotide sequence of SEQ ID NO:1 from nucleotide 2 to nucleotide 1231;
   (ii) a polynucleotide comprising a fragment of nucleotide sequence of SEQ ID NO:1, which encodes a protein having TNF-R-DD ligand protein activity;
   (iii) a polynucleotide encoding an TNF-R-DD ligand protein comprising the amino acid sequence of SEQ ID NO:2;
   (iv) a polynucleotide encoding an TNF-R1-DD ligand protein comprising a fragment of the amino acid sequence of SEQ ID NO:2 and having TNF-R1-DD ligand protein activity;
   (v) a polynucleotide comprising the nucleotide sequence of SEQ ID NO:3 from nucleotide 2 to nucleotide 415;
   (vi) a polynucleotide comprising a fragment of the nucleotide of SEQ ID NO:3, which encodes a protein having TNF-R1-DD ligand protein activity;
   (vii) a polynucleotide encoding an TNF-R1-DD ligand protein comprising the amino acid sequence of SEQ ID NO:4;
   (viii) a polynucleotide encoding an TNF-R1-DD ligand protein comprising a fragment of the amino acid sequence of SEQ ID NO:4 and having TNF-R1-DD ligand protein activity;
   (ix) a polynucleotide comprising the nucleotide sequence of SEQ ID NO:5 from nucleotide 2 to nucleotide 559;
   (x) a polynucleotide comprising a fragment of the nucleotide sequence of SEQ ID NO:5, which encodes a protein having TNF-R1-DD ligand protein activity;
   (xi) a polynucleotide encoding an TNF-R1-DD ligand protein comprising the amino acid sequence of SEQ ID NO:6;
   (xii) a polynucleotide encoding an TNF-R1-DD ligand protein comprising a fragment of the amino acid sequence of SEQ ID NO:6 and having TNF-R1-DD ligand protein activity;
   (xiii) a polynucleotide comprising the nucleotide sequence of SEQ ID NO:7 from nucleotide 57 to nucleotide 875;
   (ix) a polynucleotide comprising a fragment of the nucleotide sequence of SEQ ID NO:7, which encodes a protein having TNF-R1-DD ligand protein activity;
   (xv) a polynucleotide encoding an TNF-RI-DD ligand protein comprising the amino acid sequence of SEQ ID NO:8;
   (xvi) a polynucleotide encoding an TNF-R1-DD ligand protein comprising a fragment of the amino acid sequence of SEQ ID NO:8 and having TNF-R1-DD ligand protein activity; and
   (xvii) a polynucleotide which encodes a protein having a TNF-R1-DD ligand protein activity and hybridizes in 6×SSC at 65 degrees C. to a polynucleotide which is complementary to any one of the polynucleotides specified in (i)–(xvi);
   (b) growing transformed cells in the presence of and in the absence of a compound; and
   (c) comparing the degree of expression of the reporter gene in the presence of and in the absence of the compound,
wherein the compound is capable of inhibiting TNF-R death domain binding when a decrease in the degree of expression of the reporter gene occurs.

2. The method of claim 1 wherein the cell is a yeast cell.

3. The method of claim 1 wherein the second polynucleotide comprises the nucleotide sequence of SEQ ID NO:1 from the nucleotide 2 to nucleotide 1231.

4. The method of claim 1 wherein the second polynucleotide comprises a fragment of the nucleotide sequence of SEQ ID NO:1, which encodes a protein having TNF-R1-DD ligand protein activity.

5. The method of claim 1 wherein the second polynucleotide encodes a TNF-R1-DD ligand protein comprising the amino acid sequence of SEQ ID NO:2.

6. The method of claim 1 wherein the second polynucleotide encodes a TNF-R1-DD ligand protein comprising a fragment of the amino acid sequence of SEQ ID NO:2 and having TNF-R1-DD ligand protein activity.

7. The method of claim 1 wherein the second polynucleotide comprises the nucleotide sequence of SEQ ID NO:3 from nucleotide 2 to nucleotide 415.

8. The method of claim 1 wherein the second polynucleotide comprises a fragment of the nucleotide sequence of SEQ ID NO:3, which encodes a protein having TNF-R1-DD ligand protein activity.

9. The method of claim 1 wherein the second polynucleotide encodes a TNF-R1-DD ligand protein comprising the amino acid sequence of SEQ ID NO:4.

10. The method of claim 1 wherein the second polynucleotide encodes a TNF-R1-DD ligand protein comprising a fragment of the amino acid sequence of SEQ ID NO:4 and having TNF-R1-DD ligand protein activity.

11. The method of claim 1 wherein the second polynucleotide comprises the nucleotide sequence of SEQ ID NO:5 from nucleotide 2 to nucleotide 559.

12. The method of claim 1 wherein the second polynucleotide comprises a fragment of the nucleotide sequence of SEQ ID NO:5, which encodes a protein having TNF-R1-DD ligand protein activity.

13. The method of claim 1 wherein the second polynucleotide encodes a TNF-R1-DD ligand protein comprising the amino acid sequence of SEQ ID NO:6.

14. The method of claim 1 wherein the second polynucleotide encodes a TNF-R1-DD ligand protein comprising a fragment of the amino acid sequence of SEQ ID NO:6 and having TNF-R1-DD ligand protein activity.

15. The method of claim 1 wherein the second polynucleotide comprises the nucleotide sequence of SEQ ID NO:7 from nucleotide 57 to nucleotide 875.

16. The method of claim 1 wherein the second polynucleotide comprises a fragment of the nucleotide sequence of SEQ NO:7, which encodes a protein having TNF-R1-DD ligand protein activity.

17. The method of claim 1 wherein the second polynucleotide encodes a TNF-R1-DD ligand protein comprising the amino acid sequence of SEQ ID NO:8.

18. The method of claim 1 wherein the second polynucleotide encodes a TNF-R1-DD ligand protein comprising a fragment of the amino acid sequence of SEQ ID NO:8 and having TNF-R1-DD ligand protein activity.

19. The method of claim 1, wherein the second polynucleotide encodes a protein which has a TNF-R1-DD ligand protein activity and which hybridizes in 6×SSC at 65 degrees C. to a polynucleotide which is complementary to any one of the polynucleotides selected from the group consisting of (a) a polynucleotide comprising the nucleotide sequence of SEQ ID NO:1 from nucleotide 2 to nucleotide 1231;

(b) a polynucleotide comprising a fragment of nucleotide sequence of SEQ ID NO:1, which encodes a protein having TNF-R-DD ligand protein activity;

(c) a polynucleotide encoding an TNF-R-DD ligand protein comprising the amino acid sequence of SEQ ID NO:2;

(d) a polynucleotide encoding an TNF-R1-DD ligand protein comprising a fragment of the amino acid sequence of SEQ ID NO:2 and having TNF-R1-DD ligand protein activity;

(e) a polynucleotide comprising the nucleotide sequence of SEQ ID NO:3 from nucleotide 2 to nucleotide 415;

(f) a polynucleotide comprising a fragment of the nucleotide of SEQ ID NO:3, which encodes a protein having TNF-R1-DD ligand protein activity;

(g) a polynucleotide encoding an TNF-R1-DD ligand protein comprising the amino acid sequence of SEQ ID NO:4;

(h) a polynucleotide encoding an TNF-R1-DD ligand protein comprising a fragment of the amino acid sequence of SEQ ID NO:4 and having TNF-R1-DD ligand protein activity;

(i) a polynucleotide comprising the nucleotide sequence of SEQ ID NO:5 from nucleotide 2 to nucleotide 559;

(j) a polynucleotide comprising a fragment of the nucleotide sequence of SEQ ID NO:5, which encodes a protein having TNF-R1-DD ligand protein activity;

(k) a polynucleotide encoding an TNF-R1-DD ligand protein comprising the amino acid sequence of SEQ ID NO:6;

(l) a polynucleotide encoding an TNF-R1-DD ligand protein comprising a fragment of the amino acid sequence of SEQ ID NO:6 and having TNF-R1-DD ligand protein activity;

(m) a polynucleotide comprising the nucleotide sequence of SEQ ID NO:7 from nucleotide 57 to nucleotide 875;

(n) a polynucleotide comprising a fragment of the nucleotide sequence of SEQ ID NO:7, which encodes a protein having TNF-R1-DD ligand protein activity;

(o) a polynucleotide encoding an TNF-R1-DD ligand protein comprising the amino acid sequence of SEQ ID NO:8; or (p) a polynucleotide encoding an TNF-R1-DD ligand protein comprising a fragment of the amino acid sequence of SEQ ID NO:8 and having TNF-R1-DD ligand protein activity.

20. A method of identifying an inhibitor of TNF-R death domain binding which comprises:

(a) transforming cells with a first polynucleotide encoding a TNF-R death domain protein, a second polynucleotide encoding a TNF-R1-DD ligand protein, and at least one reporter gene, wherein the expression of the reporter gene is regulated by the binding of the TNF-R1-DD ligand protein encoded by the second polynucleotide to the TNF-R death domain protein encoded by the first polynucleotide and wherein said second polynucleotide is selected from the group consisting of:

(i) a polynucleotide comprising the nucleotide sequence of SEQ ID NO:9 from nucleotide 2 to nucleotide 931;

(ii) a polynucleotide comprising a fragment of the nucleotide sequence of SEQ ID NO:9, which encodes a protein having TNF-R1-DD ligand protein activity;

(iii) a polynucleotide encoding a TNF-R1-DD ligand protein comprising the amino acid sequence of SEQ ID NO:10;

(iv) a polynucleotide encoding an TNF-R1-DD ligand protein comprising a fragment of the amino acid sequence of SEQ ID NO: 10 and having TNF-R1-DD ligand protein activity;

(v) a polynucleotide comprising the nucleotide sequence of SEQ ID NO:11 from nucleotide 2 to nucleotide 1822;

(vi) a polynucleotide comprising a fragment of the nucleotide sequence of SEQ ID NO:11, which encodes a protein having TNF-R1-DD ligand protein activity;

(vii) a polynucleotide encoding an TNF-R1-DD ligand protein comprising the amino acid sequence of SEQ ID NO:12; and (viii) a polynucleotide encoding an TNF-R1-DD ligand protein comprising a fragment of the amino acid sequence of SEQ ID NO:12 and having TNF-R1-DD ligand protein activity; and (ix) a polynucleotide which encodes a protein having a TNF-R1-DD ligand protein activity and hybridizes in 6×SSC at 65 degrees C. to a polynucleotide which is complementary to any one of the polynucleotides specified in (i)–(viii);

(b) growing transformed cells in the presence of and in the absence of a compound; and (c) comparing the degree of expression of the reporter gene in the presence of and in the absence of the compound, wherein the compound is capable of inhibiting TNF-R death domain binding when a decrease in the degree of expression of the reporter gene occurs.

21. The method of claim 20 wherein the second polynucleotide comprises the nucleotide sequence of SEQ ID NO:9 from nucleotide 2 to nucleotide 931.

22. The method of claim 20 wherein the second polynucleotide comprises a fragment of the nucleotide sequence of SEQ ID NO:9, which encodes a protein having TNF-R1-DD ligand protein activity.

23. The method of claim 20 wherein the second polynucleotide encodes a TNF-R1-DD ligand protein comprising the amino acid sequence of SEQ ID NO:10.

24. The method of claim 20 wherein the second polynucleotide encodes a TNF-R1-DD ligand protein comprising a fragment of the amino acid sequence of SEQ ID NO:10 and having TNF-R1-DD ligand protein activity.

25. The method of claim 20 wherein the second polynucleotide comprises the nucleotide sequence of SEQ ID NO:11 from nucleotide 2 to nucleotide 1822.

26. The method of claim 20 wherein the second polynucleotide comprises a fragment of the nucleotide sequence of SEQ ID NO:11, which encodes a protein having TNF-R1-DD ligand protein activity.

27. The method of claim 20 wherein the second polynucleotide encodes a TNF-R1-DD ligand protein comprising the amino acid sequence of SEQ ID NO:12.

28. The method of claim 20 wherein the second polynucleotide encodes a TNF-R1-DD ligand protein comprising a fragment of the amino acid sequence of SEQ ID NO:12 and having TNF-R1-DD ligand protein activity.

29. The method of claim 20, wherein the cell is a yeast cell.

30. The method of claim 20, wherein the second polynucleotide encodes a protein which has a TNF-R1-DD ligand protein activity and which hybridizes in 6×SSC at 65 degrees C. to a polynucleotide which is complementary to any one of the polynucleotides selected from the group consisting of
(a) a polynucleotide comprising the nucleotide sequence of SEQ ID NO:9 from nucleotide 2 to nucleotide 931;
(b) a polynucleotide comprising a fragment of the nucleotide sequence of SEQ ID NO:9, which encodes a protein having TNF-R1-DD ligand protein activity;
(c) a polynucleotide encoding a TNF-R1-DD ligand protein comprising the amino acid sequence of SEQ ID NO:10;
(d) a polynucleotide encoding an TNF-R1-DD ligand protein comprising a fragment of the amino acid sequence of SEQ ID NO:10 and having TNF-R1-DD ligand protein activity;
(e) a polynucleotide comprising the nucleotide sequence of SEQ ID NO:11 from nucleotide 2 to nucleotide 1822;
(f) a polynucleotide comprising a fragment of the nucleotide sequence of SEQ ID NO:11, which encodes a protein having TNF-R1-DD ligand protein activity;
(g) a polynucleotide encoding an TNF-R1-DD ligand protein comprising the amino acid sequence of SEQ ID NO:12; or
(h) a polynucleotide encoding an TNF-R1-DD ligand protein comprising a fragment of the amino acid sequence of SEQ ID NO:12 and having TNF-R1-DD ligand protein activity.

31. A method of identifying an inhibitor of TNF-R death domain binding which comprises:
(a) transforming cells with a first polynucleotide encoding a TNF-R death domain protein, a second polynucleotide encoding a TNF-R1-DD ligand protein, and at least one reporter gene, wherein the expression of the reporter gene is regulated by the binding of the TNF-R1-DD ligand protein encoded by the second polynucleotide to the TNF-R death domain protein encoded by the first polynucleotide and wherein said second polynucleotide is selected from the group consisting of:
(i) a polynucleotide comprising the nucleotide sequence of SEQ ID NO:13 from nucleotide 3 to nucleotide 2846;
(ii) a polynucleotide comprising a fragment of the nucleotide sequence of SEQ ID NO:13, which encodes a protein having TNF-R1-DD ligand protein activity;
(iii) a polynucleotide encoding an TNF-R1-DD ligand protein comprising the amino acid sequence of SEQ ID NO:14;
(iv) a polynucleotide encoding an TNF-R1-DD ligand protein comprising a fragment of the amino acid sequence of SEQ ID NO:14 and having TNF-R1-DD ligand protein activity; and
(v) a polynucleotide which encodes a protein having a TNF-R1-DD ligand protein activity and hybridizes in 6×SSC at 65 degrees C. to a polynucleotide which is complementary to any one of the polynucleotides specified in (i)–(iv);
(b) growing transformed cells in the presence of and in the absence of a compound; and
(c) comparing the degree of expression of the reporter gene in the presence of and in the absence of the compound,
wherein the compound is capable of inhibiting TNF-R death domain binding when a decrease in the degree of expression of the reporter gene occurs.

32. The method of claim 31 wherein the second polynucleotide comprises the nucleotide sequence of SEQ ID NO:13 from nucleotide 3 to nucleotide 2846.

33. The method of claim 31 wherein the second polynucleotide comprises a fragment of the nucleotide sequence of SEQ ID NO:13, which encodes a protein having TNF-R1-DD ligand protein activity.

34. The method of claim 31 wherein the second polynucleotide encodes a TNF-R1-DD ligand protein comprising the amino acid sequence of SEQ ID NO:14.

35. The method of claim 31 wherein the second polynucleotide encodes a TNF-R1-DD ligand protein comprising a fragment of the amino acid sequence of SEQ ID NO:14 and having TNF-R1-DD ligand protein activity.

36. The method of claim 31, wherein the cell is a yeast cell.

37. The method of claim 31, wherein the second polynucleotide encodes a protein which has a TNF-R1-DD ligand protein activity and which hybridizes in 6×SSC at 65 degrees C. to a polynucleotide which is complementary to any one of the polynucleotides selected from the group consisting of
(a) a polynucleotide comprising the nucleotide sequence of SEQ ID NO:13 from nucleotide 3 to nucleotide 2846;
(b) a polynucleotide comprising a fragment of the nucleotide sequence of SEQ ID NO:13, which encodes a protein having TNF-R1-DD ligand protein activity;
(c) a polynucleotide encoding an TNF-R1-DD ligand protein comprising the amino acid sequence of SEQ ID NO:14; or
(d) a polynucleotide encoding an TNF-R1-DD ligand protein comprising a fragment of a the amino acid sequence of SEQ ID NO:14 and having TNF-R1-DD ligand protein activity.

38. A method of identifying an inhibitor of TNF-R death domain binding which comprises:
(a) transforming cells with a first polynucleotide encoding a TNF-R death domain protein, a second polynucleotide encoding a TNF-R1-DD ligand protein, and at least one reporter gene, wherein the expression of the reporter gene is regulated by the binding of the TNF-R1-DD ligand protein encoded by the second polynucleotide to the TNF-R death domain protein encoded by the first polynucleotide and wherein said second polynucleotide is selected from the group consisting of:
  (i) a polynucleotide comprising the nucleotide sequence of SEQ ID NO:15 from nucleotide 326 to nucleotide 5092;
  (ii) a polynucleotide comprising a fragment of the nucleotide sequence of SEQ ID NO:15, which encodes a protein having TNF-R1-DD ligand protein activity;
  (iii) a polynucleotide encoding a TNF-R1-DD ligand protein comprising the amino acid sequence of SEQ ID NO:16;
  (iv) a polynucleotide encoding a TNF-R1-DD ligand protein comprising a fragment of the amino acid sequence of SEQ ID NO:16 and having TNF-R1-DD ligand protein activity; and
  (v) a polynucleotide which encodes a protein having a TNF-R1-DD ligand protein activity and hybridizes in 6×SSC at 65 degrees C. to a polynucleotide which is complementary to any one of the polynucleotides specified in (i)–(iv);
(b) growing transformed cells in the presence of and in the absence of a compound; and
(c) comparing the degree of expression of the reporter gene in the presence of and in the absence of the compound, wherein the compound is capable of inhibiting TNF-R death domain binding when a decrease in the degree of expression of the reporter gene occurs.

39. The method of claim 38 the second polynucleotide comprises the nucleotide sequence of SEQ ID NO:15 from nucleotide 326 to nucleotide 5092.

40. The method of claim 38 wherein the second polynucleotide comprises a fragment of the nucleotide sequence of SEQ ID NO:15, which encodes a protein having TNF-R1-DD ligand protein activity.

41. The method of claim 38 wherein the second polynucleotide encodes a TNF-R1-DD ligand protein comprising the amino acid sequence of SEQ ID NO:16.

42. The method of claim 38 wherein the second polynucleotide encodes a TNF-R1-DD ligand protein comprising a fragment of the amino acid sequence of SEQ ID NO:16 and having TNF-R1-DD ligand protein activity.

43. The method of claim 38, wherein the cell is a yeast cell.

44. The method of claim 38, wherein the second polynucleotide encodes a protein which has a TNF-R1-DD ligand protein activity and which hybridizes in 6×SSC at 65 degrees C. to a polynucleotide which is complementary to any one of the polynucleotides selected from the group consisting of
  (a) a polynucleotide comprising the nucleotide sequence of SEQ ID NO:15 from nucleotide 326 to nucleotide 5092;
  (b) a polynucleotide comprising a fragment of the nucleotide sequence of SEQ ID NO:15, which encodes a protein having TNF-R1-DD ligand protein activity;
  (c) a polynucleotide encoding a TNF-R1-DD ligand protein comprising the amino acid sequence of SEQ ID NO:16; or
  (d) a polynucleotide encoding a TNF-R1-DD ligand protein comprising a fragment of the amino acid sequence of SEQ ID NO:16 and having TNF-R1-DD ligand protein activity.

45. A method of identifying an inhibitor of TNF-R death domain binding which comprises:
(a) transforming cells with a first polynucleotide encoding a TNF-R death domain protein, a second polynucleotide encoding a TNF-R1-DD ligand protein, and at least one reporter gene, wherein the expression of the reporter gene is regulated by the binding of the TNF-R1-DD ligand protein encoded by the second polynucleotide to the TNF-R death domain protein encoded by the first polynucleotide and wherein said second polynucleotide is selected from the group consisting of:
  (i) a polynucleotide comprising the nucleotide sequence of SEQ ID NO:17 from nucleotide 14 to nucleotide 2404;
  (ii) a polynucleotide comprising a fragment of the nucleotide sequence of SEQ ID NO:17, which encodes a protein having TNF-R1-DD ligand protein activity;
  (iii) a polynucleotide encoding a TNF-R1-DD ligand protein comprising the amino acid sequence of SEQ ID NO:18;
  (iv) a polynucleotide encoding a TNF-R1-DD ligand protein comprising a fragment of the amino acid sequence of SEQ ID NO:18 and having TNF-R1-DD ligand activity; and
  (v) a polynucleotide which encodes a protein having a TNF-R1 -DD ligand protein activity and hybridizes in 6×SSC at 65 degrees C. to a polynucleotide which is complementary to any one of the polynucleotides specified in (i)–(iv);
(b) growing transformed cells in the presence of and in the absence of a compound; and
(c) comparing the degree of expression of the reporter gene in the presence of and in the absence of the compound, wherein the compound is capable of inhibiting TNF-R death domain binding when a decrease in the degree of expression of the reporter gene occurs.

46. The method of claim 45 wherein the second polynucleotide comprises the nucleotide sequence of SEQ ID NO:17 from nucleotide 14 to nucleotide 2404.

47. The method of claim 45 wherein the second polynucleotide comprises a fragment of the nucleotide sequence of SEQ ID NO:17, which encodes a protein having TNF-R1-DD ligand protein activity.

48. The method of claim 45 wherein the second polynucleotide encodes a TNF-R1-DD ligand protein comprising the amino acid sequence of SEQ ID NO:18.

49. The method of claim 45 wherein the second polynucleotide encodes a TNF-R1-DD ligand protein comprising a fragment of the amino acid sequence of SEQ ID NO:18 and having TNF-R1-DD ligand protein activity.

50. The method of claim 45, wherein the cell is a yeast cell.

51. The method of claim 45, wherein the second polynucleotide encodes a protein which has a TNF-R1-DD ligand protein activity and which hybridizes in 6×SSC at 65 degrees C. to a polynucleotide which is complementary to any one of the polynucleotides selected from the group consisting of
  (a) a polynucleotide comprising the nucleotide sequence of SEQ ID NO:17 from nucleotide 14 to nucleotide 2404;

(b) a polynucleotide comprising a fragment of the nucleotide sequence of SEQ ID NO:17, which encodes a protein having TNF-R1-DD ligand protein activity;

(c) a polynucleotide encoding a TNF-R1-DD ligand protein comprising the amino acid sequence of SEQ ID NO:18; or (d) a polynucleotide encoding a TNF-R1-DD ligand protein comprising a fragment of the amino acid sequence of SEQ ID NO:18 and having TNF-R1-DD ligand activity.

* * * * *